US010065924B2

(12) United States Patent
Nicolaou et al.

(10) Patent No.: US 10,065,924 B2
(45) Date of Patent: Sep. 4, 2018

(54) PREPARATION AND BIOLOGICAL EVALUATION OF VIRIDICATUMTOXIN ANALOGS

(71) Applicant: WILLIAM MARSH RICE UNIVERSITY, Houston, TX (US)

(72) Inventors: Kyriacos C Nicolaou, Houston, TX (US); Christopher R. H. Hale, Houston, TX (US); Christian Nilewski, Houston, TX (US); Heraklidia Ioannidou, Houston, TX (US); Abdellatif El Marrouni, Houston, TX (US)

(73) Assignee: WILLIAM MARSH RICE UNIVERSITY, Houston, TX (US)

( * ) Notice: Subject to any disclaimer, the term of this patent is extended or adjusted under 35 U.S.C. 154(b) by 0 days.

(21) Appl. No.: 15/327,912

(22) PCT Filed: Jul. 22, 2015

(86) PCT No.: PCT/US2015/041494
§ 371 (c)(1),
(2) Date: Jan. 20, 2017

(87) PCT Pub. No.: WO2016/014643
PCT Pub. Date: Jan. 28, 2016

(65) Prior Publication Data
US 2017/0210699 A1 Jul. 27, 2017

Related U.S. Application Data

(60) Provisional application No. 62/027,500, filed on Jul. 22, 2014.

(51) Int. Cl.
A61K 31/65 (2006.01)
C07C 237/26 (2006.01)
C07C 235/82 (2006.01)
C07D 261/20 (2006.01)
A61K 45/06 (2006.01)

(52) U.S. Cl.
CPC ............ C07C 235/82 (2013.01); A61K 31/65 (2013.01); A61K 45/06 (2013.01); C07C 237/26 (2013.01); C07D 261/20 (2013.01); C07C 2603/94 (2017.05)

(58) Field of Classification Search
CPC . C07C 235/82; C07C 237/26; C07C 2603/94; C07D 261/20; A61K 31/65
USPC .......................................... 514/152; 552/203
See application file for complete search history.

(56) References Cited

U.S. PATENT DOCUMENTS

2010/0291622 A1 11/2010 Tomoda et al.
2013/0338117 A1 12/2013 Ricciardi

FOREIGN PATENT DOCUMENTS

WO    WO 2009/008906    1/2009

OTHER PUBLICATIONS

Breinholt, et al., "Hypomycetin—an Antifungal, tetracyclic Metabolite from *Hypomyces aurantius*: Production, Structure and Biosynthesis," *Acta Chem. Scand.*, 51:855-860, 1997.
Brubaker and Myers, "A practical, enantioselective synthetic route to a key precursor to the tetracycline antibiotics." *Org. Lett.*, 9:3523-3525, 2007.
Charest, et al., "Synthesis of (-)-Tetracycline," *J. Am. Chem. Soc.*, 127:8292-8293, 2005.
Charest, et al., "A Convergent Enantioselective Route to Structurally Diverse 6-Deoxytetracycline Antibiotics," *Science*, 308, 395-398, 2005.
Chooi, et al., "Identification of the Viridicatumtoxin and Griseofulvin Gene Clusters from *Penicillium aethiopicum*," *Chem. Biol.*, 17:483-494, 2010.
Chooi, et al., "Discovery and Characterization of a Group of Fungal Polycyclic Polyketide Prenyltransferases," *J. Am. Chem. Soc.*, 134:9428-9437, 2012.
Chooi, et al., J. Am. Chem. Soc., 135:16805-16808, 2013.
Chopra and Roberts, "Tetracycline antibiotics: mode of action, applications, molecular biology, and epidemiology of bacterial resistance," *Microbiol. Mol. Biol. R.*, 65:232-260, 2001.
De Jesus, A.E., et al., "Biosynthesis of viridicatumtoxin, a mycotoxin from Penicillin expansum," *J. Chem. Soc., Chem. Comm.*, 902-904, 1982.
Hutchison, et al., "Viridicatumtoxin, a new mycotoxin from Penicillium viridicatum Westling," *Toxicol. Appl. Pharmacol.*, 24:507-509, 1973.

(Continued)

Primary Examiner — Barbara P Badio
(74) Attorney, Agent, or Firm — Parker Highlander PLLC

(57) ABSTRACT

In one aspect, the present invention provides novel derivatives of viridicatumtoxin of the formula wherein the variables are as defined herein. The application also provides compositions, methods of treatment, and methods of synthesis thereof.

20 Claims, 4 Drawing Sheets

(56) References Cited

OTHER PUBLICATIONS

Inokoshi, et al., "Spirohexalines, new inhibitors of bacterial undecaprenyl pyrophosphate synthase, produced by Penicillium brasilianum FKI-3368," *J. Antibiot.*, 66:37-41, 2013.

Koyama, et al., "Anti-infectious agents against MRSA." *Molecules*, 18:204-224, 2013.

Kummer, et al., "A practical, convergent route to the key precursor to the tetracycline antibiotics." *Chem. Sci.*, 2:1710-1718, 2011.

Nicolaou, et al., "Total synthesis and structural revision of viridicatumtoxin B." *Angew. Chem. Int. Ed.*, (52) 8736-8741, 2013.

Nicolaou, et al., "Total synthesis of viridicatumtoxin B and analogues thereof: strategy evolution, structural revision, and biological evaluation." *J. Am. Chem. Soc.*, 136(34):12137-12160, 2014.

National Center for Biotechnology Information. PubChem Compound Database; CID=72203888, https://pubchem.ncbi.nlm.nih.gov/compound/72203888.

PCT International Search Report and Written Opinion issued in International Application No. PCT/US2015/041494; dated Oct. 19, 2015.

Sun, et al., "A Robust Platform for the Synthesis of New Tetracycline Antibiotics" *J. Am. Chem. Soc.*, 130:17913-17927, 2008.

Sutcliffe, et al., "Antibacterial activity of eravacycline (TP-434), a novel fluorocycline, against hospital and community pathogens." *Antimicrob. Agents Chemother.*, 57:5548-5558, 2013.

Tally, et al., "Glycylcyclines: a new generation of tetracyclines" *J. Antimicrob. Chemother.*, 35:449-452, 1995.

Wright and Myers, "Methodological Advances Permit the Stereocontrolled Construction of Diverse Fully Synthetic Tetracyclines Containing an All-Carbon Quaternary Center at Position C5a." *Tetrahedron*, 67:9853-9869, 2011.

Wzorek, et al., "A macrocyclic approach to tetracycline natural products. Investigation of transannular alkylations and Michael additions." *Org. Lett.*, 14:5840-5843, 2012.

Zheng, et al., "Viridicatnmtoxin B, a new anti-MRSA agent from Penicillium sp. FR11." *J. Antibiot.* 61:633-637, 2008.

a)
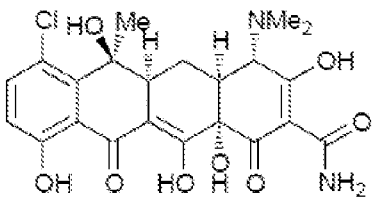
4: chlortetracycline (Aureomycin®)
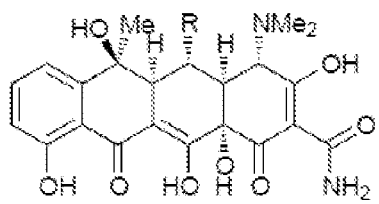
5: R = OH, oxytetracycline (Terramycin®)
6: R = H, tetracycline (Achromycin®)
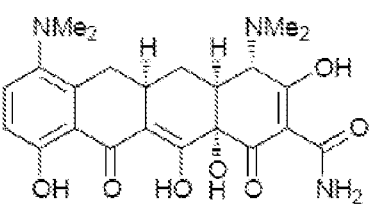
7: minocycline (Minocin®)
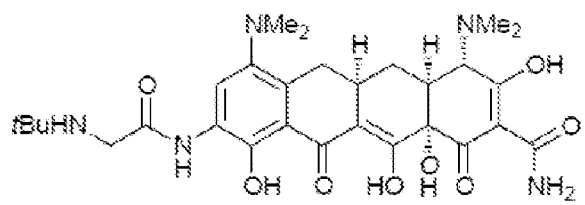
9: tigecycline (Tygacil®)
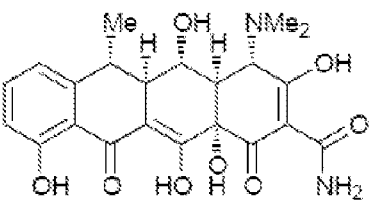
8: doxycycline (Vibramycin®)
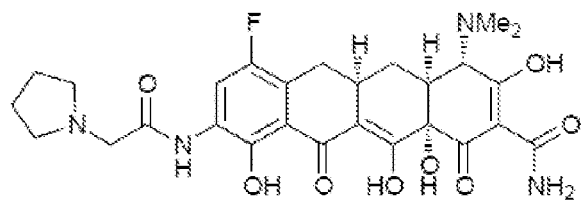
10: eravacycline (TP-434)
b)
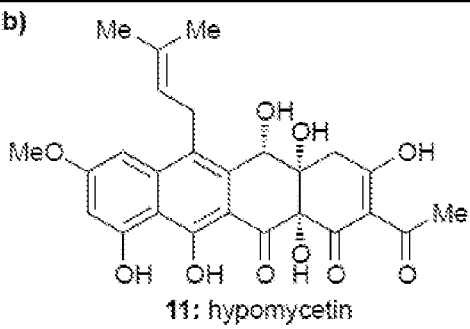
11: hypomycetin
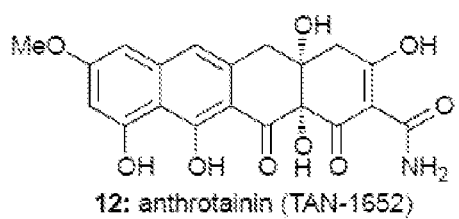
12: anthrotainin (TAN-1552)
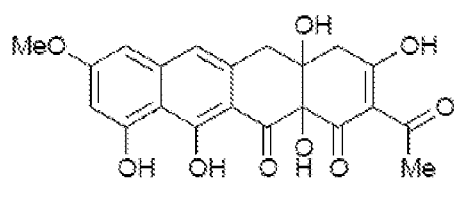
13: TAN-1612
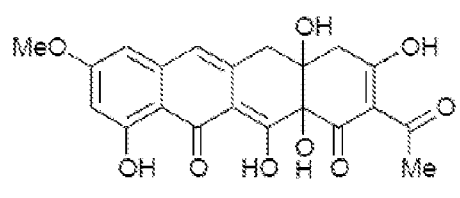
14: BMS-192548
FIGS. 1A & B

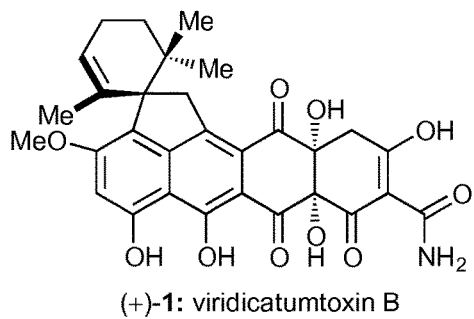
(+)-1: viridicatumtoxin B
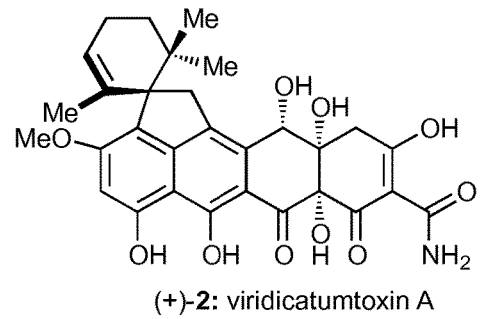
(+)-2: viridicatumtoxin A
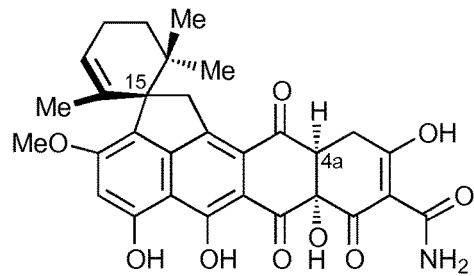
(±)-V2
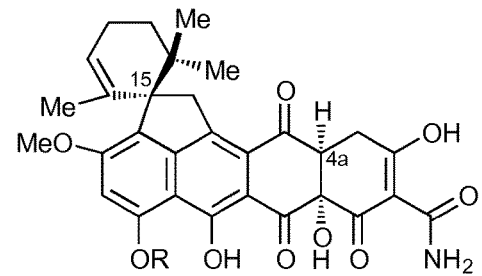
R = H: (±)-V3
R = Me: (±)-V4
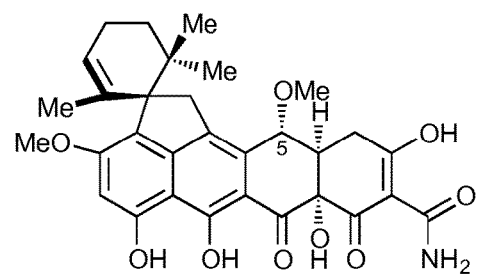
(±)-V5
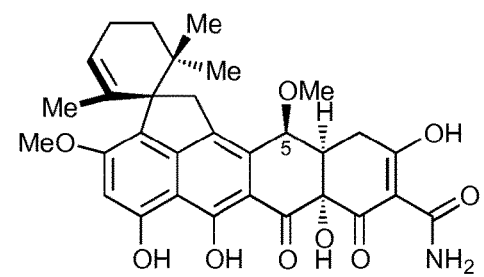
(±)-V6
FIG. 4

US 10,065,924 B2

PREPARATION AND BIOLOGICAL EVALUATION OF VIRIDICATUMTOXIN ANALOGS

This invention was made with government support under Grant Number AI055475 awarded by the National Institutes of Health. The government has certain rights in the invention.

This application claims the benefit of priority to U.S. Provisional Application Ser. No. 62/027,500, filed on Jul. 22, 2014, the entire contents of which are hereby incorporated by reference.

BACKGROUND OF THE INVENTION

1. Field of the Invention

This disclosure relates to the fields of medicine, pharmacology, chemistry, antimicrobial activity, and oncology. In particular, new compounds, compositions, methods of treatment, and methods of synthesis relating to viridicatumtoxin and derivatives thereof are disclosed.

2. Related Art

Since the discovery of chlortetracycline (4; FIG. 1A) in the late 1940's, tetracycline antibiotics such as chlortetracycline (4), oxytetracycline (5), and tetracycline (6) have been commonly prescribed to treat bacterial infections (Duggar, 1948). Throughout the years, as bacterial resistance grew or improved therapeutic properties were needed, additional therapeutic agents including second generation tetracycline derivatives such as minocycline (7) and doxycycline (8) and third generation tetracycline derivatives such as tigecycline (9) and eravacycline (TP-434, 10) have been developed (FIG. 1A) (Tally, et al, 1995; Sutcliffe, et al., 2013; Chopra and Roberts, 2001).

*Penicillium* is a genus of ascomycetous fungi of major importance in the natural environment as well as food and drug production. Members of the genus may be best known for producing penicillin, a molecule that is used as an antibiotic, which kills or stops the growth of certain kinds of bacteria inside the body. According to the *Dictionary of the Fungi* (10th edition, 2008), the widespread genus contains over 300 species. Additionally, the majority of the tetracycline antibiotics have bacterial origins but some tetracycline antibiotics have fungal origins. Tetracycline antibiotics which have fungal origins include viridicatumtoxin B (1), viridicatumtoxin A (2), spirohexaline (3), hypomycetin (11), anthrotainin (TAN-1652, 12), TAN-1612 (13), and BMS-192548 (14) (FIG. 1B & FIG. 2) (Zheng, et al., 2008; Hutchinson, et al., 1973; Inokoshi, et al., 2013; Breinholt, et al., 1997; Wong, et al., 1993; JP 06-40995; Kodukula, et al., 1995; and Shu, et al., 1995). Several tetracycline antibiotics with fungal origins including viridicatumtoxin B (1), viridicatumtoxin A (2), and spirohexaline (3) are also structurally unique from the earlier tetracycline derivatives in the structure also contains a spirobicyclic system (ring system EF) derived from a geranyl subunit (Zheng, et al., 2008; Hutchinson, et al., 1973; Inokoshi, et al., 2013) (FIG. 2).

Without being bound by theory, the proposed biosynthetic pathway to produce the viridicatumtoxin A (2) has been reported and is shown in FIG. 3 (De Jesus, et al., 1982; Chooi, et al., 2010; Chooi, et al., 2012; Chooi, et al., 2013). Due to the biological activity of these compounds and the need for multi-gram quantities of the compounds, a commercially scalable synthesis is needed. Since the discovery of the commercial importance of these molecules for the biological activity, many efforts have been undertaken to synthesize tetracycline derivatives including recent efforts by the Myers (Charest, et al., 2005; Charest, et al., 2005; Brubaker and Myers, 2007; Sun, et al., 2008; Kummer, et al., 2011; Wright and Myers, 2011) and Evans groups (Wzorek, et al., 2012).

In 2008, Kim, et al., isolated viridicatumtoxin B (1) from *Penicillium* sp. FR11 along with viridicatumtoxin A (2). This compound was investigated through NMR spectroscopy and assigned the structure 1'. These compounds have been shown to have potent antibacterial properties in a number of bacterial strains including both gram positive and gram negative bacteria (Kim, et al., 2008). Without being bound by theory, further study and analysis suggests that the viridicatumtoxin's antibacterial properties arise not by binding to the 30S subunit of the ribosome like many tetracycline compounds (e.g., 4-10, FIG. 1A) but by inhibiting UPP synthase, an enzyme associated with bacterial peptidoglycan biosynthesis (Inokoshi, et al., 2013; Koyama, et al., 2013). Furthermore, viridicatumtoxin A (2) shows promising anticancer activity against a selection of cancer cell lines (NIH Results of Viridicatumtoxin A NCI 60 Cell line assay) as well as shows antiviral activity (WO 2009/008906).

As such, new analogs of viridicatumtoxin could provide access to a more efficacious antimicrobial or cancer drug and new methods of synthesis could allow cost effective clinical access to these compound for use in the treatment of microbial infections and as chemotherapeutic agents.

SUMMARY OF THE INVENTION

Thus, in accordance with the present invention, there is provided a compound of the formula:

(I)

wherein: $X_1$ is absent such that atoms 16 and 17 are only connected by the shown single bond, a covalent bond such that a double bond is formed between atoms 16 and 17, —O—, alkanediyl$_{(C \leq 8)}$, or substituted alkanediyl$_{(C \leq 8)}$; $Y_1$, $Y_2$, and $Y_3$ are each independently alkyl$_{(C \leq 12)}$ or substituted alkyl$_{(C \leq 12)}$; $R_1$ is hydrogen, hydroxy, or oxo, provided that when $R_1$ is oxo, the bond between $R_1$ and atom number 5 is a double bond and when the bond between $R_1$ and atom number 5 is a double bond then $R_1$ is oxo, alkoxy$_{(C \leq 8)}$, or substituted alkoxy$_{(C \leq 8)}$; $R_2$ is hydrogen, amino, carboxy, cyano, halo, hydroxy, nitro, or sulfo; alkyl$_{(C \leq 12)}$, alkoxy$_{(C \leq 12)}$, alkylamino$_{(C \leq 12)}$, dialkylamino$_{(C \leq 18)}$, or a substituted version of any of these groups; $R_3$, $R_6$, $R_7$, and $R_{10}$ are each independently selected from: hydrogen, alkyl$_{(C \leq 8)}$, alkenyl$_{(C \leq 8)}$, aryl$_{(C \leq 12)}$, aralkyl$_{(C \leq 12)}$, acyl$_{(C \leq 8)}$, or a substituted version of any of these groups; $R_4$ and $R_5$ are each independently selected from: hydrogen, alkyl$_{(C \leq 8)}$, alkanediyl$_{(C \leq 8)}$-heterocycloalkyl$_{(C \leq 8)}$, alkanediyl$_{(C \leq 8)}$-heteroaryl$_{(C≤8)}$, alkanediyl$_{(C≤8)}$-alkylamino$_{(C≤8)}$, alkanediyl$_{(C≤8)}$-dialkylamino$_{(C≤8)}$, or a substituted version of any of these groups; $R_8$ is hydrogen, alkyl$_{(C≤8)}$, alkenyl$_{(C≤8)}$, aryl$_{(C≤12)}$, aralkyl$_{(C≤12)}$, acyl$_{(C≤8)}$, or a substituted version of any of these groups; or —$X_2$—$R_{11}$, wherein: $X_2$ is alkanediyl$_{(C≤12)}$ or substituted alkanediyl$_{(C≤12)}$; and $R_{11}$ is hydroxy, amino, azido, carboxy, or cyano, alkenyl$_{(C≤6)}$, alkynyl$_{(C≤6)}$, heterocycloalkyl$_{(C≤12)}$, alkylamino$_{(C≤8)}$, dialkylamino$_{(C≤8)}$, alkoxy$_{(C≤8)}$, or a substituted version of any of these groups; or a -linker-biomolecule wherein the biomolecule is a protein, a polypeptide, an amino acid, a cofactor, an imaging agent, an antibody, a fatty acid, a nucleic acid, or a small molecule therapeutic agent; and $R_9$ is hydrogen, amino, carboxy, cyano, halo, hydroxy, nitro, or sulfo; alkyl$_{(C≤12)}$, alkoxy$_{(C≤12)}$, alkylamino$_{(C≤12)}$, dialkylamino$_{(C≤18)}$, amido$_{(C≤12)}$, or a substituted version of any of these groups; or —$NR_{12}C(O)R_{13}$—$NR_{14}R_{15}$; wherein: $R_{12}$ is hydrogen, alkyl$_{(C≤8)}$, or substituted alkyl$_{(C≤8)}$; $R_{13}$ is alkanediyl$_{(C≤8)}$ or substituted alkanediyl$_{(C≤8)}$; and $R_{14}$ and $R_{15}$ are each independently selected from: hydrogen, alkyl$_{(C≤12)}$, aryl$_{(C≤12)}$, aralkyl$_{(C≤12)}$, acyl$_{(C≤12)}$, or a substituted version of any of these groups; or $R_{14}$ and $R_{15}$ are taken together and are alkanediyl$_{(C≤8)}$, alkoxydiyl$_{(C≤8)}$, alkylaminodiyl$_{(C≤8)}$, or a substituted version of any of these groups; or a pharmaceutically acceptable salt or tautomer thereof. In some embodiments, the compound is further defined as:

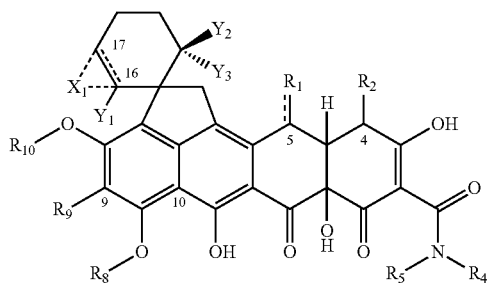

(II)

wherein: $X_1$ is absent such that atoms 16 and 17 are only connected by the shown single bond, a covalent bond such that a double bond is formed between atoms 16 and 17, —O—, alkanediyl$_{(C≤8)}$, or substituted alkanediyl$_{(C≤8)}$; $Y_1$, $Y_2$, and $Y_3$ are each independently alkyl$_{(C≤12)}$ or substituted alkyl$_{(C≤12)}$; $R_1$ is hydrogen, hydroxy, or oxo, provided that when $R_1$ is oxo, the bond between $R_1$ and atom number 5 is a double bond and when the bond between $R_1$ and atom number 5 is a double bond then $R_1$ is oxo, alkoxy$_{(C≤8)}$, or substituted alkoxy$_{(C≤8)}$; $R_2$ is hydrogen, amino, carboxy, cyano, halo, hydroxy, nitro, or sulfo; alkyl$_{(C≤12)}$, alkoxy$_{(C≤12)}$, alkylamino$_{(C≤12)}$, dialkylamino$_{(C≤18)}$, or a substituted version of any of these groups; $R_4$ and $R_5$ are each independently selected from: hydrogen, alkyl$_{(C≤8)}$, alkanediyl$_{(C≤8)}$-heterocycloalkyl$_{(C≤8)}$, alkanediyl$_{(C≤8)}$-heteroaryl$_{(C≤8)}$, alkanediyl$_{(C≤8)}$-alkylamino$_{(C≤8)}$, alkanediyl$_{(C≤8)}$-dialkylamino$_{(C≤8)}$, or a substituted version of any of these groups; $R_8$ is hydrogen, alkyl$_{(C≤8)}$, alkenyl$_{(C≤8)}$, aryl$_{(C≤12)}$, aralkyl$_{(C≤12)}$, acyl$_{(C≤8)}$, or a substituted version of any of these groups; or —$X_2$—$R_{11}$, wherein: $X_2$ is alkanediyl$_{(C≤12)}$ or substituted alkanediyl$_{(C≤12)}$; and $R_{11}$ is hydroxy, amino, azido, carboxy, or cyano, alkenyl$_{(C≤6)}$, alkynyl$_{(C≤6)}$, heterocycloalkyl$_{(C≤12)}$, alkylamino$_{(C≤8)}$, dialkylamino$_{(C≤8)}$, alkoxy$_{(C≤8)}$, or a substituted version of any of these groups; or a -linker-biomolecule wherein the biomolecule is a protein, a polypeptide, an amino acid, a cofactor, an imaging agent, an antibody, a fatty acid, a nucleic acid, or a small molecule therapeutic agent; and $R_9$ is hydrogen, amino, carboxy, cyano, halo, hydroxy, nitro, or sulfo; alkyl$_{(C≤12)}$, alkoxy$_{(C≤12)}$, alkylamino$_{(C≤12)}$, dialkylamino$_{(C≤18)}$, amido$_{(C≤12)}$, or a substituted version of any of these groups; or —$NR_{12}C(O)R_{13}$—$NR_{14}R_{15}$; wherein: $R_{12}$ is hydrogen, alkyl$_{(C≤8)}$, or substituted alkyl$_{(C≤8)}$; $R_{13}$ is alkanediyl$_{(C≤8)}$ or substituted alkanediyl$_{(C≤8)}$; and $R_{14}$ and $R_{15}$ are each independently selected from: hydrogen, alkyl$_{(C≤12)}$, aryl$_{(C≤12)}$, aralkyl$_{(C≤12)}$, acyl$_{(C≤12)}$, or a substituted version of any of these groups; or $R_{14}$ and $R_{15}$ are taken together and are alkanediyl$_{(C≤8)}$, alkoxydiyl$_{(C≤8)}$, alkylaminodiyl$_{(C≤8)}$, or a substituted version of any of these groups; or a pharmaceutically acceptable salt or tautomer thereof. In some embodiments, the compound is further defined as:

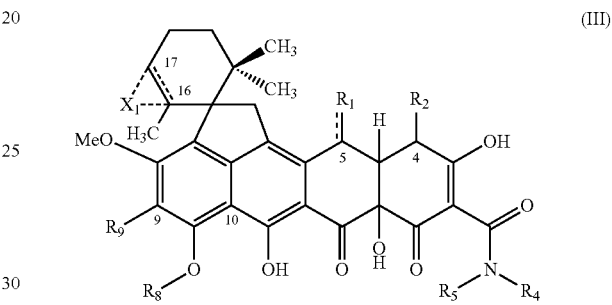

(III)

wherein: $X_1$ is a covalent bond such that a double bond is formed between atoms 16 and 17, —O—, alkanediyl$_{(C≤8)}$, or substituted alkanediyl$_{(C≤8)}$; $R_1$ is hydrogen, hydroxy, or oxo, provided that when $R_1$ is oxo, the bond between $R_1$ and atom number 5 is a double bond and when the bond between $R_1$ and atom number 5 is a double bond then $R_1$ is oxo, alkoxy$_{(C≤8)}$, or substituted alkoxy$_{(C≤8)}$; $R_2$ is hydrogen, amino, carboxy, cyano, halo, hydroxy, nitro, or sulfo; alkyl$_{(C≤12)}$, alkoxy$_{(C≤12)}$, alkylamino$_{(C≤12)}$, dialkylamino$_{(C≤18)}$, or a substituted version of any of these groups; $R_4$ and $R_5$ are each independently selected from: hydrogen, alkyl$_{(C≤8)}$, alkanediyl$_{(C≤8)}$-heterocycloalkyl$_{(C≤8)}$, alkanediyl$_{(C≤8)}$-heteroaryl$_{(C≤8)}$, alkanediyl$_{(C≤8)}$-alkylamino$_{(C≤8)}$, alkanediyl$_{(C≤8)}$-dialkylamino$_{(C≤8)}$, or a substituted version of any of these groups; $R_8$ is hydrogen, alkyl$_{(C≤8)}$, alkenyl$_{(C≤8)}$, aryl$_{(C≤12)}$, aralkyl$_{(C≤12)}$, acyl$_{(C≤8)}$, or a substituted version of any of these groups; or —$X_2$—$R_{11}$, wherein: $X_2$ is alkanediyl$_{(C≤12)}$ or substituted alkanediyl$_{(C≤12)}$; and $R_{11}$ is hydroxy, amino, azido, carboxy, or cyano, alkenyl$_{(C≤6)}$, alkynyl$_{(C≤6)}$, heterocycloalkyl$_{(C≤12)}$, alkylamino$_{(C≤8)}$, dialkylamino$_{(C≤8)}$, alkoxy$_{(C≤8)}$, or a substituted version of any of these groups; or a -linker-biomolecule wherein the biomolecule is a protein, a polypeptide, an amino acid, a cofactor, an imaging agent, an antibody, a fatty acid, a nucleic acid, or a small molecule therapeutic agent; and $R_9$ is hydrogen, amino, carboxy, cyano, halo, hydroxy, nitro, or sulfo; alkyl$_{(C≤12)}$, alkoxy$_{(C≤12)}$, alkylamino$_{(C≤12)}$, dialkylamino$_{(C≤18)}$, amido$_{(C≤12)}$, or a substituted version of any of these groups; or —$NR_{12}C(O)R_{13}$—$NR_{14}R_{15}$; wherein: $R_{12}$ is hydrogen, alkyl$_{(C≤8)}$, or substituted alkyl$_{(C≤8)}$; $R_{13}$ is alkanediyl$_{(C≤8)}$ or substituted alkanediyl$_{(C≤8)}$; and $R_{14}$ and $R_{15}$ are each independently selected from: hydrogen, alkyl$_{(C≤12)}$, aryl$_{(C≤12)}$, aralkyl$_{(C≤12)}$, acyl$_{(C≤12)}$, or a substituted version of any of these groups; or $R_{14}$ and $R_{15}$ are taken together and are alkanediyl$_{(C≤8)}$, alkoxydiyl$_{(C≤8)}$, alkylaminodiyl$_{(C≤8)}$, or a substituted version of any of these groups; or a pharmaceutically acceptable salt or tautomer thereof. In some embodiments, the compound is further defined as:

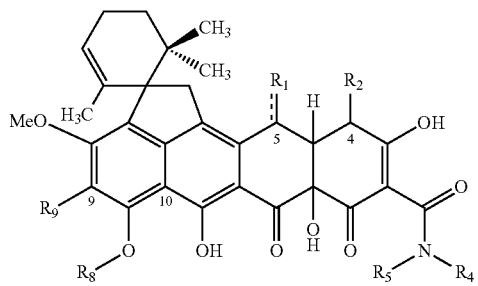

(IV)

wherein: $R_1$ is hydroxy, or oxo, provided that when $R_1$ is oxo, the bond between $R_1$ and atom number 5 is a double bond and when the bond between $R_1$ and atom number 5 is a double bond then $R_1$ is oxo, alkoxy$_{(C\leq 8)}$, or substituted alkoxy$_{(C\leq 8)}$; $R_2$ is hydrogen, amino, carboxy, cyano, halo, hydroxy, nitro, or sulfo; alkyl$_{(C\leq 12)}$, alkoxy$_{(C\leq 12)}$, alkylamino$_{(C\leq 12)}$, dialkylamino$_{(C\leq 18)}$, or a substituted version of any of these groups; $R_4$ and $R_5$ are each independently selected from: hydrogen, alkyl$_{(C\leq 8)}$, alkanediyl$_{(C\leq 8)}$-heterocycloalkyl$_{(C\leq 8)}$, alkanediyl$_{(C\leq 8)}$-heteroaryl$_{(C\leq 8)}$, alkanediyl$_{(C\leq 8)}$-alkylamino$_{(C\leq 8)}$, alkanediyl$_{(C\leq 8)}$-dialkylamino$_{(C\leq 8)}$, or a substituted version of any of these groups; $R_8$ is hydrogen, alkyl$_{(C\leq 8)}$, alkenyl$_{(C\leq 8)}$, aryl$_{(C\leq 12)}$, aralkyl$_{(C\leq 12)}$, acyl$_{(C\leq 8)}$, or a substituted version of any of these groups; or —$X_2$—$R_{11}$, wherein: $X_2$ is alkanediyl$_{(C\leq 12)}$ or substituted alkanediyl$_{(C\leq 12)}$; and $R_{11}$ is hydroxy, amino, azido, carboxy, or cyano, alkenyl$_{(C\leq 6)}$, alkynyl$_{(C\leq 6)}$, heterocycloalkyl$_{(C\leq 12)}$, alkylamino$_{(C\leq 8)}$, dialkylamino$_{(C\leq 8)}$, alkoxy$_{(C\leq 8)}$, or a substituted version of any of these groups; or a -linker-biomolecule wherein the biomolecule is a protein, a polypeptide, an amino acid, a cofactor, an imaging agent, an antibody, a fatty acid, a nucleic acid, or a small molecule therapeutic agent; and $R_9$ is hydrogen, amino, carboxy, cyano, halo, hydroxy, nitro, or sulfo; alkyl$_{(C\leq 12)}$, alkoxy$_{(C\leq 12)}$, alkylamino$_{(C\leq 12)}$, dialkylamino$_{(C\leq 18)}$, amido$_{(C\leq 12)}$, or a substituted version of any of these groups; or —$NR_{12}C(O)R_{13}$—$NR_{14}R_{15}$; wherein: $R_{12}$ is hydrogen, alkyl$_{(C\leq 8)}$, or substituted alkyl$_{(C\leq 8)}$; $R_{13}$ is alkanediyl$_{(C\leq 8)}$ or substituted alkanediyl$_{(C\leq 8)}$; and $R_{14}$ and $R_{15}$ are each independently selected from: hydrogen, alkyl$_{(C\leq 12)}$, aryl$_{(C\leq 12)}$, aralkyl$_{(C\leq 12)}$, acyl$_{(C\leq 12)}$, or a substituted version of any of these groups; or $R_{14}$ and $R_{15}$ are taken together and are alkanediyl$_{(C\leq 8)}$, alkoxydiyl$_{(C\leq 8)}$, alkylaminodiyl$_{(C\leq 8)}$, or a substituted version of any of these groups; or a pharmaceutically acceptable salt or tautomer thereof. In some embodiments, the compound is further defined as:

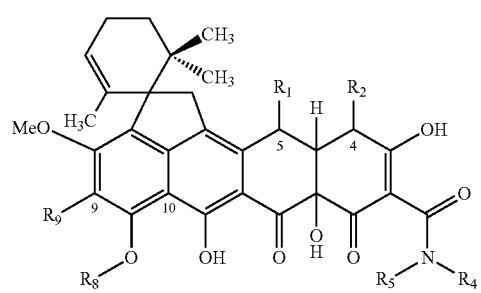

(V)

wherein: $R_1$ is hydroxy, alkoxy$_{(C\leq 8)}$, or substituted alkoxy$_{(C\leq 8)}$; $R_2$ is hydrogen, amino, carboxy, cyano, halo, hydroxy, nitro, or sulfo; alkyl$_{(C\leq 12)}$, alkoxy$_{(C\leq 12)}$, alkylamino$_{(C\leq 12)}$, dialkylamino$_{(C\leq 18)}$, or a substituted version of any of these groups; $R_4$ is hydrogen, alkyl$_{(C\leq 8)}$, or substituted alkyl$_{(C\leq 8)}$, $R_5$ is hydrogen, alkyl$_{(C\leq 8)}$, alkanediyl$_{(C\leq 8)}$-heterocycloalkyl$_{(C\leq 8)}$, alkanediyl$_{(C\leq 8)}$-heteroaryl$_{(C\leq 8)}$, alkanediyl$_{(C\leq 8)}$-alkylamino$_{(C\leq 8)}$, alkanediyl$_{(C\leq 8)}$-dialkylamino$_{(C\leq 8)}$, or a substituted version of any of these groups; $R_8$ is hydrogen, alkyl$_{(C\leq 8)}$, alkenyl$_{(C\leq 8)}$, aryl$_{(C\leq 12)}$, aralkyl$_{(C\leq 12)}$, acyl$_{(C\leq 8)}$, or a substituted version of any of these groups; or —$X_2$—$R_{11}$, wherein: $X_2$ is alkanediyl$_{(C\leq 12)}$ or substituted alkanediyl$_{(C\leq 12)}$; and $R_{11}$ is hydroxy, amino, azido, carboxy, or cyano, alkenyl$_{(C\leq 6)}$, alkynyl$_{(C\leq 6)}$, heterocycloalkyl$_{(C\leq 12)}$, alkylamino$_{(C\leq 8)}$, dialkylamino$_{(C\leq 8)}$, alkoxy$_{(C\leq 8)}$, or a substituted version of any of these groups; or a -linker-biomolecule wherein: the linker is alkanediyl$_{(C\leq 12)}$, alkenediyl$_{(C\leq 12)}$, arenediyl$_{(C\leq 12)}$, heteroarenediyl$_{(C\leq 12)}$, heterocycloalkanediyl$_{(C\leq 12)}$ or a substi-

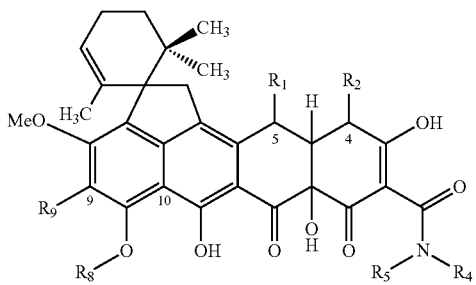

(V)

tuted version of any of these groups; and the biomolecule is a protein, a polypeptide, an antibody, an imaging agent, or a small molecule therapeutic agent; and $R_9$ is hydrogen, amino, carboxy, cyano, halo, hydroxy, nitro, or sulfo; alkyl$_{(C\leq12)}$, alkoxy$_{(C\leq12)}$, alkylamino$_{(C\leq12)}$, dialkylamino$_{(C\leq18)}$, amido$_{(C\leq12)}$, or a substituted version of any of these groups; or —NR$_{12}$C(O)R$_{13}$—NR$_{14}$R$_{15}$; wherein: $R_{12}$ is hydrogen, alkyl$_{(C\leq8)}$, or substituted alkyl$_{(C\leq8)}$; $R_{13}$ is alkanediyl$_{(C\leq8)}$ or substituted alkanediyl$_{(C\leq8)}$; and $R_{14}$ and $R_{15}$ are each independently selected from: hydrogen, alkyl$_{(C\leq12)}$, aryl$_{(C\leq12)}$, aralkyl$_{(C\leq12)}$, acyl$_{(C\leq12)}$, or a substituted version of any of these groups; or $R_{14}$ and $R_{15}$ are taken together and are alkanediyl$_{(C\leq8)}$, alkoxydiyl$_{(C\leq8)}$, alkylaminodiyl$_{(C\leq8)}$, or a substituted version of any of these groups; or a pharmaceutically acceptable salt or tautomer thereof. In some embodiments, the compound is further defined as:

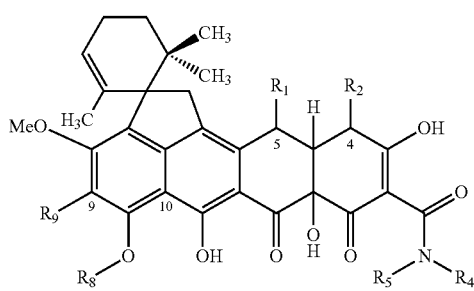

(V)

wherein: $R_1$ is hydroxy, alkoxy$_{(C\leq8)}$, or substituted alkoxy$_{(C\leq8)}$; $R_2$ is hydrogen, amino, carboxy, cyano, halo, hydroxy, nitro, or sulfo; alkyl$_{(C\leq12)}$, alkoxy$_{(C\leq12)}$, alkylamino$_{(C\leq12)}$, dialkylamino$_{(C\leq18)}$, or a substituted version of any of these groups; $R_4$ is hydrogen, alkyl$_{(C\leq8)}$, or substituted alkyl$_{(C\leq8)}$, $R_5$ is hydrogen, alkyl$_{(C\leq8)}$, alkanediyl$_{(C\leq8)}$-heterocycloalkyl$_{(C\leq8)}$, alkanediyl$_{(C\leq8)}$-heteroaryl$_{(C\leq8)}$, alkanediyl$_{(C\leq8)}$-alkylamino$_{(C\leq8)}$, alkanediyl$_{(C\leq8)}$-dialkylamino$_{(C\leq8)}$, or a substituted version of any of these groups; $R_8$ is hydrogen, alkyl$_{(C\leq8)}$, substituted alkyl$_{(C\leq8)}$, or —X$_2$—R$_{11}$, wherein: $X_2$ is alkanediyl$_{(C\leq12)}$ or substituted alkanediyl$_{(C\leq12)}$; and $R_{11}$ is hydroxy, amino, azido, carboxy, or cyano, alkenyl$_{(C\leq6)}$, alkynyl$_{(C\leq6)}$, heterocycloalkyl$_{(C\leq12)}$, alkylamino$_{(C\leq8)}$, dialkylamino$_{(C\leq8)}$, alkoxy$_{(C\leq8)}$, or a substituted version of any of these groups; or a -linker-biomolecule wherein: the linker is alkanediyl$_{(C\leq12)}$, alkenediyl$_{(C\leq12)}$, arenediyl$_{(C\leq12)}$, heteroarenediyl$_{(C\leq12)}$, heterocycloalkanediyl$_{(C\leq12)}$ or a substituted version of any of these groups; and the biomolecule is an antibody, an imaging agent, a protein, or a small molecule therapeutic agent; $R_9$ is hydrogen, amino, carboxy, cyano, halo, hydroxy, nitro, or sulfo; alkyl$_{(C\leq12)}$, alkoxy$_{(C\leq12)}$, alkylamino$_{(C\leq12)}$, dialkylamino$_{(C\leq18)}$, amido$_{(C\leq12)}$, or a substituted version of any of these groups; or —NR$_{12}$C(O)R$_{13}$—NR$_{14}$R$_{15}$; wherein: $R_{12}$ is hydrogen, alkyl$_{(C\leq8)}$, or substituted alkyl$_{(C\leq8)}$; $R_{13}$ is alkanediyl$_{(C\leq8)}$ or substituted alkanediyl$_{(C\leq8)}$; and $R_{14}$ and $R_{15}$ are each independently selected from: hydrogen, alkyl$_{(C\leq12)}$, aryl$_{(C\leq12)}$, aralkyl$_{(C\leq12)}$, acyl$_{(C\leq12)}$, or a substituted version of any of these groups; or $R_{14}$ and $R_{15}$ are taken together and are alkanediyl$_{(C\leq8)}$, alkoxydiyl$_{(C\leq8)}$, alkylaminodiyl$_{(C\leq8)}$, or a substituted version of any of these groups; or a pharmaceutically acceptable salt or tautomer thereof. In some embodiments, the compound is further defined as:

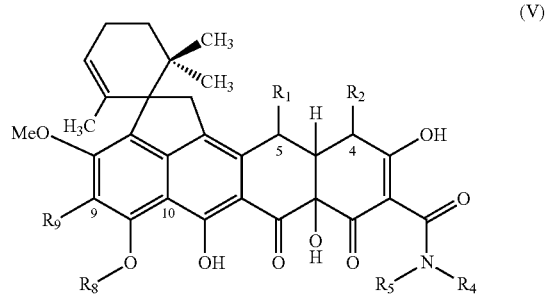

(V)

wherein: $R_1$ is hydroxy, alkoxy$_{(C\leq8)}$, or substituted alkoxy$_{(C\leq8)}$; $R_2$ is hydrogen, amino, carboxy, cyano, halo, hydroxy, nitro, or sulfo; alkyl$_{(C\leq12)}$, alkoxy$_{(C\leq12)}$, alkylamino$_{(C\leq12)}$, dialkylamino$_{(C\leq18)}$, or a substituted version of any of these groups; $R_4$ is hydrogen, alkyl$_{(C\leq8)}$, or substituted alkyl$_{(C\leq8)}$, $R_5$ is hydrogen, alkyl$_{(C\leq8)}$, alkanediyl$_{(C\leq8)}$-heterocycloalkyl$_{(C\leq8)}$, alkanediyl$_{(C\leq8)}$-heteroaryl$_{(C\leq8)}$, alkanediyl$_{(C\leq8)}$-alkylamino$_{(C\leq8)}$, alkanediyl$_{(C\leq8)}$-dialkylamino$_{(C\leq8)}$, or a substituted version of any of these groups; $R_8$ is hydrogen or a -linker-biomolecule; wherein: the linker is alkanediyl$_{(C\leq12)}$, alkenediyl$_{(C\leq12)}$, arenediyl$_{(C\leq12)}$, heteroarenediyl$_{(C\leq12)}$, or heterocycloalkanediyl$_{(C\leq12)}$; and the biomolecule is an antibody; and $R_9$ is hydrogen, amino, carboxy, cyano, halo, hydroxy, nitro, or sulfo; alkyl$_{(C\leq12)}$, alkoxy$_{(C\leq12)}$, alkylamino$_{(C\leq12)}$, dialkylamino$_{(C\leq18)}$, amido$_{(C\leq12)}$, or a substituted version of any of these groups; or —NR$_{12}$C(O)R$_{13}$—NR$_{14}$R$_{15}$; wherein: $R_{12}$ is hydrogen, alkyl$_{(C\leq8)}$, or substituted alkyl$_{(C\leq8)}$; $R_{13}$ is alkanediyl$_{(C\leq8)}$ or substituted alkanediyl$_{(C\leq8)}$; and $R_{14}$ and $R_{15}$ are each independently selected from: hydrogen, alkyl$_{(C\leq12)}$, aryl$_{(C\leq12)}$, aralkyl$_{(C\leq12)}$, acyl$_{(C\leq12)}$, or a substituted version of any of these groups; or $R_{14}$ and $R_{15}$ are taken together and are alkanediyl$_{(C\leq8)}$, alkoxydiyl$_{(C\leq8)}$, alkylaminodiyl$_{(C\leq8)}$, or a substituted version of any of these groups; or a pharmaceutically acceptable salt or tautomer thereof. In some embodiments, the compound is further defined as:

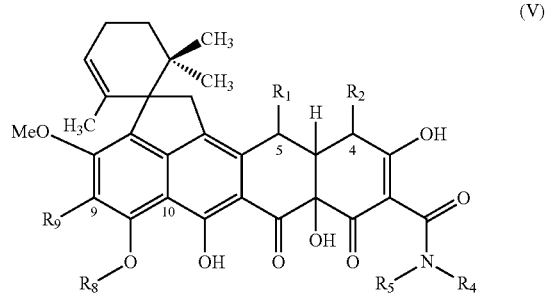

(V)

wherein: $R_1$ is hydroxy, alkoxy$_{(C\leq8)}$, or substituted alkoxy$_{(C\leq8)}$; $R_2$ is hydrogen, amino, halo, or hydroxy; alkylamino$_{(C\leq12)}$, dialkylamino$_{(C\leq18)}$, or a substituted version of any of these groups; $R_4$ is hydrogen, alkyl$_{(C\leq8)}$, or substituted alkyl$_{(C\leq8)}$, $R_5$ is hydrogen, alkyl$_{(C\leq8)}$, alkanediyl$_{(C\leq8)}$-heterocycloalkyl$_{(C\leq8)}$, alkanediyl$_{(C\leq8)}$-heteroaryl$_{(C\leq8)}$, alkanediyl$_{(C\leq8)}$-alkylamino$_{(C\leq8)}$, alkanediyl$_{(C\leq8)}$-dialkylamino$_{(C\leq8)}$, or a substituted version of any of these groups; $R_8$ is hydrogen, alkyl$_{(C\leq8)}$, alkenyl$_{(C\leq8)}$, aryl$_{(C\leq12)}$, aralkyl$_{(C\leq12)}$, acyl$_{(C\leq8)}$, or a substituted version of any of these groups; or —X$_2$—R$_{11}$, wherein: $X_2$ is alkanediyl$_{(C\leq12)}$ or substituted alkanediyl$_{(C\leq12)}$; and $R_{11}$ is hydroxy, amino, azido, carboxy, or cyano, alkenyl$_{(C≤6)}$, alkynyl$_{(C≤6)}$, heterocycloalkyl$_{(C≤12)}$, alkylamino$_{(C≤8)}$, dialkylamino$_{(C≤8)}$, alkoxy$_{(C≤8)}$, or a substituted version of any of these groups; or a -linker-biomolecule; and R$_9$ is hydrogen, amino, carboxy, cyano, halo, hydroxy, nitro, or sulfo; alkyl$_{(C≤12)}$, alkoxy$_{(C≤12)}$, alkylamino$_{(C≤12)}$, dialkylamino$_{(C≤18)}$, amido$_{(C≤12)}$, or a substituted version of any of these groups; or —NR$_{12}$C(O)R$_{13}$—NR$_{14}$R$_{15}$; wherein: R$_{12}$ is hydrogen, alkyl$_{(C≤8)}$, or substituted alkyl$_{(C≤8)}$; R$_{13}$ is alkanediyl$_{(C≤8)}$ or substituted alkanediyl$_{(C≤8)}$; and R$_{14}$ and R$_{15}$ are each independently selected from: hydrogen, alkyl$_{(C≤12)}$, aryl$_{(C≤12)}$, aralkyl$_{(C≤12)}$, acyl$_{(C≤12)}$, or a substituted version of any of these groups; or R$_{14}$ and R$_{15}$ are taken together and are alkanediyl$_{(C≤8)}$, alkoxydiyl$_{(C≤8)}$, alkylaminodiyl$_{(C≤8)}$, or a substituted version of any of these groups; or a pharmaceutically acceptable salt or tautomer thereof. In some embodiments, the compound further defined as:

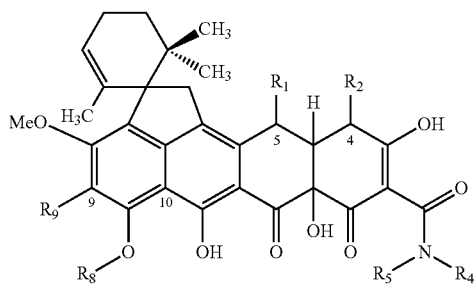

(V)

wherein: R$_1$ is hydroxy, alkoxy$_{(C≤8)}$, or substituted alkoxy$_{(C≤8)}$; R$_2$ is hydrogen, amino, halo, or hydroxy; alkylamino$_{(C≤12)}$, dialkylamino$_{(C≤18)}$, or a substituted version of any of these groups; R$_4$ is hydrogen, alkyl$_{(C≤8)}$, or substituted alkyl$_{(C≤8)}$, R$_5$ is hydrogen, alkyl$_{(C≤8)}$, alkanediyl$_{(C≤8)}$-heterocycloalkyl$_{(C≤8)}$, alkanediyl$_{(C≤8)}$-heteroaryl$_{(C≤8)}$, alkanediyl$_{(C≤8)}$-alkylamino$_{(C≤8)}$, alkanediyl$_{(C≤8)}$-dialkylamino$_{(C≤8)}$, or a substituted version of any of these groups; R$_8$ is hydrogen, alkyl$_{(C≤8)}$, alkenyl$_{(C≤8)}$, aryl$_{(C≤12)}$, aralkyl$_{(C≤12)}$, acyl$_{(C≤8)}$, or a substituted version of any of these groups; or —X$_2$—R$_{11}$, wherein: X$_2$ is alkanediyl$_{(C≤12)}$ or substituted alkanediyl$_{(C≤12)}$; and R$_{11}$ is hydroxy, amino, azido, carboxy, or cyano, alkenyl$_{(C≤6)}$, alkynyl$_{(C≤6)}$, heterocycloalkyl$_{(C≤12)}$, alkylamino$_{(C≤8)}$, dialkylamino$_{(C≤8)}$, alkoxy$_{(C≤8)}$, or a substituted version of any of these groups; or a -linker-biomolecule; and R$_9$ is —NR$_{12}$C(O)R$_{13}$—NR$_{14}$R$_{15}$; wherein: R$_{12}$ is hydrogen, alkyl$_{(C≤8)}$, or substituted alkyl$_{(C≤8)}$; R$_{13}$ is alkanediyl$_{(C≤8)}$ or substituted alkanediyl$_{(C≤8)}$; and R$_{14}$ and R$_{15}$ are each independently selected from: hydrogen, alkyl$_{(C≤12)}$, aryl$_{(C≤12)}$, aralkyl$_{(C≤12)}$, acyl$_{(C≤12)}$, or a substituted version of any of these groups; or a pharmaceutically acceptable salt or tautomer thereof. In some embodiments, R$_1$ is alkoxy$_{(C≤8)}$ or substituted alkoxy$_{(C≤8)}$. In some embodiments, R$_1$ is alkoxy$_{(C≤6)}$. In some embodiments, R$_1$ is methoxy. In other embodiments, R$_1$ is oxo. In some embodiments, R$_2$ is hydrogen. In other embodiments, R$_2$ is halo. In some embodiments, R$_2$ is fluoro, chloro, bromo, or iodo. In other embodiments, R$_2$ is hydroxy. In other embodiments, R$_2$ is amino. In other embodiments, R$_2$ is dialkylamino$_{(C≤12)}$ or substituted dialkylamino$_{(C≤12)}$. In some embodiments, R$_2$ is dialkylamino$_{(C≤12)}$. In some embodiments, R$_2$ is dimethylamino or (2-aminoethyl)methylamino. In some embodiments, R$_4$ is hydrogen. In some embodiments, R$_5$ is hydrogen. In other embodiments, R$_5$ is alkanediyl$_{(C≤8)}$-heterocycloalkyl$_{(C≤8)}$. In some embodiments, R$_5$ is —CH$_2$CH$_2$N(CH$_2$)$_4$. In other embodiments, R$_5$ is alkanediyl$_{(C≤8)}$-alkylamino$_{(C≤8)}$. In some embodiments, R$_5$ is —(CH$_2$)$_2$NH(CH$_2$)$_4$CH(NH$_2$)CO$_2$H. In some embodiments, R$_8$ is hydrogen. In other embodiments, R$_8$ is —X$_2$—R$_{11}$. In some embodiments, X$_2$ is alkanediyl$_{(C≤6)}$ or substituted alkanediyl$_{(C≤6)}$. In some embodiments, X$_2$ is alkanediyl$_{(C≤6)}$. In some embodiments, X$_2$ is —CH$_2$CH$_2$CH$_2$— or —CH$_2$CH$_2$—. In some embodiments, R$_{11}$ is amino. In other embodiments, R$_{11}$ is heterocycloalkyl$_{(C≤12)}$, or substituted heterocycloalkyl$_{(C≤12)}$. In some embodiments, R$_{11}$ is 4-N-methyl-piperazinyl. In other embodiments, R$_8$ is a -linker-biomolecule. In some embodiments, the linker is alkanediyl$_{(C≤12)}$, alkenediyl$_{(C≤12)}$, arenediyl$_{(C≤12)}$, heteroarenediyl$_{(C≤12)}$, heterocycloalkanediyl$_{(C≤12)}$ or a substituted version of any of these groups. In some embodiments, the biomolecule is an antibody, a protein, or a small molecule therapeutic agent. In some embodiments, the biomolecule is an antibody. In some embodi-

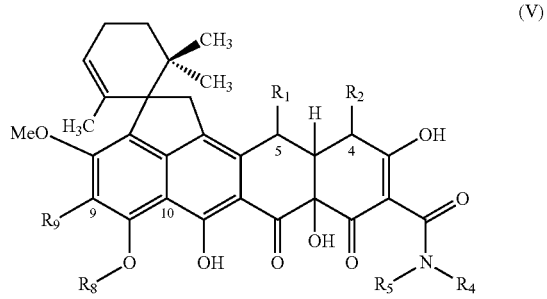

(V)

ments, $R_9$ is hydrogen. In other embodiments, $R_9$ is halo. In some embodiments, $R_9$ is fluoro or iodo. In other embodiments, $R_9$ is amido$_{(C\leq12)}$ or substituted amido$_{(C\leq12)}$. In some embodiments, $R_9$ is —NHC(O)CH$_2$NH$_2$. In other embodiments, $R_9$ is —NR$_{12}$C(O)R$_{13}$—NR$_{14}$R$_{15}$. In some embodiments, $R_{12}$ is hydrogen. In other embodiments, $R_{12}$ is alkyl$_{(C\leq6)}$ or substituted alkyl$_{(C\leq6)}$. In some embodiments, $R_{13}$ is alkanediyl$_{(C\leq8)}$. In some embodiments, $R_{13}$ is —CH$_2$—. In some embodiments, $R_{14}$ is alkyl$_{(C\leq12)}$ or substituted alkyl$_{(C\leq12)}$. In some embodiments, $R_{14}$ is t-butyl. In some embodiments, $R_{15}$ is hydrogen. In some embodiments, the compound is further defined as:

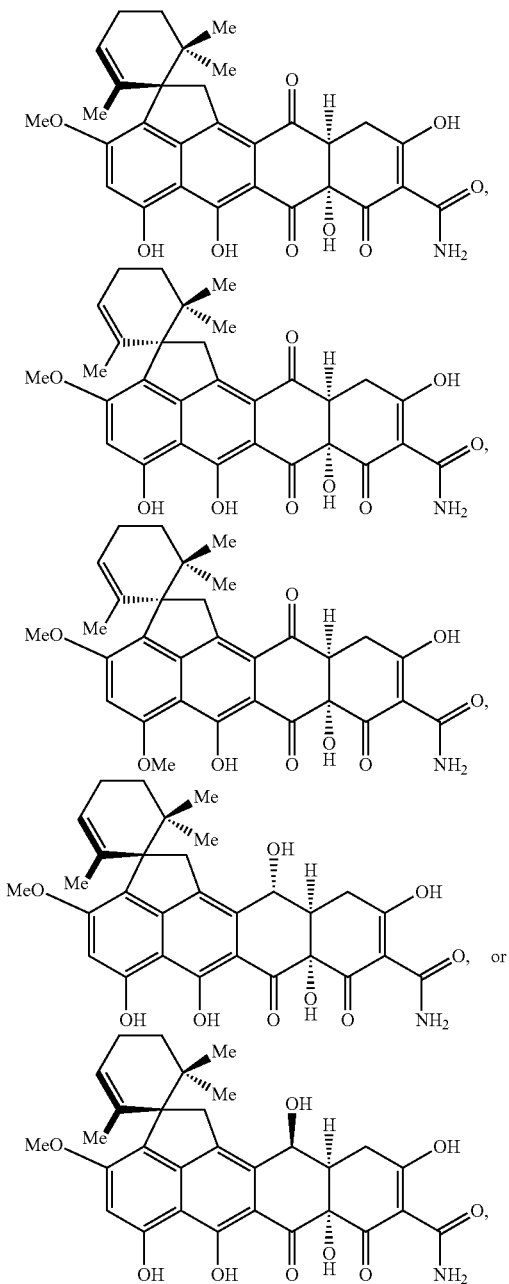

or a pharmaceutically acceptable salt, tautomer, or optical isomer thereof.

In another aspect, the present disclosure provides a pharmaceutical composition comprising a compound as described herein and an excipient. In some embodiments, the composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in crémes, in lipid compositions, via a catheter, via a lavage, via continuous infusion, via infusion, via inhalation, via injection, via local delivery, or via localized perfusion. In some embodiments, the composition is formulated for administration: orally, intravenously, or topically.

In yet another aspect, the present disclosure provides a method of treating a disease or disorder comprising administering a pharmaceutically effective amount of a compound or composition as described herein. In some embodiments, the disease or disorder is a microbial infection. In some embodiments, the microbial infection is a bacterial infection. In some embodiments, the infection is by a gram positive or gram negative bacteria. In some embodiments, the disease is a bacteria infection by *Enterococcus faecalis, Enterococcus faecium, Staphylococcus aureus, Acinetobacter baumannii, Escherichia coli, Acinetobacter calcoaceticus, Staphycococcus epidermidis, Pseudomonas aeruginosa, Klebsiella aerogenes, Candida albicans, Salmonella typhinurium, Streptococcus pneumoniae, Micrococcus luteus, Bacillus cerues,* or *Bacillus subtilis*. In some embodiments, the disease is a bacteria infection by *Staphylococcus aureus* 503, *Staphylococcus aureus* 209, *Staphylococcus aureus* RN420, Methicillin-resistant *Staphylococcus aureus* CCARM 3167, Methicillin-resistant *Staphylococcus aureus* 371, Methicillin-resistant *Staphylococcus aureus* CCARM 3506, quinolone-resistant *Staphylococcus aureus* CCARM 3505, quinolone-resistant *Staphylococcus aureus* CCARM 3519, *Bacillus subtilis* KCTC 1021, *Bacillus cerues* KCTC 1661, *Micrococcus luteus* KCTC 1056, *Streptococcus pneumoniae* KCTC 3932, *Streptococcus pneumoniae* KCTC 5412, *Enterococcus faecium* 501, *Enterococcus faecium* KCTC 3122, *Enterococcus faecalis* 5613, *Enterococcus faecalis* KCTC 5191, *Enterococcus faecalis* KCTC 3511, *Staphycococcus epidermidis* KCTC 3958, *Salmonella typhinurium* KCTC 1926, *Acinetobacter calcoaceticus* KCTC 2357, *Escherichia coli* CCARM 1358, *Escherichia coli* KCTC 1682, *Pseudomonas aeruginosa* KCTC 2004, *Pseudomonas aeruginosa* KCTC 2742, *Klebsiella aerogenes* KCTC 2619, *Acinetobacter baumannii* AB210, or *Candida albicans* KCTC 7535. In some embodiments, the bacteria is a drug-resistant bacteria. In some embodiments, the method further comprises administering a second therapeutic agent. In some embodiments, the second therapeutic agent is an antibiotic. In some embodiments, the second therapeutic agent is a tetracycline antibiotic. In some embodiments, the second therapeutic agent is viridicatumtoxin A, viridicatumtoxin B, vancomycin, tetracycline, spirohexaline, minocycline, tigecycline, doxycycline, a β-lactam antibiotic, an aminoglycoside antibiotic, a sulfonamide antibiotic, a macrolide antibiotic, a glycopeptide antibioitic, an ansamycin antibiotic, an oxazolidinone antibiotic, a quinolone antibiotic, a streptogramin antibiotic, or a lipopeptide antibiotic. In other embodiments, the microbial infection is a viral infection. In some embodiments, the virus is a poxvirus. In some embodiments, the poxvirus is variola virus, vaccinia virus, or molluscum contagiosum. In some embodiments, the method further comprises administering a second therapeutic agent. In some embodiments, the second therapeutic agent is an interferon or antiviral compound. In other embodiments, the disease or disorder is cancer. In some embodiments, the cancer is a carcinoma, sarcoma, lymphoma, leukemia, melanoma, mesothelioma, multiple myeloma, or seminoma. In some embodiments, the cancer is of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the method further comprises administering a second therapeutic agent. In some embodiments, the second therapeutic agent is a second chemotherapeutic agent, radiotherapy, immunotherapy, or surgery.

In another aspect, the present disclosure provides a method of inhibiting the activity of a bacterial ribosome for the treatment of a disease or disorder comprising administering a compound or composition according to any one of the claims. In still another aspect, the present disclosure provides a method of inhibiting the activity of a bacterial UPP synthase for the treatment of a disease or disorder comprising administering a compound or composition as described herein In yet another aspect, the present disclosure provides a method of preparing a compound of the formula:

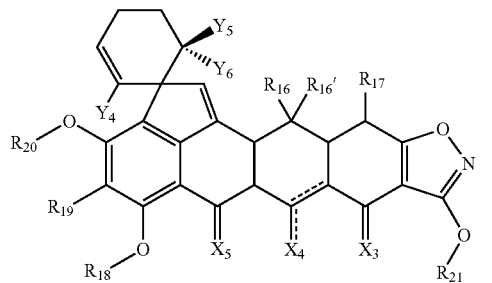

(VI)

wherein: $Y_4$, $Y_5$, and $Y_6$ are each independently hydrogen, alkyl$_{(C \leq 8)}$ or substituted alky$_{(C \leq 8)}$; $R_{16}$ and $R_{16}'$ are each independently hydrogen, alkoxy$_{(C \leq 8)}$, aralkoxy$_{(C \leq 12)}$, substituted alkoxy$_{(C \leq 8)}$, or substituted aralkoxy$_{(C \leq 12)}$; or $R_{16}$ and $R_{16}'$ are taken together and are alkoxydiyl$_{(C \leq 12)}$; $R_{17}$ is hydrogen, amino, carboxy, cyano, halo, hydroxy, nitro, or sulfo; alkyl$_{(C \leq 12)}$, alkoxy$_{(C \leq 12)}$, alkylamino$_{(C \leq 12)}$, dialkylamino$_{(C \leq 18)}$, or a substituted version of any of these groups; or —C(O)OCH$_2$CH$_2$Si(CH$_3$)$_3$; $X_3$ is O, NH, S, or CH$_2$; $X_4$ is hydroxy, amino, mercapto, O, NH, or S provided that when $X_4$ is O, NH, or S, the bond to which the atom is attached is a double bond and provide that when the bond to which the atom is attached is a double bond, then $X_4$ is O, NH, or S; $X_5$ is O, NH, or S; $R_{18}$ is hydrogen, alkyl$_{(C \leq 8)}$, alkenyl$_{(C \leq 8)}$, aryl$_{(C \leq 12)}$, aralkyl$_{(C \leq 12)}$, acyl$_{(C \leq 8)}$, or a substituted version of any of these groups; or —X$_2$—R$_{11}$, wherein: $X_2$ is alkanediyl$_{(C \leq 12)}$ or substituted alkanediyl$_{(C \leq 12)}$; and $R_{11}$ is hydroxy, amino, azido, carboxy, or cyano, alkenyl$_{(C \leq 6)}$, alkynyl$_{(C \leq 6)}$, heterocycloalkyl$_{(C \leq 12)}$, alkylamino$_{(C \leq 8)}$, dialkylamino$_{(C \leq 8)}$, alkoxy$_{(C \leq 8)}$, or a substituted version of any of these groups; $R_{19}$ is hydrogen, amino, carboxy, cyano, halo, hydroxy, nitro, or sulfo; alkyl$_{(C \leq 12)}$, alkoxy$_{(C \leq 12)}$, alkylamino$_{(C \leq 12)}$, dialkylamino$_{(C \leq 18)}$, amido$_{(C \leq 12)}$, or a substituted version of any of these groups; or —NR$_{12}$C(O)R$_{13}$—NR$_{14}$R$_{15}$; wherein: $R_{12}$ is hydrogen, alkyl$_{(C \leq 8)}$, or substituted alkyl$_{(C \leq 8)}$; $R_{13}$ is alkanediyl$_{(C \leq 8)}$ or substituted alkanediyl$_{(C \leq 8)}$; and $R_{14}$ and $R_{15}$ are each independently selected from: hydrogen, alkyl$_{(C \leq 12)}$, aryl$_{(C \leq 12)}$, aralkyl$_{(C \leq 12)}$, acyl$_{(C \leq 12)}$, or a substituted version of any of these groups; or $R_{14}$ and $R_{15}$ are taken together and are alkanediyl$_{(C \leq 8)}$, alkoxydiyl$_{(C \leq 8)}$, alkylaminodiyl$_{(C \leq 8)}$, or a substituted version of any of these groups; and $R_{20}$ and $R_{21}$ are each independently hydrogen, alkyl$_{(C \leq 8)}$, alkenyl$_{(C \leq 8)}$, aryl$_{(C \leq 12)}$, aralkyl$_{(C \leq 12)}$, acyl$_{(C \leq 8)}$, or a substituted version of any of these groups; or a salt, tautomer, or optical isomer thereof; comprising reacting a compound of the formula:

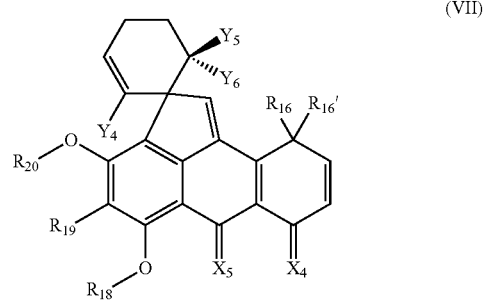

(VII)

wherein: $Y_4$, $Y_5$, $Y_6$, $R_{16}$, $R_{16}'$, $X_5$, $R_{18}$, $R_{19}$, and $R_{20}$ are as defined above; and $X_4$ is O, NH, or S; with a compound of the formula:

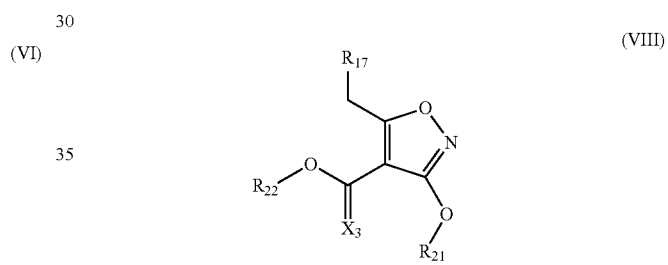

(VIII)

wherein: $X_3$ and $R_{17}$ are as defined above; $R_{21}$ is hydrogen, alkyl$_{(C \leq 8)}$, alkenyl$_{(C \leq 8)}$, aryl$_{(C \leq 12)}$, aralkyl$_{(C \leq 12)}$, acyl$_{(C \leq 8)}$, or a substituted version of any of these groups; and $R_{22}$ is aryl$_{(C \leq 12)}$, aralkyl$_{(C \leq 12)}$, or a substituted version of either of these groups; in the presence of a base. In some embodiments, $Y_4$, $Y_5$, and $Y_6$ are alkyl$_{(C \leq 6)}$. In some embodiments, $Y_4$, $Y_5$, and $Y_6$ are methyl. In some embodiments, $R_{16}$ and $R_{16}'$ are alkoxy$_{(C \leq 8)}$ or substituted alkoxy$_{(C \leq 8)}$. In some embodiments, $R_{16}$ and $R_{16}'$ are methoxy. In some embodiments, $R_{17}$ is hydrogen, amino, halo, hydroxy; alkylamino$_{(C \leq 12)}$, substituted alkylamino$_{(C \leq 12)}$, dialkylamino$_{(C \leq 18)}$, substituted dialkylamino$_{(C \leq 18)}$, or —C(O)OCH$_2$CH$_2$Si(CH$_3$)$_3$; In some embodiments, $R_{17}$ is amino, hydroxy, or halo. In other embodiments, $R_{17}$ is dimethylamino or 2-aminoethylmethylamino. In some embodiments, $X_3$ and $X_5$ are O. In some embodiments, $X_4$ is hydroxy. In other embodiments, $X_4$ is O. In some embodiments, $R_{18}$ is hydrogen, alkyl$_{(C \leq 8)}$, substituted alkyl$_{(C \leq 8)}$, or —X$_2$—R$_{11}$, wherein: $X_2$ is alkanediyl$_{(C \leq 12)}$ or substituted alkanediyl$_{(C \leq 12)}$ and $R_{11}$ is hydroxy, amino, heterocycloalkyl$_{(C \leq 12)}$, substituted heterocycloalkyl$_{(C \leq 12)}$, alkylamino$_{(C \leq 8)}$, or substituted alkylamino$_{(C \leq 8)}$, In some embodiments, $R_{18}$ is hydrogen. In some embodiments, $R_{19}$ is hydrogen, amino, halo, hydroxy, alkylamino$_{(C \leq 12)}$, substituted alkylamino$_{(C \leq 12)}$, amido$_{(C \leq 12)}$, substituted amido$_{(C \leq 12)}$, or —NR$_{12}$C(O)R$_{13}$—NR$_{14}$R$_{15}$; wherein: $R_{12}$ is hydrogen, $R_{13}$ is alkanediyl$_{(C \leq 8)}$ or substituted alkanediyl$_{(C \leq 8)}$; and $R_{14}$ and $R_{15}$ are each independently hydrogen, alkyl$_{(C \leq 12)}$, substituted alkyl$_{(C \leq 12)}$, aryl$_{(C \leq 12)}$, substituted aryl$_{(C≤12)}$, aralkyl$_{(C≤12)}$, substituted aralkyl$_{(C≤12)}$, acyl$_{(C≤12)}$, or substituted acyl$_{(C≤12)}$. In some embodiments, $R_{19}$ is hydrogen, halo, amido$_{(C≤12)}$, substituted amido$_{(C≤12)}$, or —NHC(O)CH$_2$—NHR$_{15}$ wherein $R_{15}$ is hydrogen, alkyl$_{(C≤12)}$, or substituted alkyl$_{(C≤12)}$. In some embodiments, $R_{20}$ is hydrogen, alkyl$_{(C≤6)}$, or substituted alkyl$_{(C≤6)}$. In some embodiments, $R_{20}$ is methyl. In some embodiments, $R_{21}$ is aralkyl$_{(C≤12)}$ or substituted aralkyl$_{(C≤12)}$. In some embodiments, $R_{21}$ is benzyl. In some embodiments, $R_{22}$ is aryl$_{(C≤12)}$ or substituted aryl$_{(C≤12)}$. In some embodiments, $R_{22}$ is phenyl. In other embodiments, $R_{17}$ is not hydrogen or —C(O)OCH$_2$CH$_2$Si(CH$_3$)$_3$, $R_{18}$ is not benzyl, $R_{19}$ are not hydrogen, and $R_{20}$ is not methyl. In some embodiments, the base is an alkoxide$_{(C≤18)}$. In some embodiments, the alkoxide$_{(C≤18)}$ is t-butoxide. In some embodiments, the method comprises adding from about 1.0 to about 2.0 equivalents of base relative to the compound of formula VII. In some embodiments, the method comprises adding from about 1.0 to about 1.5 equivalents of base. In some embodiments, the method comprises adding about 1.2 equivalents of base. In some embodiments, the method comprises adding from about 0.9 to about 2.0 equivalents of the compound of formula VIII relative to the compound of formula VII. In some embodiments, the method comprises adding from about 1.0 to about 1.5 equivalents of the compound of formula VIII. In some embodiments, the method comprises adding about 1.1 equivalents of the compound of formula VIII. In some embodiments, the method further comprises a solvent. In some embodiments, the solvent is an organic solvent. In some embodiments, the solvent is an arene$_{(C≤12)}$. In some embodiments, the solvent is toluene. In some embodiments, the reaction comprises running the reaction at a temperature from about 0° C. to about 50° C. In some embodiments, the temperature is from about 20° C. to about 35° C. In some embodiments, the temperature is about 25° C. In some embodiments, the temperature is about room temperature. In some embodiments, the reaction is run for a time period from about 5 minutes to about 2 hours. In some embodiments, the time period is from about 10 minutes to about 45 minutes. In some embodiments, the time period is about 15 minutes. In some embodiments, the reaction results in a yield of greater than about 50%. In some embodiments, the yield is greater than about 75%. In some embodiments, the yield is greater than about 90%. In some embodiments, the reaction produces a diastereomeric ratio of greater than about 1:1. In some embodiments, the diastereomeric ratio is greater than about 1.75:1. In some embodiments, the diastereomeric ratio is about 2:1.

In some embodiments, the method further comprises forming a compound of the formula:

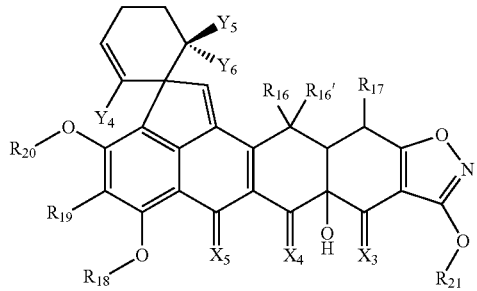

(IX)

wherein: $Y_4$, $Y_5$, and $Y_6$ are each independently hydrogen, alkyl$_{(C≤8)}$ or substituted alky$_{(C≤8)}$; $R_{16}$ and $R_{16}'$ are each independently hydrogen, alkoxy$_{(C≤8)}$, aralkoxy$_{(C≤12)}$, substituted alkoxy$_{(C≤8)}$, or substituted aralkoxy$_{(C≤12)}$; or $R_{16}$ and $R_{16}'$ are taken together and are alkoxydiyl$_{(C≤12)}$; $R_{17}$ is hydrogen, amino, carboxy, cyano, halo, hydroxy, nitro, or sulfo; alkyl$_{(C≤12)}$, alkoxy$_{(C≤12)}$, alkylamino$_{(C≤12)}$, dialkylamino$_{(C≤18)}$, or a substituted version of any of these groups; or —C(O)OCH$_2$CH$_2$Si(CH$_3$)$_3$; $X_3$ is O, NH, S, or CH$_2$; $X_4$ is O, NH, or S; $X_5$ is O, NH, or S; $R_{18}$ is hydrogen, alkyl$_{(C≤8)}$, alkenyl$_{(C≤8)}$, aryl$_{(C≤12)}$, aralkyl$_{(C≤12)}$, acyl$_{(C≤8)}$, or a substituted version of any of these groups; or —X$_2$—R$_{11}$, wherein: $X_2$ is alkanediyl$_{(C≤12)}$ or substituted alkanediyl$_{(C≤12)}$; and $R_{11}$ is hydroxy, amino, azido, carboxy, or cyano, alkenyl$_{(C≤6)}$, alkynyl$_{(C≤6)}$, heterocycloalkyl$_{(C≤12)}$, alkylamino$_{(C≤8)}$, dialkylamino$_{(C≤8)}$, alkoxy$_{(C≤8)}$, or a substituted version of any of these groups; $R_{19}$ is hydrogen, amino, carboxy, cyano, halo, hydroxy, nitro, or sulfo; alkyl$_{(C≤12)}$, alkoxy$_{(C≤12)}$, alkylamino$_{(C≤12)}$, dialkylamino$_{(C≤18)}$, amido$_{(C≤12)}$, or a substituted version of any of these groups; or —NR$_{12}$C(O)R$_{13}$—NR$_{14}$R$_{15}$; wherein: $R_{12}$ is hydrogen, alkyl$_{(C≤8)}$), or substituted alkyl$_{(C≤8)}$; $R_{13}$ is alkanediyl$_{(C≤8)}$ or substituted alkanediyl$_{(C≤8)}$; and $R_{14}$ and $R_{15}$ are each independently selected from: hydrogen, alkyl$_{(C≤8)}$, aryl$_{(C≤12)}$, aralkyl$_{(C≤12)}$, acyl$_{(C≤12)}$, or a substituted version of any of these groups; or $R_{14}$ and $R_{15}$ are taken together and are alkanediyl$_{(C≤8)}$, alkoxydiyl$_{(C≤8)}$, alkylaminodiyl$_{(C≤8)}$, or a substituted version of any of these groups; and $R_{20}$ and $R_{21}$ are each independently hydrogen, alkyl$_{(C≤8)}$, alkenyl$_{(C≤8)}$, aryl$_{(C≤12)}$, aralkyl$_{(C≤12)}$, acyl$_{(C≤8)}$, or a substituted version of any of these groups; or a salt, tautomer, or optical isomer thereof, comprising reacting a compound of the formula:

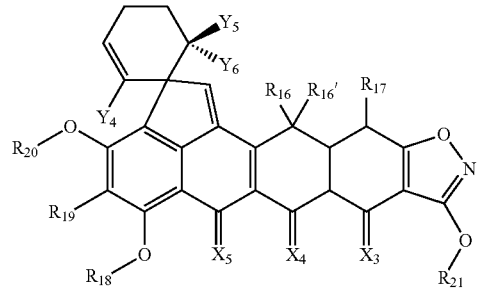

(X)

wherein the variables are as defined above; with a metal catalyst and an oxidizing agent. In some embodiments, $R_{17}$ is not hydrogen, $R_{18}$ is not benzyl, $R_{19}$ is not hydrogen, and $R_{20}$ is not methyl. In some embodiments, the metal catalyst is a nickel(II) salt. In some embodiments, the nickel(II) salt is Ni(acac)$_2$. In some embodiments, the reaction comprises adding from about 0.01 to about 1.0 equivalents of the metal catalyst relative to the compound of formula X. In some embodiments, the reaction comprises adding from about 0.1 to about 0.5 equivalents of the metal catalyst. In some embodiments, the reaction comprises adding about 0.2 equivalents of the metal catalyst. In some embodiments, the oxidizing agent is a dioxirane compound. In some embodiments, the oxidizing agent is dimethyldioxirane (DMDO). In some embodiments, the reaction comprises adding from about 1.5 equivalents to about 10.0 equivalents of dimethyldioxirane relative to the compound of formula X. In some embodiments, the reaction comprises adding from about 4.0 equivalents to about 6.0 equivalents of dimethyldioxirane. In some embodiments, the reaction comprises adding about 5.1 equivalents of dimethyldioxirane. In some embodiments, the method further comprises adding additional dimethyldioxirane every two hours during the reaction. In some embodiments, the additional dimethyldioxirane is about 1.5 equivalents relative to the compound of formula X. In some embodiments, the method further comprises a solvent. In some embodiments, the solvent is an organic solvent. In some embodiments, the solvent is a haloalkane$_{(C\leq12)}$. In some embodiments, the solvent is dichloromethane. In some embodiments, the reaction comprises running the reaction at a temperature from about −90° C. to about −40° C. In some embodiments, the temperature is from about −80° C. to about −60° C. In some embodiments, the temperature is about −78° C. In some embodiments, the method further comprises allowing the reaction to warm to a temperature from about −80° C. to about −30° C. In some embodiments, the temperature is about −60° C. In some embodiments, the reaction is run for a time period from about 3 hours to about 12 hours. In some embodiments, the time period is from about 5 hours to about 8 hours. In some embodiments, the time period is about 6.5 hours. In some embodiments, the starting material is recovered after the time period and subject to the reaction conditions again. In some embodiments, the reaction results in a yield of greater than about 35% based upon recovered starting material. In some embodiments, the yield is greater than about 50%. In some embodiments, the yield is greater than about 60%. In some embodiments, the reaction produces a diastereomeric ratio of greater than about 1:1. In some embodiments, the diastereomeric ratio is greater than about 1.75:1. In some embodiments, the diastereomeric ratio is about 2:1.

In some embodiments, the reaction further comprises reacting a compound of formula IX with a reducing agent to form a compound of the formula:

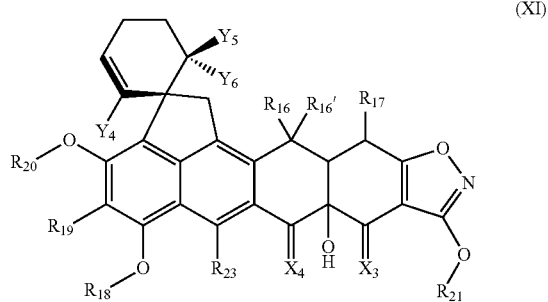

(XI)

wherein: $Y_4$, $Y_5$, and $Y_6$ are each independently hydrogen, alkyl$_{(C\leq8)}$ or substituted alky$_{(C\leq8)}$; $R_{16}$ and $R_{16}'$ are each independently hydrogen, alkoxy$_{(C\leq8)}$, aralkoxy$_{(C\leq12)}$, substituted alkoxy$_{(C\leq8)}$, or substituted aralkoxy$_{(C\leq12)}$; or $R_{16}$ and $R_{16}'$ are taken together and are alkoxydiyl$_{(C\leq12)}$; $R_{17}$ is hydrogen, amino, carboxy, cyano, halo, hydroxy, nitro, or sulfo; alkyl$_{(C\leq12)}$, alkoxy$_{(C\leq12)}$, alkylamino$_{(C\leq12)}$, dialkylamino$_{(C\leq18)}$, or a substituted version of any of these groups; or —C(O)OCH$_2$CH$_2$Si(CH$_3$)$_3$; $X_3$ is O, NH, S, or CH$_2$; $X_4$ is O, NH, or S; $R_{18}$ is hydrogen, alkyl$_{(C\leq8)}$, alkenyl$_{(C\leq8)}$, aryl$_{(C\leq12)}$, aralkyl$_{(C\leq12)}$, acyl$_{(C\leq8)}$, or a substituted version of any of these groups; or —X$_2$—R$_{11}$, wherein: X$_2$ is alkanediyl$_{(C\leq12)}$ or substituted alkanediyl$_{(C\leq12)}$; and R$_{11}$ is hydroxy, amino, azido, carboxy, or cyano, alkenyl$_{(C\leq6)}$, alkynyl$_{(C\leq6)}$, heterocycloalkyl$_{(C\leq12)}$, alkylamino$_{(C\leq8)}$, dialkylamino$_{(C\leq8)}$, alkoxy$_{(C\leq8)}$, or a substituted version of any of these groups; $R_{19}$ is hydrogen, amino, carboxy, cyano, halo, hydroxy, nitro, or sulfo; alkyl$_{(C\leq12)}$, alkoxy$_{(C\leq12)}$, alkylamino$_{(C\leq12)}$, dialkylamino$_{(C\leq18)}$, amido$_{(C\leq12)}$, or a substituted version of any of these groups; or —NR$_{12}$C(O)R$_{13}$—NR$_{14}$R$_{15}$; wherein: R$_{12}$ is hydrogen, alkyl$_{(C\leq8)}$, or substituted alkyl$_{(C\leq8)}$; R$_{13}$ is alkanediyl$_{(C\leq8)}$ or substituted alkanediyl$_{(C\leq8)}$; and R$_{14}$ and R$_{15}$ are each independently selected from: hydrogen, alkyl$_{(C\leq12)}$, aryl$_{(C\leq12)}$, aralkyl$_{(C\leq12)}$, acyl$_{(C\leq12)}$, or a substituted version of any of these groups; or R$_{14}$ and R$_{15}$ are taken together and are alkanediyl$_{(C\leq8)}$, alkoxydiyl$_{(C\leq8)}$, alkylaminodiyl$_{(C\leq8)}$, or a substituted version of any of these groups; R$_{20}$ and R$_{21}$ are each independently hydrogen, alkyl$_{(C\leq8)}$, alkenyl$_{(C\leq8)}$, aryl$_{(C\leq12)}$, aralkyl$_{(C\leq12)}$, acyl$_{(C\leq8)}$, or a substituted version of any of these groups; and R$_{23}$ is hydroxy, alkoxy$_{(C\leq12)}$, or substituted alkoxy$_{(C\leq12)}$; or a salt, tautomer, or optical isomer thereof. In some embodiments, the reducing agent is a soft hydride donor. In some embodiments, the reducing agent is a metal borohydride reagent. In some embodiments, the reducing agent is sodium cyanoborohydride. In some embodiments, the reaction comprises adding from about 5.0 equivalents to about 25.0 equivalents of reducing agent relative to the compound of formula IX. In some embodiments, the reaction comprises adding from about 8.0 equivalents to about 12.0 equivalents of reducing agent. In some embodiments, the reaction comprises adding about 10.0 equivalents of reducing agent. In some embodiments, the method further comprises a solvent. In some embodiments, the solvent is an organic solvent. In some embodiments, the solvent is a ether$_{(C\leq12)}$. In some embodiments, the solvent is tetrahydrofuran. In some embodiments, the reaction comprises running the reaction at a temperature from about −90° C. to about −40° C. In some embodiments, the temperature is from about −80° C. to about −60° C. In some embodiments, the temperature is about −78° C. In some embodiments, the method further comprises allowing the reaction to warm to a temperature from about −80° C. to about −30° C. In some embodiments, the temperature is about −60° C. In some embodiments, the reaction is run for a time period from about 30 minutes to about 6 hours. In some embodiments, the time period is from about 1 hour to about 3 hours. In some embodiments, the time period is about 1.5 hours. In some embodiments, the reaction results in a yield of greater than about 20%. In some embodiments, the yield is greater than about 25%. In some embodiments, the yield is greater than about 35%. In some embodiments, the reaction produces a diastereomeric ratio of greater than about 1:1. In some embodiments, the diastereomeric ratio is greater than about 1.75:1. In some embodiments, the diastereomeric ratio is about 2:1.

In some embodiments, one or more steps of the reaction further comprises purifying the reaction in a purification step. In some embodiments, the purification method is chromatography. In some embodiments, the purification method is column chromatography or high performance liquid chromatography.

It is contemplated that any method or composition described herein can be implemented with respect to any other method or composition described herein. For example, an aldehyde synthesized by one method may be used in the preparation of a final compound according to a different method.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed.

FIGS. 1A & B—Structures of bacterial tetracyclines and designed analogs (1A) and fungal tetracyclines (1B)

FIG. 4—Structures of Viridicatumtoxin B and A (1 and 2, respectively) and analogs (V2-V6).

DESCRIPTION OF ILLUSTRATIVE EMBODIMENTS

Figure 2:
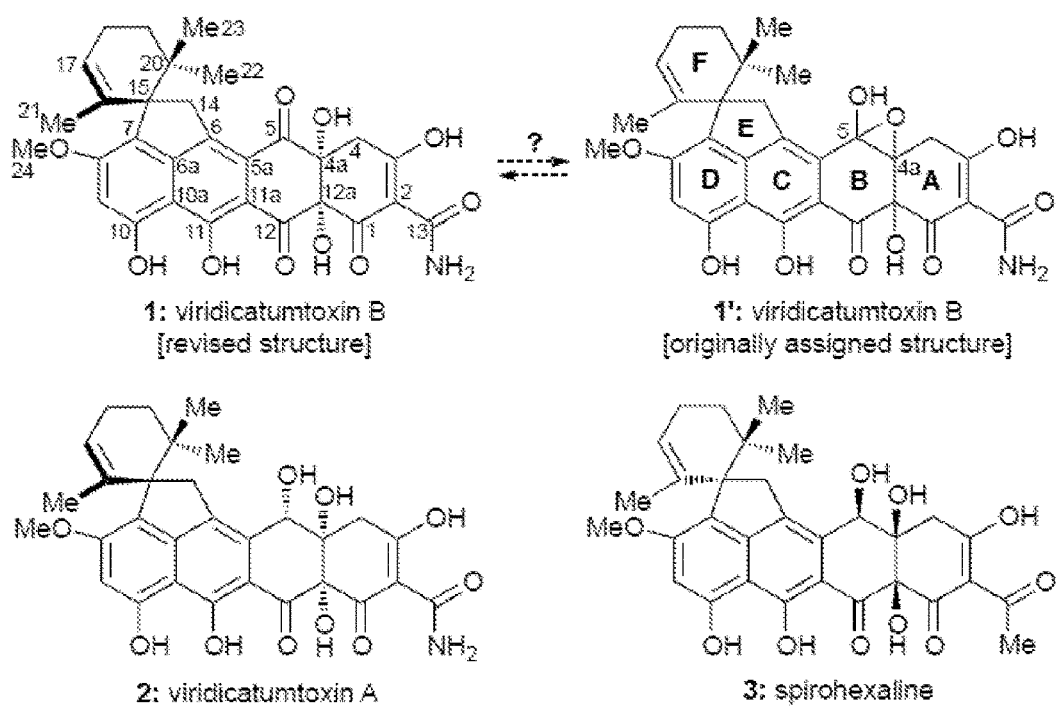
FIG. 2—Structures of Viridicatumtoxin B and A (1 and 2, respectively), original proposed structure of Viridicatumtoxin B, and spirohexaline.
Figure 3:
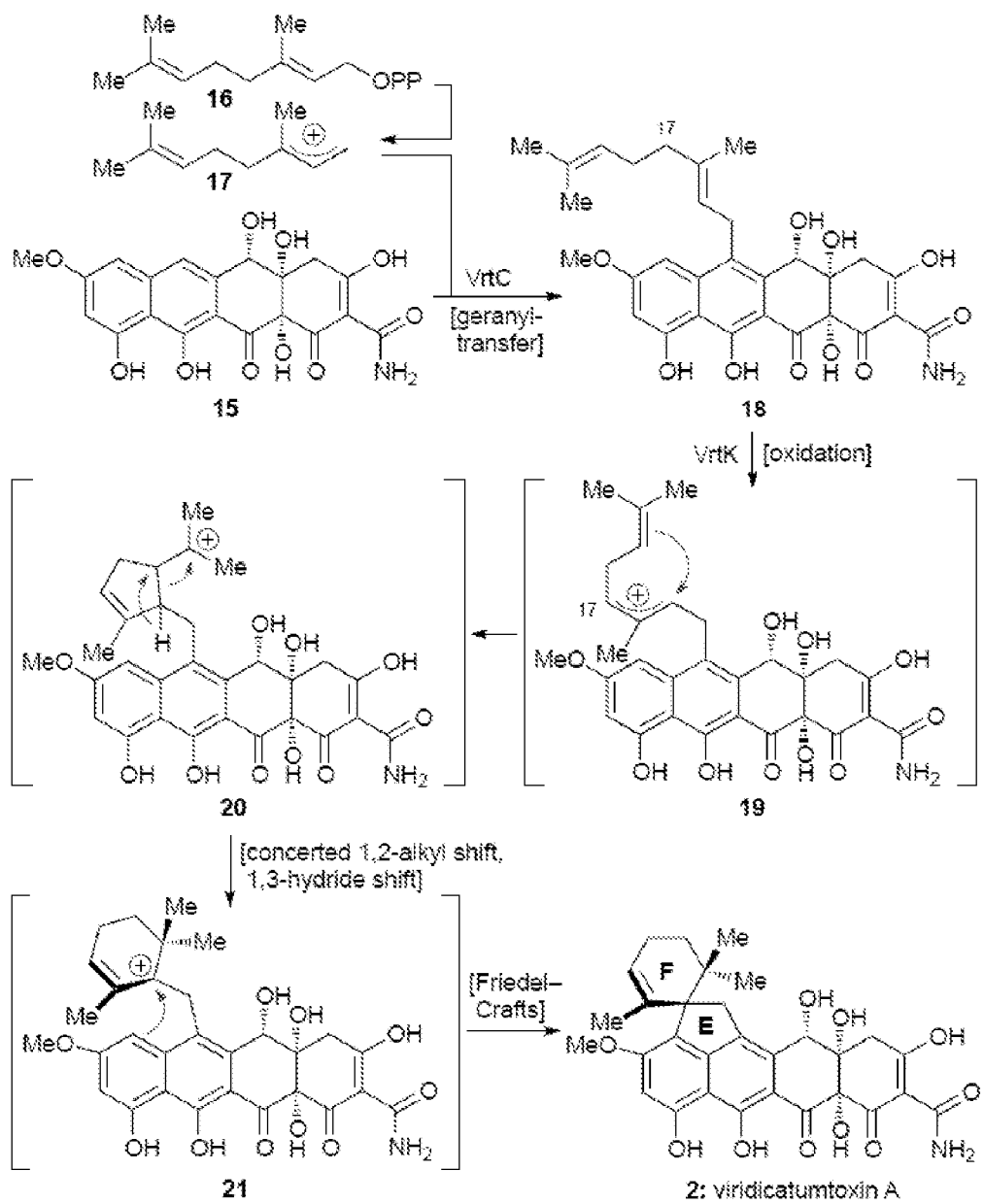
FIG. 3—Biosynthetic Pathway of Viridicatumtoxin A production in vivo.

The present disclosure relates to a series of novel analogs of viridicatumtoxin and an improved synthetic pathway to obtain viridicatumtoxin and its analogs. In some aspects, the analogs of the fungal secondary metabolites viridicatumtoxin A (2) and B (1) (FIG. 4) are useful as potent antibiotics against a variety of Gram-positive and certain Gram-negative bacterial strains. In the present disclosure, a collection of viridicatumtoxin analogs (V2-V6, FIG. 4) are synthesized and their antibiotic profile is evaluated. These and other aspects of the disclosure are described in greater detail below.

I. Compounds and Formulations Thereof

In one aspect, the present invention provides compounds of the formula:

(I)

wherein: $X_1$ is absent such that atoms 16 and 17 are only connected by the shown single bond, a covalent bond such that a double bond is formed between atoms 16 and 17, —O—, alkanediyl$_{(C\leq 8)}$, or substituted alkanediyl$_{(C\leq 8)}$; $Y_1$, $Y_2$, and $Y_3$ are each independently alkyl$_{(C\leq 12)}$ or substituted alkyl$_{(C\leq 12)}$; $R_1$ is hydrogen, hydroxy, or oxo, provided that when $R_1$ is oxo, the bond between $R_1$ and atom number 5 is a double bond and when the bond between $R_1$ and atom number 5 is a double bond then $R_1$ is oxo, alkoxy$_{(C\leq 8)}$, or substituted alkoxy$_{(C\leq 8)}$; $R_2$ is hydrogen, amino, carboxy, cyano, halo, hydroxy, nitro, or sulfo; alkyl$_{(C\leq 12)}$, alkoxy$_{(C\leq 12)}$, alkylamino$_{(C\leq 12)}$, dialkylamino$_{(C\leq 18)}$, or a substituted version of any of these groups; $R_3$, $R_6$, $R_7$, and $R_{10}$ are each independently selected from: hydrogen, alkyl$_{(C\leq 8)}$, alkenyl$_{(C\leq 8)}$, aryl$_{(C\leq 12)}$, aralkyl$_{(C\leq 12)}$, acyl$_{(C\leq 8)}$, or a substituted version of any of these groups; $R_4$ and $R_5$ are each independently selected from: hydrogen, alkyl$_{(C\leq 8)}$, alkanediyl$_{(C\leq 8)}$-heterocycloalkyl$_{(C\leq 8)}$, alkanediyl$_{(C\leq 8)}$-heteroaryl$_{(C\leq 8)}$, alkanediyl$_{(C\leq 8)}$-alkylamino$_{(C\leq 8)}$, alkanediyl$_{(C\leq 8)}$-dialkylamino$_{(C\leq 8)}$, or a substituted version of any of these groups; $R_8$ is hydrogen, alkyl$_{(C\leq 8)}$, alkenyl$_{(C\leq 8)}$, aryl$_{(C\leq 12)}$, aralkyl$_{(C\leq 12)}$, acyl$_{(C\leq 8)}$, or a substituted version of any of these groups; or —$X_2$—$R_{11}$, wherein: $X_2$ is alkanediyl$_{(C\leq 12)}$ or substituted alkanediyl$_{(C\leq 12)}$; and $R_{11}$ is hydroxy, amino, azido, carboxy, or cyano, alkenyl$_{(C\leq 6)}$, alkynyl$_{(C\leq 6)}$, heterocycloalkyl$_{(C\leq 12)}$, alkylamino$_{(C\leq 8)}$, dialkylamino$_{(C\leq 8)}$, alkoxy$_{(C\leq 8)}$, or a substituted version of any of these groups; or a -linker-biomolecule wherein the biomolecule is a protein, a polypeptide, an amino acid, a cofactor, an imaging agent, an antibody, a fatty acid, a nucleic acid, or a small molecule therapeutic agent; and $R_9$ is hydrogen, amino, carboxy, cyano, halo, hydroxy, nitro, or sulfo; alkyl$_{(C\leq 12)}$, alkoxy$_{(C\leq 12)}$, alkylamino$_{(C\leq 12)}$, dialkylamino$_{(C\leq 18)}$, amido$_{(C\leq 12)}$, or a substituted version of any of these groups; or —$NR_{12}C(O)R_{13}$—$NR_{14}R_{15}$; wherein: $R_{12}$ is hydrogen, alkyl$_{(C\leq 8)}$, or substituted alkyl$_{(C\leq 8)}$; $R_{13}$ is alkanediyl$_{(C\leq 8)}$ or substituted alkanediyl$_{(C\leq 8)}$; and $R_{14}$ and $R_{15}$ are each independently selected from: hydrogen, alkyl$_{(C\leq 12)}$, aryl$_{(C\leq 12)}$, aralkyl$_{(C\leq 12)}$, acyl$_{(C\leq 12)}$, or a substituted version of any of these groups; or $R_{14}$ and $R_{15}$ are taken together and are alkanediyl$_{(C\leq 8)}$, alkoxydiyl$_{(C\leq 8)}$, alkylaminodiyl$_{(C\leq 8)}$, or a substituted version of any of these groups; or a pharmaceutically acceptable salt or tautomer thereof.

Additionally, the compounds provided by the present disclosure are shown, for example, above in the summary of the invention section and in the examples and claims below. They may be made using the methods outlined in the Examples section. Viridicatumtoxin and its derivatives can be synthesized according to the methods described, for example, in the Examples section below. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Viridicatumtoxin and its derivatives of the disclosure may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Chemical formulas used to represent viridicatumtoxin and its derivatives of the disclosure will typically only show one of possibly several different tautomers. For example, many types of ketone groups are known to exist in equilibrium with corresponding enol groups. Similarly, many types of imine groups exist in equilibrium with enamine groups.

Regardless of which tautomer is depicted for a given compound, and regardless of which one is most prevalent, all tautomers of a given chemical formula are intended.

Viridicatumtoxin and its derivatives of the disclosure may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up viridicatumtoxin and its derivatives of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

Viridicatumtoxin and its derivatives of the present disclosure may also exist in prodrug form. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the invention contemplates prodrugs of compounds of the present invention as well as methods of delivering prodrugs. Prodrugs of viridicatumtoxin and its derivatives employed in the disclosure may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

Those skilled in the art of organic chemistry will appreciate that many organic compounds can form complexes with solvents in which they are reacted or from which they are precipitated or crystallized. These complexes are known as "solvates." For example, a complex with water is known as a "hydrate." Solvates of viridicatumtoxin and its derivatives provided herein are within the scope of the invention. It will also be appreciated by those skilled in organic chemistry that many organic compounds can exist in more than one crystalline form. For example, crystalline form may vary from solvate to solvate. Thus, all crystalline forms of viridicatumtoxin and its derivatives or the pharmaceutically acceptable solvates thereof are within the scope of the present invention.

B. Formulations

In some embodiments of the present disclosure, the compounds are included a pharmaceutical formulation. Materials for use in the preparation of microspheres and/or microcapsules are, e.g., biodegradable/bioerodible polymers such as polygalactin, poly-(isobutyl cyanoacrylate), poly(2-hydroxyethyl-L-glutam-nine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

Formulations for oral use include tablets containing the active ingredient(s) (e.g., viridicatumtoxin and its derivatives) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

II. Microbial Infections

A. Bacterial Infections

In some aspects of the present disclosure, the compounds disclosed herein may be used to treat a bacterial infection. While humans contain numerous different bacteria on and inside their bodies, an imbalance in bacterial levels or the introduction of pathogenic bacteria can cause a symptomatic bacterial infection. Pathogenic bacteria cause a variety of different diseases including but not limited to numerous foodborne illness, typhoid fever, tuberculosis, pneumonia, syphilis, and leprosy.

Additionally, different bacteria have a wide range of interactions with body and those interactions can modulate ability of the bacteria to cause an infection. For example, bacteria can be conditionally pathogenic such that they only cause an infection under specific conditions. For example, *Staphylococcus* and *Streptococcus* bacteria exist in the normal human bacterial biome, but these bacteria when they are allowed to colonize other parts of the body causing a skin infection, pneumonia, or sepsis. Other bacteria are known as opportunistic pathogens and only cause diseases in a patient with a weakened immune system or another disease or disorder.

Bacteria can also be intracellular pathogens which can grow and reproduce within the cells of the host organism. Such bacteria can be divided into two major categories as either obligate intracellular parasites or facultative intracellular parasites. Obligate intracellular parasites require the host cell in order to reproduce and include such bacteria as but are not limited to *Chlamydophila, Rickettsia*, and *Ehrlichia* which are known to cause pneumonia, urinary tract infections, typhus, and Rocky Mountain spotted fever. Facultative intracellular parasites can reproduce either intracellular or extracellular. Some non-limiting examples of facultative intracellular parasites include *Salmonella, Listeria, Legionella, Mycobacterium*, and *Brucella* which are known to cause food poisoning, typhoid fever, sepsis, meningitis, Legionnaire's disease, tuberculosis, leprosy, and brucellosis.

Finally, bacterial infections could be targeted to a specific location in or on the body. For example, bacteria could be harmless if only exposed to the specific organs, but when it comes in contact with a specific organ or tissue, the bacteria can begin replicating and cause a bacterial infection.

In particular, the inventors contemplate treatment of bacterial infections, including those caused by *Staphyloccoccus aureus*. *S. aureus* is a major human pathogen, causing a wide variety of illnesses ranging from mild skin and soft tissue infections and food poisoning to life-threatening illnesses such as deep post-surgical infections, septicaemia, endocarditis, necrotizing pneumonia, and toxic shock syndrome. These organisms have a remarkable ability to accumulate additional antibiotic resistance determinants, resulting in the formation of multiply-drug-resistant strains.

Methicillin, being the first semi-synthetic penicillin to be developed, was introduced in 1959 to overcome the problem of penicillin-resistant *S. aureus* due to β-lactamase (penicillinase) production (Livermore, 2000). However, methicillin-resistant *S. aureus* (MRSA) strains were identified soon after the introduction of methicillin (Barber, 1961; Jevons, 1961). MRSA have acquired and integrated into their genome a 21- to 67-kb mobile genetic element, termed the staphylococcal cassette chromosome mec (SCCmec) that harbors the methicillin resistance (mecA) gene and other antibiotic resistance determinants (Ito et al., 2001; Ito et al., 2004; Ma et al., 2002). The mecA gene encodes an altered additional low affinity penicillin-binding protein (PBP2a) that confers broad resistance to all penicillin-related compounds including cephalosporins and carbapenems that are currently some of the most potent broad-spectrum drugs available (Hackbarth & Chambers, 1989). Since their first identification, strains of MRSA have spread and become established as major nosocomial (hospital-acquired (HA)-MRSA) pathogens worldwide (Ayliffe, 1997; Crossley et al., 1979; Panlilio et al., 1992; Voss et al., 1994). These organisms have evolved and emerged as a major cause of community-acquired infections (CA-MRSA) in healthy individuals lacking traditional risk factors for infection, and are causing community-outbreaks, which pose a significant threat to public health.

i. Gram Positive Bacteria

In some aspects of the present disclosure, the compounds disclosed herein may be used to treat a bacterial infection by a gram positive bacteria. Gram positive bacteria contain a thick peptidoglycan layer within the cell wall which prevents the bacteria from releasing the stain when dyed with crystal violet. Without being bound by theory, the gram positive bacteria are often more susceptible to antibiotics. Generally, gram positive bacteria, in addition to the thick peptidoglycan layer, also comprise a lipid monolayer and contain teichoic acids which react with lipids to form lipoteichoic acids that can act as a chelating agent. Additionally, in gram positive bacteria, the peptidoglycan layer is outer surface of the bacteria. Many gram positive bacteria have been known to cause disease including, but are not limited to, *Streptococcus, Straphylococcus, Corynebacterium, Enterococcus, Listeria, Bacillus, Clostridium, Rathybacter, Leifsonia*, and *Clavibacter*.

ii. Gram Negative Bacteria

In some aspects of the present disclosure, the compounds disclosed herein may be used to treat a bacterial infection by a gram negative bacteria. Gram negative bacteria do not retain the crystal violet stain after washing with alcohol. Gram negative bacteria, on the other hand, have a thin peptidoglycan layer with an outer membrane of lipopolysaccharides and phospholipids as well as a space between the peptidoglycan and the outer cell membrane called the periplasmic space. Gram negative bacterial generally do not have teichoic acids or lipoteichoic acids in their outer coating. Generally, gram negative bacteria also release some endotoxin and contain prions which act as molecular transport units for specific compounds. Most bacteria are gram negative. Some non-limiting examples of gram negative bacteria include *Bordetella, Borrelia, Burcelia, Campylobacteria, Escherichia, Francisella, Haemophilus, Helicobacter, Legionella, Leptospira, Neisseria, Pseudomonas, Rickettsia, Salmonella, Shigella, Treponema, Vibrio*, and *Yersinia*.

Iii. Gram Indeterminate Bacteria

In some aspects of the present disclosure, the compounds disclosed herein may be used to treat a bacterial infection by a gram indeterminate bacteria. Gram indeterminate bacteria do not full stain or partially stain when exposed to crystal violet. Without being bound by theory, a gram indeteriminate bacteria may exhibit some of the properties of the gram positive and gram negative bacteria. A non-limiting example of a gram indeterminate bacteria include *mycobacterium tuberculosis* or *mycobacterium leprae*.

B. Viral Infections

In some aspects of the present disclosure, the compounds disclosed herein may be used to treat a viral infection. Similarly, virus can also exist in pathogenic form which can lead to human diseases. Viral infections are typically not treated directly but rather symptomatically since virus often have a self-limiting life cycle. Viral infections can also be more difficult to diagnosis than a bacterial infection since viral infections often do result in the concombinent increase in white blood cell counts. Some non-limiting examples of pathogenic virus include influenza virus, smallpox, BK virus, JC virus, human papillomavirus, adenovirus, herpes simplex type 1, herpes simplex type 2, varicella-zoster virus, Epstein barr virus, human cytomegalovirus, human herpesvirus type 8, Norwalk virus, human bocavirus, rubella virus, hepatitis E virus, hepatitis B virus, human immunodeficiency virus (HIV), Ebola virus, rabies virus, rotavirus, and hepatitis D virus.

III. Hyperproliferative Diseases

A. Cancer and Other Hyperproliferative Disease

While hyperproliferative diseases can be associated with any disease which causes a cell to begin to reproduce uncontrollably, the prototypical example is cancer. One of the key elements of cancer is that the cell's normal apoptotic cycle is interrupted and thus agents that interrupt the growth of the cells are important as therapeutic agents for treating these diseases. In this disclosure, the viridicatumtoxin derivatives may be used to lead to decreased cell counts and as such can potentially be used to treat a variety of types of cancer lines. In various aspects, it is anticipated that the viridicatumtoxin derivatives of the present disclosure may be used to treat virtually any malignancy.

Cancer cells that may be treated with the compounds of the present disclosure include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

III. Therapies

A. Pharmaceutical Formulations and Routes of Administration

Where clinical applications are contemplated, it will be necessary to prepare pharmaceutical compositions in a form appropriate for the intended application. In some embodiments, such formulation with the compounds of the present disclosure is contemplated. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. Such routes include oral, nasal, buccal, rectal, vaginal or topical route. Alternatively, administration may be by orthotopic, intradermal, subcutaneous, intramuscular, intratumoral, intraperitoneal, or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration viridicatumtoxin and its derivatives may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

B. Methods of Treatment

In particular, the compositions that may be used in treating microbial infections and cancer in a subject (e.g., a human subject) are disclosed herein. The compositions described above are preferably administered to a mammal (e.g., rodent, human, non-human primates, canine, bovine, ovine, equine, feline, etc.) in an effective amount, that is, an amount capable of producing a desirable result in a treated subject (e.g., causing apoptosis of cancerous cells or killing bacterial cells). Toxicity and therapeutic efficacy of the compositions utilized in methods of the invention can be determined by standard pharmaceutical procedures. As is well known in the medical and veterinary arts, dosage for any one animal depends on many factors, including the subject's size, body surface area, body weight, age, the particular composition to be administered, time and route of administration, general health, the clinical symptoms of the infection or cancer and other drugs being administered concurrently. A composition as described herein is typically administered at a dosage that inhibits the growth or proliferation of a bacterial cell, inhibits the growth of a biofilm, or induces death of cancerous cells (e.g., induces apoptosis of a cancer cell), as assayed by identifying a reduction in hematological parameters (Complete blood count (CBC)), or cancer cell growth or proliferation. In some embodiments, in the experiments described herein and based upon dosing of other tetracycline compounds, the amount of the viridicatumtoxin derivatives used to inhibit bacterial growth, treat a viral infection, or induce apoptosis of the cancer cells is calculated to be from about 0.01 mg to about 10,000 mg/day. In some embodiments, the amount is from about 1 mg to about 1,000 mg/day. In some embodiments, these dosings may be reduced or increased based upon the biological factors of a particular patient such as increased or decreased metabolic breakdown of the drug or decreased uptake by the digestive tract if administered orally. Additionally, the new derivatives of viridicatumtoxin may be more efficacious and thus a smaller dose is required to achieve a similar effect. Such a dose is typically administered once a day for a few weeks or until sufficient reducing in cancer cells has been achieved.

The therapeutic methods of the invention (which include prophylactic treatment) in general include administration of a therapeutically effective amount of the compositions described herein to a subject in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, marker (as defined herein), family history, and the like).

In one embodiment, the invention provides a method of monitoring treatment progress. The method includes the step of determining a level of changes in hematological parameters and/or cancer stem cell (CSC) analysis with cell surface proteins as diagnostic markers (which can include, for example, but are not limited to CD34, CD38, CD90, and CD117) or diagnostic measurement (e.g., screen, assay) in a subject suffering from or susceptible to a disorder or symptoms thereof associated with cancer (e.g., leukemia) in which the subject has been administered a therapeutic amount of a composition as described herein. The level of marker determined in the method can be compared to known levels of marker in either healthy normal controls or in other afflicted patients to establish the subject's disease status. In preferred embodiments, a second level of marker in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to the methods described herein; this pre-treatment level of marker can then be compared to the level of marker in the subject after the treatment commences, to determine the efficacy of the treatment.

C. Combination Therapies

It is envisioned that the viridicatumtoxin derivatives described herein may be used in combination therapies with an additional antimicrobial agent such as anti-viral, antibiotic, or a compound which mitigates one or more of the side effects experienced by the patient.

Furthermore, it is very common in the field of cancer therapy to combine therapeutic modalities. The following is a general discussion of therapies that may be used in conjunction with the therapies of the present disclosure.

To treat cancers using the methods and compositions of the present disclosure, one would generally contact a tumor cell or subject with a compound and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the compound and the other includes the other agent.

Alternatively, viridicatumtoxin derivatives of the present disclosure may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the compound or the other therapy will be desired. Various combinations may be employed, where a compound of the present disclosure is "A," and the other therapy is "B," as exemplified below:

| | | | | | | | |
|---|---|---|---|---|---|---|---|
| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A | |
| A/A/A/B | B/A/A/A | A/B/A/A | A/A/B/A | A/B/B/B | B/A/B/B | B/B/A/B | |

Agents or factors suitable for use in a combined therapy with agents according to the present disclosure against an infectious disease include antibiotics such as penicillins, cephalosporins, carbapenems, macrolides, aminoglycosides, quinolones (including fluoroquinolones), sulfonamides and tetracylcines. In particular, one may use combination therapies for treating MRSA. Both CA-MRSA and HA-MRSA are resistant to traditional anti-staphylococcal beta-lactam antibiotics, such as cephalexin. CA-MRSA has a greater spectrum of antimicrobial susceptibility, including to sulfa drugs (like co-trimoxazole/trimethoprim-sulfamethoxazole), tetracyclines (like doxycycline and minocycline) and clindamycin (for osteomyelitis), but the drug of choice for treating CA-MRSA is now believed to be vancomycin, according to a Henry Ford Hospital Study. HA-MRSA is resistant even to these antibiotics and often is susceptible only to vancomycin. Newer drugs, such as linezolid (belonging to the newer oxazolidinones class) and daptomycin, are effective against both CA-MRSA and HA-MRSA. The Infectious Disease Society of America recommends vancomycin, linezolid, or clindamycin (if susceptible) for treating patients with MRSA pneumonia. Ceftaroline, a fifth generation cephalosporin, is the first beta-lactam antibiotic approved in the U.S. to treat MRSA infections (skin and soft tissue or community acquired pneumonia only).

Quinolone-resistant *S. aureus* is another emerging pathogen that may be treated with compounds according to the present invention, optionally in combination with vancomycin, teicoplanin and linezolid.

Vancomycin and teicoplanin are glycopeptide antibiotics used to treat MRSA infections. Teicoplanin is a structural congener of vancomycin that has a similar activity spectrum but a longer half-life. Because the oral absorption of vancomycin and teicoplanin is very low, these agents must be administered intravenously to control systemic infections. Treatment of MRSA infection with vancomycin can be complicated, due to its inconvenient route of administration. Moreover, many clinicians believe that the efficacy of vancomycin against MRSA is inferior to that of anti-staphylococcal beta-lactam antibiotics against methicillin-susceptible *Staphylococcus aureus* (MSSA).

Several newly discovered strains of MRSA show antibiotic resistance even to vancomycin and teicoplanin. These new evolutions of the MRSA bacterium have been dubbed Vancomycin intermediate-resistant *Staphylococcus aureus* (VISA). Linezolid, quinupristin/dalfopristin, daptomycin, ceftaroline, and tigecycline are used to treat more severe infections that do not respond to glycopeptides such as vancomycin. Current guidelines recommend daptomycin for VISA bloodstream infections and endocarditis.

Studies suggest that allicin, a compound found in garlic, may prove to be effective in the treatment of MRSA.

Other combinations are contemplated. The following is a general discussion of antibiotic, antiviral, and cancer therapies that may be used in combination with the compounds of the present disclosure.

1. Antibiotics

The term "antibiotics" are drugs which may be used to treat a bacterial infection through either inhibiting the growth of bacteria or killing bacteria. Without being bound by theory, it is believed that antibiotics can be classified into two major classes: bactericidal agents that kill bacteria or bacteriostatic agents that slow down or prevent the growth of bacteria.

The first commercially available antibiotic was released in the 1930's. Since then, many different antibiotics have been developed and widely prescribed. In 2010, on average, 4 in 5 Americans are prescribed antibiotics annually. Given the prevalence of anitbiotics, bacteria have started to develop resistance to specific antibiotics and antibiotic mechanisms. Without being bound by theory, the use of antibiotics in combination with another antibiotic may modulate resistance and enhance the efficacy of one or both agents.

In some embodiments, antibiotics can fall into a wide range of classes. In some embodiments, the compounds of the present disclosure may be used in conjunction with another antibiotic. In some embodiments, the compounds may be used in conjunction with a narrow spectrum antibiotic which targets a specific bacteria type. In some non-limiting examples of bactericidal antibiotics include penicillin, cephalosporin, polymyxin, rifamycin, lipiarmycin, quinolones, and sulfonamides. In some non-limiting examples of bacteriostatic antibiotics include macrolides, lincosamides, or tetracyclines. In some embodiments, the antibiotic is an aminoglycoside such as kanamycin and streptomycin, an ansamycin such as rifaximin and geldanamycin, a carbacephem such as loracarbef, a carbapenem such as ertapenem, imipenem, a cephalosporin such as cephalexin, cefixime, cefepime, and ceftobiprole, a glycopeptide such as vancomycin or teicoplanin, a lincosamide such as lincomycin and clindamycin, a lipopeptide such as daptomycin, a macrolide such as clarithromycin, spiramycin, azithromycin, and telithromycin, a monobactam such as aztreonam, a nitrofuran such as furazolidone and nitrofurantoin, an oxazolidonones such as linezolid, a penicillin such as amoxicillin, azlocillin, flucloxacillin, and penicillin G, an antibiotic polypeptide such as bacitracin, polymyxin B, and colistin, a quinolone such as ciprofloxacin, levofloxacin, and gatifloxacin, a sulfonamide such as silver sulfadiazine, mefenide, sulfadimethoxine, or sulfasalazine, or a tetracycline such as demeclocycline, doxycycline, minocycline, oxytetracycline, or tetracycline. In some embodiments, the compounds could be combined with a drug which acts against mycobacteria such as cycloserine, capreomycin, ethionamide, rifampicin, rifabutin, rifapentine, and streptomycin. Other antibiotics that are contemplated for combination therapies may include arsphenamine, chloramphenicol, fosfomycin, fusidic acid, metronidazole, mupirocin, platensimycin, quinupristin, dalfopristin, thiamphenicol, tigecycline, tinidazole, or trimethoprim.

2. Antivirals

The term "antiviral" or "antiviral agents" are drugs which may be used to treat a viral infection. In general, antiviral agents act via two major mechanisms: preventing viral entry into the cell and inhibiting viral synthesis. Without being bound by theory, viral replication can be inhibited by using agents that mimic either the virus-associated proteins and thus block the cellular receptors or using agents that mimic the cellular receptors and thus block the virus-associated proteins. Furthermore, agents which cause an uncoating of the virus can also be used as antiviral agents.

The second mechanism of viral inhibition is preventing or interrupting viral synthesis. Such drugs can target different proteins associated with the replication of viral DNA including reverse transcriptase, integrase, transcription factors, or ribozymes. Additionally, the therapeutic agent interrupts translation by acting as an antisense DNA strand, inhibiting the formation of protein processing or assembly, or acting as virus protease inhibitors. Finally, an anti-viral agent could additionally inhibit the release of the virus after viral production in the cell.

Additionally, anti-viral agents could modulate the bodies own immune system to fight a viral infection. Without being bound by theory, the anti-viral agent which stimulates the immune system may be used with a wide variety of viral infections.

In some embodiments, the present disclosure provides methods of using the disclosed compounds in a combination therapy with an anti-viral agent as described above. In some non-limiting examples, the anti-viral agent is abacavir, aciclovir, acyclovir, adefovir, amantadine, amprenavir, ampligen, arbidol, atazanavir, atripla, balavir, boceprevirertet, cidofovir, combivir, dolutegravir, daruavir, delavirdine, didanosine, docosanol, edoxudine, efavirenz, emtricitabine, enfuvirtide, entecavir, ecoliever, famciclovir, fomivirsen, fosamprenavir, foscarnet, fosfonet, ganciclovir, ibacitabine, imunovir, idoxuridine, imiquimod, indinavir, inosine, interferon type I, type II, and type III, lamivudine, lopinavir, loviride, maraviroc, moroxydine, methisazone, nelfinavir, nevirapine, nexavir, oseltamivir, penciclovir, peramivir, pleconaril, podophyllotoxin, raltegravir, ribavirin, rimantadine, ritonavir, pyramidine, saquinavir, sofosbuvir, stavudine, telaprevir, tenofovir, tenofovir disoproxil, tipranavir, trifluridine, trizivir, tromantadine, truvada, traporved, valaciclovir, valganciclovir, vicriviroc, vidarabine, viramidine, zalcitabine, zanamivir, or zidovudine. In some embodiments, the anti-viral agents is an anti-retroviral, a fusion inhibitor, an integrase inhibitor, an interferon, a nucleoside analogues, a protease inhibitor, a reverse transcriptase inhibitor, a synergistic enhancer, or a natural product such as tea tree oil.

3. Chemotherapy

The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII; dynemicin, including dynemicin A uncialamycin and derivatives thereof; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcatbien, navelbine, farnesyl-protein tansferase inhibitors, transplatinum, 5-fluorouracil, vincristin, vinblastin and methotrexate and pharmaceutically acceptable salts, acids or derivatives of any of the above.

4. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present invention may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors induce a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and may be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

5. Immunotherapy

In the context of cancer treatment, immunotherapeutics, generally, rely on the use of immune effector cells and molecules to target and destroy cancer cells. Trastuzumab (HERCEPTIN™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, γ-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds may be used to target the anti-cancer agents discussed herein.

Examples of immunotherapies currently under investigation or in use are immune adjuvants e.g., *Mycobacterium bovis*, *Plasmodium falciparum*, dinitrochlorobenzene and aromatic compounds (U.S. Pat. Nos. 5,801,005 and 5,739,169; Hui and Hashimoto, 1998; Christodoulides et al., 1998), cytokine therapy, e.g., interferons α, β, and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

6. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

In some particular embodiments, after removal of the tumor, an adjuvant treatment with a compound of the present disclosure is believe to be particularly efficacious in reducing the reoccurance of the tumor. Additionally, the compounds of the present disclosure can also be used in a neoadjuvant setting.

7. Other Agents

It is contemplated that other agents may be used with the present invention. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1β, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents may be used in combination with the present invention to improve the anti-hyerproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

It also should be pointed out that any of the foregoing therapies may prove useful by themselves in treating cancer.

IV. Synthetic Methods

In some aspects, the compounds of this invention can be synthesized using the methods of organic chemistry as described in this application. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein A. Process Scale-Up The synthetic methods described herein can be further modified and optimized for preparative, pilot- or large-scale production, either batch of continuous, using the principles and techniques of process chemistry as applied by a person skilled in the art. Such principles and techniques are taught, for example, in *Practical Process Research & Development* (2000), which is incorporated by reference herein. The synthetic method described herein may be used to produce preparative scale amounts of viridicatumtoxin and derivatives thereof.

B. Chemical Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof in a divalent context "phosphate" means —OP(O)(OH)O— or a deprotonated form thereof "mercapto" means —SH; and "thio" means =S; "sulfo" means —SO$_3$H, "sulfonyl" means —S(O)$_2$—; and "sulfinyl" means —S(O)—.

In the context of chemical formulas, the symbol "—" means a single bond, "=" means a double bond, and "≡" means triple bond. The symbol "- - - -" represents an optional bond, which if present is either single or double. The symbol "═" represents a single bond or a double bond. Thus, for example, the formula

includes

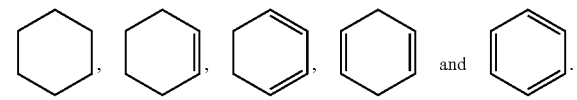

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof The symbol "⁓", when drawn perpendicularly across a bond (e.g., 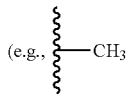

for methyl) indicates a point of attachment of the group. It is noted that the point of attachment is typically only identified in this manner for larger groups in order to assist the reader in unambiguously identifying a point of attachment. The symbol "◄" means a single bond where the group attached to the thick end of the wedge is "out of the page." The symbol "⦀⦀⦀" means a single bond where the group attached to the thick end of the wedge is "into the page". The symbol "〰" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

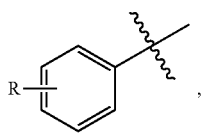

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

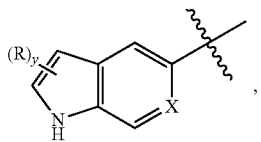

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(Cn)" defines the maximum number (n) of carbon atoms that can be in the group/class, with the minimum number as small as possible for the group in question, e.g., it is understood that the minimum number of carbon atoms in the group "alkenyl$_{(C\leq 8)}$" or the class "alkene$_{(C\leq 8)}$" is two. For example, "alkoxy$_{(C\leq 10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl).

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, and —CH$_2$CH$_2$CH—, are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting example of a haloalkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forms part of one or more non-aromatic ring structures, a cyclo or cyclic structure, no carbon-carbon double or triple bonds, and no atoms other than carbon and hydrogen. Non-limiting examples of cycloalkyl groups include: —CH(CH$_2$)$_2$ (cyclopropyl), cyclobutyl, cyclopentyl, or cyclohexyl. The term "cycloalkanediyl" when used without the "substituted" modifier refers to a divalent saturated aliphatic group with one or two carbon atom as the point(s) of attachment, said carbon atom(s) forms part of one or more non-aromatic ring structures, a cyclo or cyclic structure, no carbon-carbon double or triple bonds, and no atoms other than carbon and hydrogen.

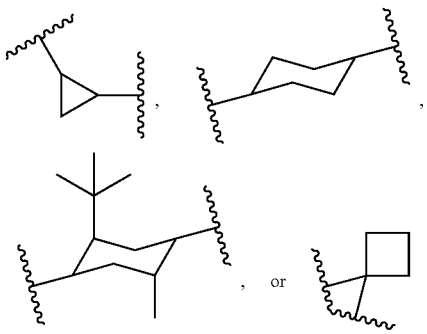

are non-limiting examples of cycloalkanediyl groups. A "cycloalkane" refers to the compound H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted cycloalkyl groups: —C(OH)(CH$_2$)$_2$,

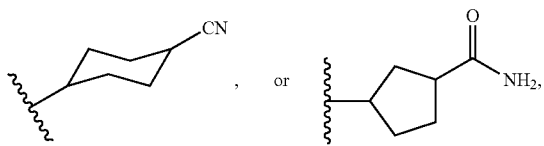 [SMILES: *C1CCC(C#N)CC1 ; *C1CCC(C(N)=O)C1]

The term "alkenyl" when used without the "substituted" modifier refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, and —CH=CHCH$_2$—, are non-limiting examples of alkenediyl groups. It is noted that while the alkenediyl group is aliphatic, once connected at both ends, this group is not precluded from forming part of an aromatic structure. The terms "alkene" and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups.

The term "cycloalkenyl" when used without the "substituted" modifier refers to a monovalent unsaturated aliphatic group with a carbon atom as the point of attachment, said carbon atom forms part of one or more non-aromatic ring structures, a cyclo or cyclic structure, at least one non-aromatic carbon-carbon double bond, no carbon-carbon triple bonds, and no atoms other than carbon and hydrogen. In some non-limiting examples of cycloalkenyl groups include

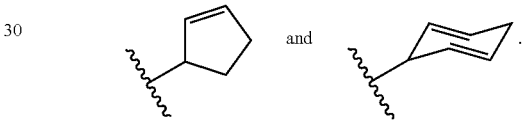

The term "cycloalkenediyl" when used without the "substituted" modifier refers to a divalent unsaturated aliphatic group with one or two carbon atom(s) as the point(s) of attachment, said carbon atom(s) forms part of one or more non-aromatic ring structures, a cyclo or cyclic structure, at least one non-aromatic carbon-carbon double bond, no carbon-carbon triple bonds, and no atoms other than carbon and hydrogen.

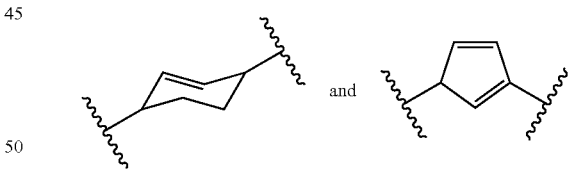

are non-limiting examples of cycloalkenediyl. It is noted that while the cycloalkenediyl group is aliphatic, once connected at both ends, this group is not precluded from forming part of an aromatic structure. The terms "cycloalkene" and refer to a compound having the formula H—R, wherein R is cycloalkenyl as this term is defined above. The term "olefin" is synonymous with the terms "alkene" or a "cycloalkane" as those terms are defined above. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. In some non-limiting examples of substituted cycloalkenyl include

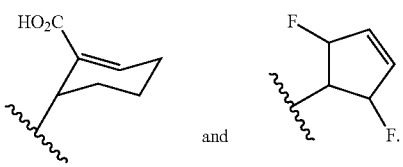 [SMILES: *C1CCCC=C1C(=O)O ; "and" ; *C1C(F)C=CC1F]

and

The term "alkynyl" when used without the "substituted" modifier refers to a monovalent unsaturated aliphatic group with a carbon atom as the point of attachment, a linear or branched, acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. An "alkyne" refers to the compound H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

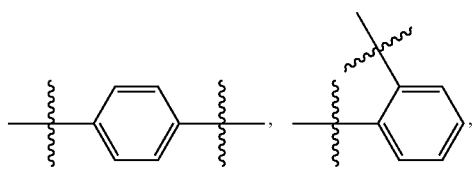

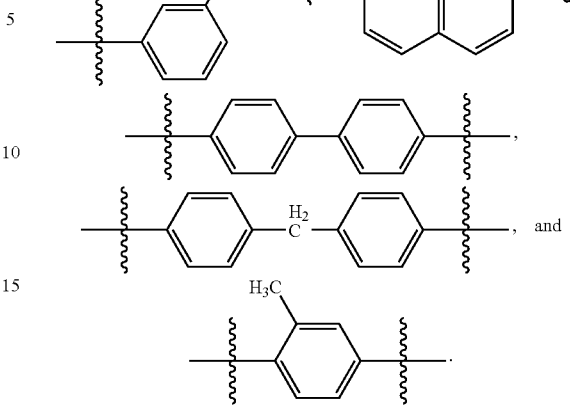

and

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

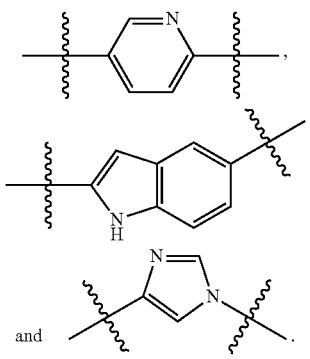

and

A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "heteroaralkyl" when used without the "substituted" modifier refers to the monovalent group -alkanediyl-heteroaryl, in which the terms alkanediyl and heteroaryl are each used in a manner consistent with the definitions provided above. Non-limiting examples of heteroaralkyls are: 2-pyridylmethyl and 2-indazolyl-ethyl. When the term heteroaralkyl is used with the "substituted" modifier one or more hydrogen atom from the alkanediyl and/or the heteroaryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Non-limiting examples of substituted heteroaralkyls are: (3-chloroquinolyl)-methyl, and 2-chloro-2-thienyl-eth-1-yl.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. The term "heterocycloalkanediyl" when used without the "substituted" modifier refers to an divalent cyclic group, with two carbon atoms, two nitrogen atoms, or one carbon atom and one nitrogen atom as the two points of attachment, said atoms forming part of one or more ring structure(s) wherein at least one of the ring atoms is nitrogen, oxygen or sulfur, and wherein the divalent group consists of no atoms other than carbon, hydrogen, nitrogen, oxygen and sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkanediyl groups include:

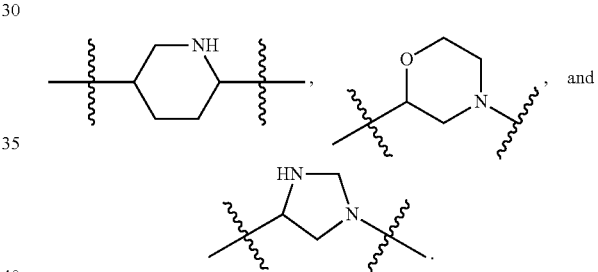

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$NH$_2$, or —C(O)OC(CH$_3$)$_3$ (tert-butyloxycarbonyl, BOC).

The term "acyl" when used without the "substituted" modifier refers to the group —C(O)R, in which R is a hydrogen, alkyl, cycloalkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can each independently be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "cycloalkylamino", "alkenylamino", "cycloalkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, cycloalkyl, alkenyl, cycloalkenyl, alkynyl, aryl, aralkyl, heteroaryl, heterocycloalkyl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl—NH—, or -alkanediyl—NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), and —OC(CH$_3$)$_3$ (tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkoxydiyl" refers to the divalent group —O-alkanediyl- , —O-alkanediyl—O—, or -alkanediyl—O-alkanediyl-. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane or cycloalkane, as defined above, wherein at least one of the hydrogen atoms has been replaced with an alkoxy or cycloalkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

A "reducing agent" in the context of this application is a compound which causes the reduction of a compound through the donation of an electron. A soft reducing agent is a reducing agent which contains electron delocalizing ligands which weaken the nucleophilic strength of the hydride. Some non-limiting examples of reducing agents are sodium borohydride, sodium triacetoxyborohydride, sodium cyanoborohydride, lithium aluminum hydride, diisobutylaluminum hydride, hydrogen gas, or metal hydride.

A "base" in the context of this application is a compound which has a lone pair of electron that can accept a proton. Non-limiting examples of a base can include triethylamine, a metal hydroxide, a metal alkoxide, a metal hydride, or a metal alkane. An alkyllithium or organolithium is a compound of the formula alkyl$_{(C \leq 12)}$—Li. A nitrogenous base is an alkylamine, dialkylamino, trialkylamine, nitrogen containing heterocycloalkane or heteroarene wherein the base can accept a proton to form a positively charged species. For example, but not limited to, a nitrogenous base could be 4,4-dimethylpyridine, pyridine, 1,8-diazabicyclo[5.4.0]undec-7-ene, diisopropylethylamine, or triethylamine. A metal alkoxide is an alkoxy group wherein rather than the oxygen atom which was the point of connectivity has an extra electron and thus a negative charge which is charged balanced by the metal ion. For example, a metal alkoxide could be a sodium tert-butoxide or potassium methoxide.

An "oxidizing agent" in the context of this application is a compound which causes the oxidation of a compound by accepting an electron. Some non-limiting examples of oxidizing agent are oxygen gas, peroxides, chlorite, hypochlorite, or a chromium compound such as pyridinium chlorochromate or hydrochromic acid.

A "metal" in the context of this application is a transition metal or a metal of groups I or II. In some embodiments, a metal is lithium, sodium, or potassium. In other embodiments, a metal is calcium or magnesium.

An "alkylaluminium" in the context of this application is a reagent which contains one, two, three, or four alkyl groups as that group is defined above to a central aluminum atom. Some non-limiting examples of alkylaluminiums are trimethylaluminum or tetramethylaluminium.

A "linker" in the context of this application is divalent chemical group which may be used to join one or more molecules to the compound of the instant disclosure. In some embodiments, the linker contains a reactive functional group, such as a carboxyl, an amide, a amine, a hydroxy, a mercapto, an aldehyde, or a ketone on each end that be used to join one or more molecules to the compounds of the instant disclosure. In some non-limiting examples, —CH$_2$CH$_2$CH$_2$CH$_2$—, —C(O)CH$_2$CH$_2$CH$_2$—, —OCH$_2$CH$_2$NH—, —NHCH$_2$CH$_2$NH—, and —(OCH$_2$CH$_2$)$_n$— wherein n is between 1-1000, are linkers.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Synthesis of Viridicatumtoxin and Analogs Thereof

Scheme 1: Synthesis of viridicatumtoxin B(1).[a]

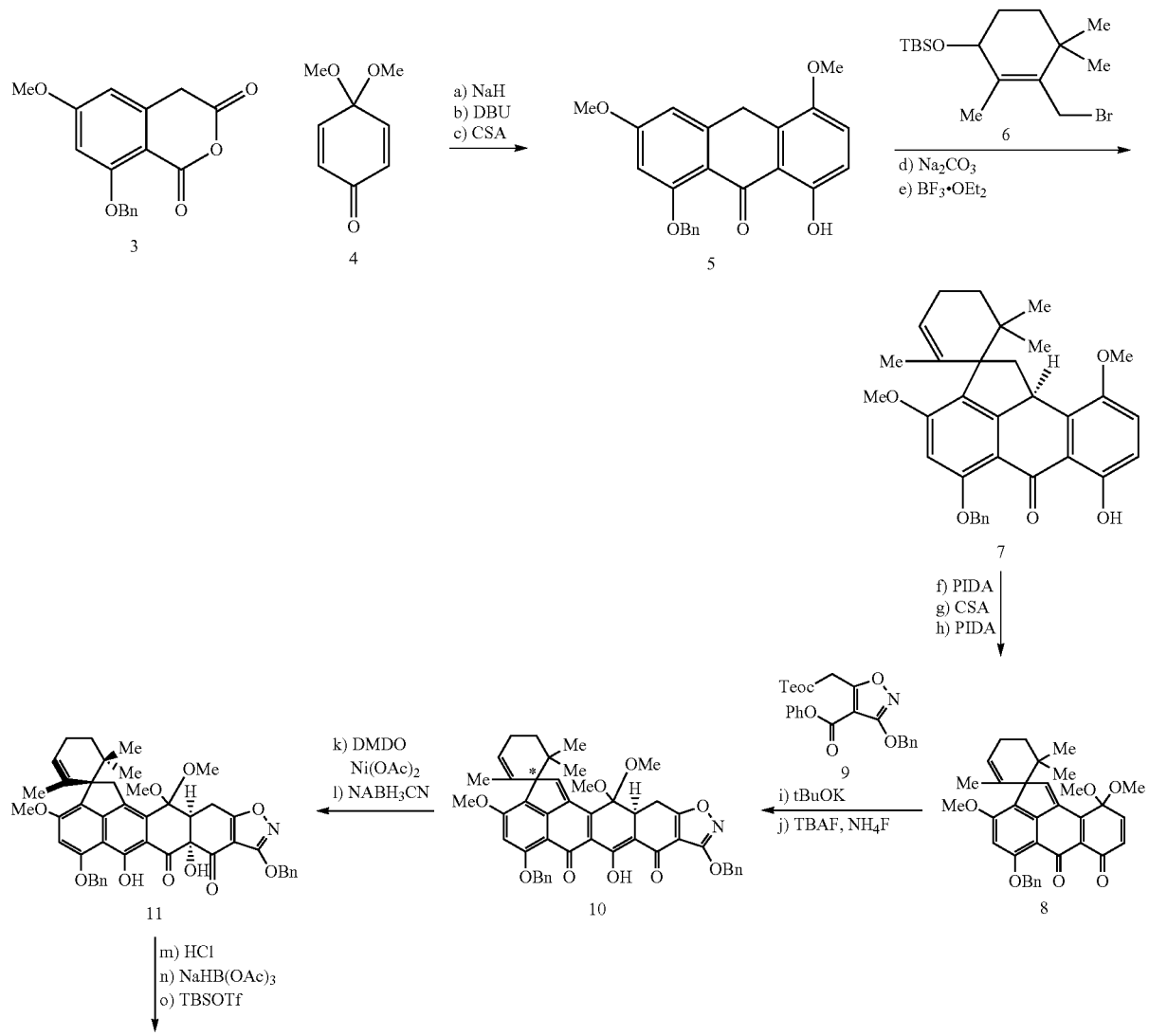

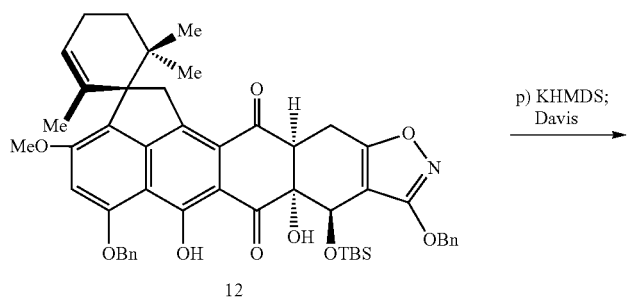

12 p) KHMDS; Davis

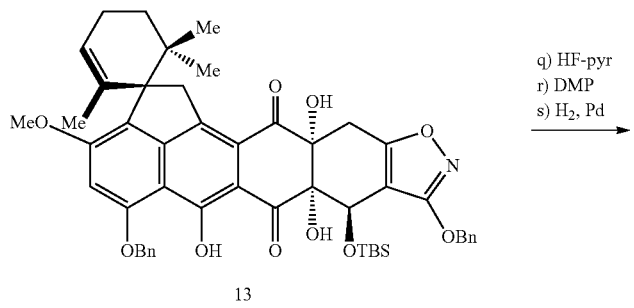

13 q) HF·pyr
r) DMP
s) H₂, Pd

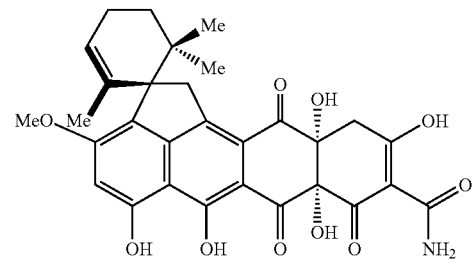

1

*Reagents and conditions: a) 4 (3.0 equiv), NaH (3.0 equiv), THF, 0° C., 45 min; then 25° C., 1 h; b) DBU (5.0 equiv). toluene, 65° C., 4.5 h, 54% for 2 steps; c) CSA (0.02 equiv), CH₂Cl₂, 25° C., 30 min, 99%; d) 6 (1.1 equiv), Na₂CO₃ (10 equiv), DMF, 25° C., 1 h, 77%, d.r. ca. 1:1; e) BF₃·OEt₂ (0.15 equiv), CH₂Cl₂, 0° C., 20 min, 73%; f) PIDA (1.2 equiv), MeOH:CH₂Cl₂ 1:1, 0→25° C., 1 h; g) CSA (0.07 equiv), CH₂Cl₂, 0° C., 5 min, 85% for 2 steps; h) PIDA (1.2 equiv), MeOH:CH₂Cl₂ 10:1, 25° C., 1.5 h, 90%; i) 8 (1.1 equiv), tBuOK (1.2 equiv), toluene, 25°C., 15 min, 91%, d.r. ca. 2:1; j) TBAF (10 equiv), NH₄F (20 equiv), degassed THF, 25° C., 5 min, 86%; k) Ni(acac)₂ (0.2 equiv), DMDO (5.1 equiv), CH₂Cl₂, -78→-60° C., 6.5 h, 36%, 60% brsm, 50% after one recycle; l) NaCNBH₃ (10 equiv), THF, -78→60° C., 90 min, 39% for 11, 19% for 15-epi-11, chromatographically separated; m) 2N aq. HCl:THF 1:10, 25° C., 5 h, quant.; n) NaBH(OAc)₃ (1.2 equiv), EtOAc:acetone 1:1, 40° C., 105 min, 47%; o) TBSOTf (40 equiv), 2,6-lutidine (60 equiv), CH₂Cl₂, 0→25° C., 1 h, 61%; p) KHMDS (3.4 equiv), THF, -78° C., 1 h; then Davis ox. (3.9 equiv), -78° C., 1.7 h, 20% + 45% recovered 12; q) HF·py (excess), MeCN, 0→50° C., 25 h, 61%; r) DMP (3.0 equiv), DCE, 0→50° C., 7.5 h, 66%; s) H₂, Pd black (4.9 equiv), 1,4-dioxane:MeOH 1:1, 25° C., 8 min, 98%. Abbreviations: DBU = 1,8-diazabicyclo[5.4.0]undec-7-ene, CSA = (±)-camphor-10-sulfonic acid, PIDA = iodobenzene diacetate; TBAF = tetra-n-butylammonium fluoride; acac = acetylacetonate, DMDO = dimethyldioxirane; TBSOTf = tert-butyldimethylsilyl trifluoromethanesulfonate; KHMDS = potassium hexamethyldisilazide, Davis ox. = (±)-trans-2-(phenylsulfonyl)-3-phenyloxaziridine, py = pyridine, DMP = Dess-Martin periodinane, DCE = 1,2-dichloroethane.

Scheme 2: Synthesis of viridicatumtoxin analogs V2, V3 and V4.[a]

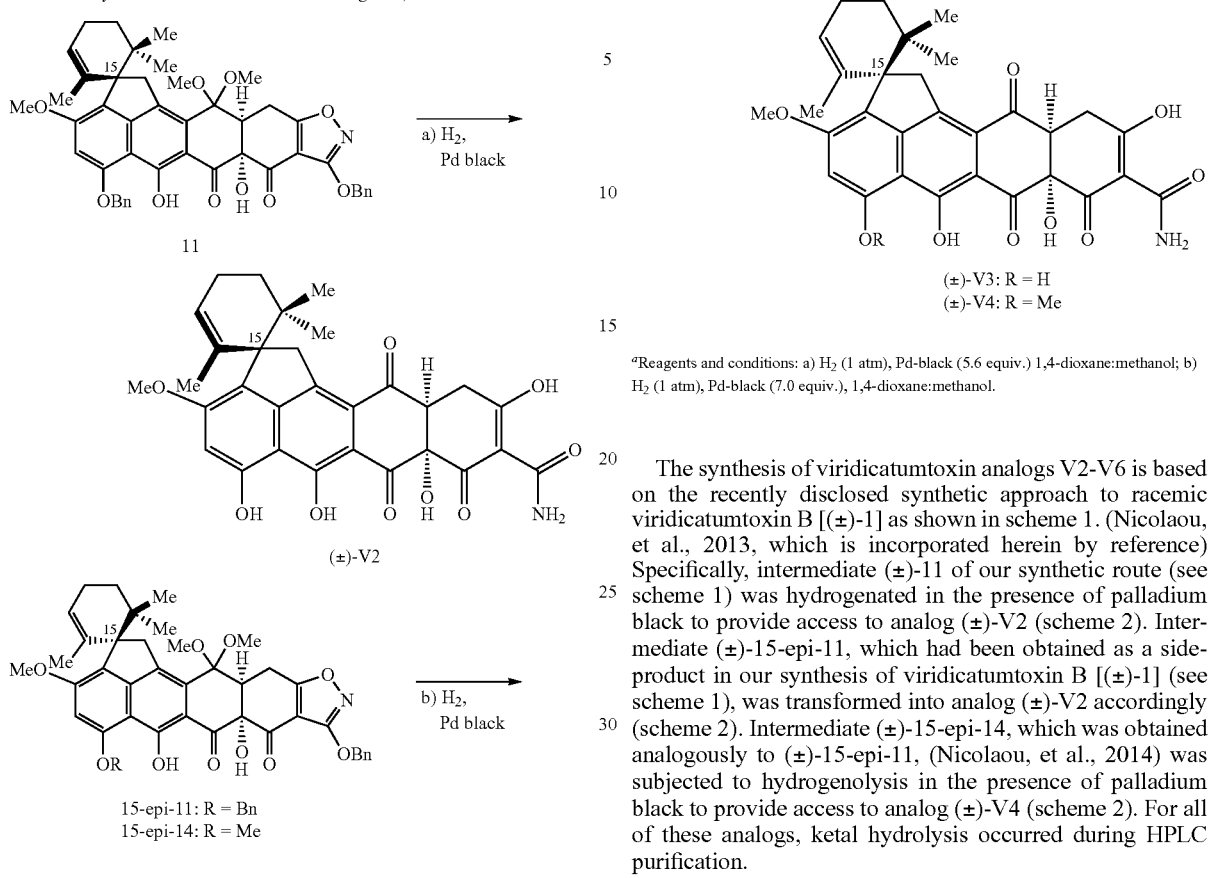

(±)-V3: R = H
(±)-V4: R = Me

[a]Reagents and conditions: a) $H_2$ (1 atm), Pd-black (5.6 equiv.) 1,4-dioxane:methanol; b) $H_2$ (1 atm), Pd-black (7.0 equiv.), 1,4-dioxane:methanol.

The synthesis of viridicatumtoxin analogs V2-V6 is based on the recently disclosed synthetic approach to racemic viridicatumtoxin B [(±)-1] as shown in scheme 1. (Nicolaou, et al., 2013, which is incorporated herein by reference) Specifically, intermediate (±)-11 of our synthetic route (see scheme 1) was hydrogenated in the presence of palladium black to provide access to analog (±)-V2 (scheme 2). Intermediate (±)-15-epi-11, which had been obtained as a side-product in our synthesis of viridicatumtoxin B [(±)-1] (see scheme 1), was transformed into analog (±)-V2 accordingly (scheme 2). Intermediate (±)-15-epi-14, which was obtained analogously to (±)-15-epi-11, (Nicolaou, et al., 2014) was subjected to hydrogenolysis in the presence of palladium black to provide access to analog (±)-V4 (scheme 2). For all of these analogs, ketal hydrolysis occurred during HPLC purification.

Scheme 3: Synthesis of viridicatumtoxin analogs V5 and V6.[a]

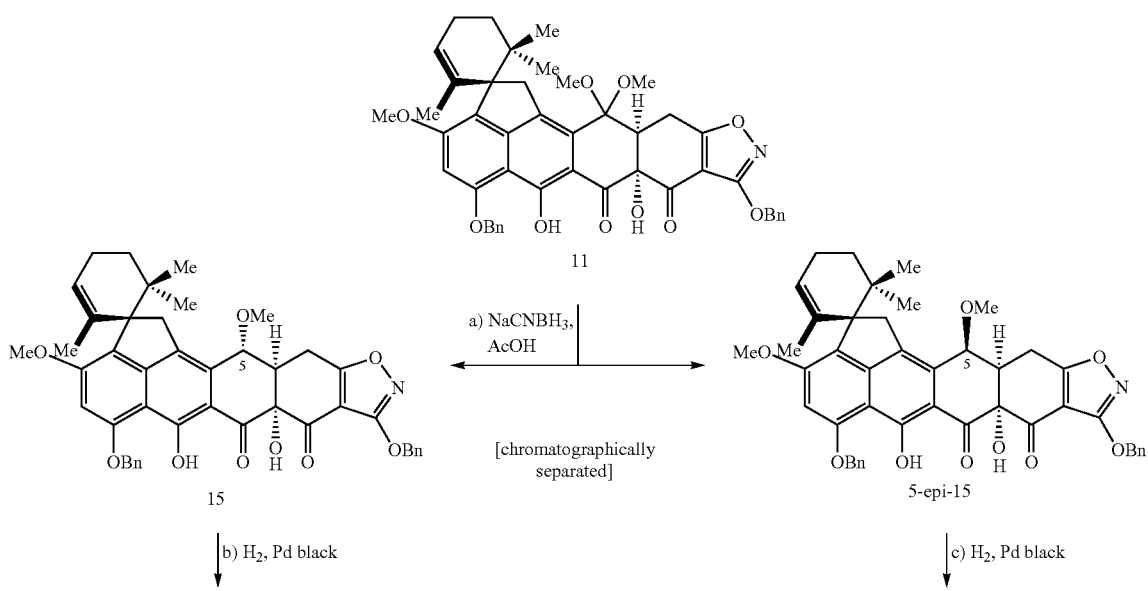

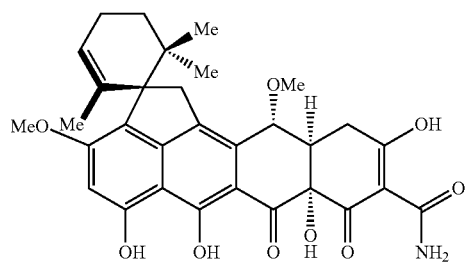

V5

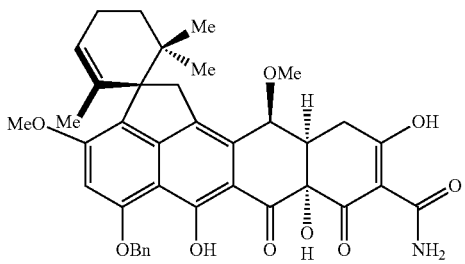

V6

[a]Reagents and conditions: a) NaCNBH$_3$ (4.0 equiv), AcOH, 25° C., 25 minutes, 31% for 15, 27% for 5-epi-15; b) H$_2$ balloon, Pd black (4.1 equiv), THF:MeOH 1:1, 25° C., 10 min, 96%; c) H$_2$, Pd black (4.5 equiv), THF:MeOH 1:1, 25° C., 10 min, quant.

The synthesis of analogs (±)-V5 and (±)-V6 commenced with intermediate (±)-11 (scheme 3). Reduction with NaCNBH$_3$ (4.0 equiv.) in acetic acid led to a mixture of methyl ethers (±)-15 and (±)-5-epi-15, which was chromatographically separated. Intermediate (±)-15 was then transformed into (±)-V5 through hydrogenolysis in the presence of palladium black (scheme 3). (±)-V6 was obtained from (±)-5-epi-15 accordingly (scheme 3).

Example 2—General Methods and Materials

All reactions were carried out under an argon atmosphere unless otherwise noted. Methylene chloride, tetrahydrofuran, toluene, methanol, dimethylformamide, acetonitrile, diisopropylamine, and triethylamine were dried prior to use by passage through an activated alumina column unless otherwise noted (Pangborn, et al., 1996). Anhydrous acetone, ethyl acetate, and 1,2-dichloro-ethane were purchased from commercial suppliers and stored under argon. Yields refer to chromatographically and spectroscopically ($^1$H NMR) homogenous material, unless otherwise stated.

Reactions were monitored by thin-layer chromatography (TLC) carried out on 0.25 mm E. Merck silica gel plates (60E-254) and were visualized using UV light and an ethanolic solution of phosphomolybdic acid and cerium sulfate or an aqueous solution of potassium permanganate. Flash column chromatography using E. Merck silica gel (60, particle size 0.040-0.063 mm) was performed as described by Still, et al. (1978). NMR spectra were recorded on a Bruker DRX-600 equipped with a 5 mm DCH cryoprobe, Bruker DRX-500, Bruker AV-400, or Varian INOVA-400 instrument and calibrated using residual undeuterated solvent for $^1$H NMR [$\delta_H$=7.26 (CHCl$_3$), 7.16 (C$_6$D$_5$H), 2.05 (D$_5$H-acetone), 2.50 (D$_5$H-DMSO), and 5.32(CDHCl$_2$) ppm] and $^{13}$C deuterated solvent for $^{13}$C NMR [$\delta_C$=77.16 (CDCl$_3$), 128.06 (C$_6$D$_6$), 206.68 (d$_6$-acetone), and 53.84 (CD$_2$Cl$_2$) ppm] as an internal reference at 298 K (Fulmer, et al., 2010). The following abbreviations were used to designate the multiplicities: s=singlet, d=doublet, t=triplet, q=quartet, m=multiplet, b=broad, ap=apparent.

ATR-Infrared (IR) spectra were recorded on a Perkin-Elmer 100 series FT-IR spectrometer. High-resolution mass spectra (HRMS) were recorded on an Agilent LC/MSD/TOF mass spectrometer using ESI (electrospray ionization) or a Shimadzu Ion Trap-TOF using ESI. Melting points were recorded on a Fisher-Johns 12-144 melting point apparatus or a Thomson Hoover uni-melt capillary melting point apparatus. X-Ray crystallographic structures were collected using a Bruker Smart-APEX instrument (CCD detector) or a Bruker Kappa APEX-II instrument (CCD detector).

Preparative HPLC separations were performed using a Waters 2767 prep LC system equipped with a Waters Atlantis prep T3 OBD column (16×150 mm, 5 µm particle size) and monitored using a Waters 2996 photodiode array detector.

Example 3—Compound Characterization

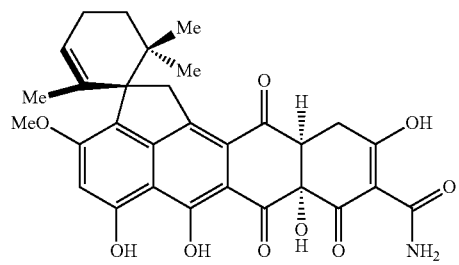

Viridicatumtoxin analog V2: To a stirred solution of (±)-11 (30 mg, 0.048 mmol, 1.0 equiv) in 1,4-dioxane:MeOH (4 mL, 1:1) was added Pd black (28 mg, 0.27 mmol, 5.6 equiv) under argon. The flask headspace was exchanged for H$_2$, and the reaction mixture was stirred for 10 minutes at room temperature. The flask headspace was re-exchanged for argon, and the mixture was filtered through Celite® and concentrated (crude product: 30 mg). A portion of this material was purified by reverse-phase prep-HPLC [Waters Atlantis prep T3 OBD, 16×150 mm, 5 µm particle size, 20 mL/min, 50% MeCN in H$_2$O (0→15 min), then ramp to 70% MeCN (15→25 min), 0.07% TFA buffer, λ=288 nm]: $t_R$=17.59 min, to provide pure (±)-V2 (9.5 mg, 17 µmol). (±)-V2: $R_f$=0.1 (silica gel, MeOH:CH$_2$Cl$_2$ 1:19); FT-IR (neat) $v_{max}$=3435, 2921, 1685, 1623, 1585, 1492, 1448, 1399, 1281, 1259, 1198, 1162, 1133, 1069, 904, 733 cm$^{-1}$; $^1$H NMR (CDCl$_3$, 600 MHz) δ=18.21 (s, 1 H), 14.49 (s, 1 H), 9.02 (s, 1 H), 8.71 (s, 1 H), 6.79 (s, 1 H), 5.73 (s, 1 H), 5.50 (s, 1 H), 4.82 (s, 1 H), 3.88 (s, 3 H), 3.71 (d, J=20.1 Hz, 1 H), 3.56 (t, J=4.4 Hz, 1 H), 3.35 (dd, J=18.0, 3.9 Hz, 1 H), 3.20 (d, J=20.1 Hz, 1 H), 3.15 (dd, J=18.0, 5.0 Hz, 1 H), 2.20 (m, 1 H), 2.04 (m, 1 H), 1.81 (td, J=12.6, 6.1 Hz, 1 H), 1.45 (s, 3 H), 1.32 (dd, J=12.6, 6.1 Hz, 1 H), 0.90 (s, 3 H), 0.34 (s, 3 H) ppm; $^{13}$C NMR (CDCl$_3$, 151 MHz) δ=196.6, 196.5, 192.6, 189.8, 173.7, 163.5, 160.9, 158.1, 146.7, 143.6, 135.9, 127.0, 121.7, 120.7, 106.9, 106.9, 102.4, 99.8, 77.4, 60.4, 55.8, 50.4, 45.6, 38.5, 34.1, 29.3, 25.5, 24.3, 22.9, 21.0 ppm; HRMS (ESI) calcd for $C_{34}H_{29}NO_9H^+$ [M+H$^+$] 548.1915, found 548.1902.

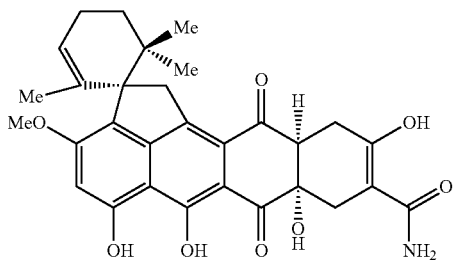

Viridicatumtoxin analog V3: To a stirred solution of (±)-15-epi-11 (44 mg, 0.057 mmol, 1.0 equiv) in 1,4-dioxane:MeOH (5 mL, 1:1) was added Pd black (42 mg, 0.40 mmol, 7 equiv) under argon. The flask headspace was exchanged for $H_2$, and the reaction mixture was stirred for 10 minutes at room temperature. The flask headspace was re-exchanged for argon, and the mixture was filtered through Celite® and concentrated (crude product: 40 mg). A portion of this material was purified by reverse-phase prep-HPLC [Waters Atlantis prep T3 OBD, 16×150 mm, 5 μm particle size, 20 mL/min, 50% MeCN in $H_2O$ (0→15 min), then ramp to 70% MeCN (15→25 min), 0.07% TFA buffer, λ=288 nm]: $t_R$=17.51 min, to provide pure (±)-V3 (11 mg, 20 μmol). (±)-V3: $R_f$=0.1 (silica gel, MeOH:CH$_2$Cl$_2$ 1:19); FT-IR (neat) $v_{max}$=3414, 2923, 1681, 1622, 1585, 1452, 1401, 1283, 1261, 1203, 1134, 1070, 909, 730 cm$^{-1}$; $^1$H NMR (CDCl$_3$, 600 MHz) δ=18.22 (s, 1 H), 14.60 (s, 1 H), 9.05 (s, 1 H), 8.74 (s, 1 H), 6.79 (s, 1 H), 5.73 (s, 1 H), 5.49 (s, 1 H), 5.47 (bs, 1 H), 3.88 (s, 3 H), 3.85 (m, 1 H), 3.44 (t, J=4.6 Hz, 1 H), 3.36 (dd, J=18.1, 2.3 Hz, 1 H), 3.14 (dd, J=18.1, 5.0 Hz, 1 H), 3.08 (d, J=20.0 Hz, 1 H), 2.19 (m, 1 H), 2.04 (m, 1 H), 1.83 (td, J=12.6, 6.2 Hz, 1 H), 1.41 (s, 3 H), 1.36 (dd, J=12.6, 5.9 Hz, 1 H), 0.91 (s, 3 H), 0.39 (s, 3 H) ppm; $^{13}$C NMR (CDCl$_3$, 151 MHz) δ=196.5, 196.3, 192.6, 189.8, 173.6, 164.0, 161.0, 158.1, 146.9, 143.6, 135.9, 127.1, 121.8, 120.6, 107.0, 106.9, 102.4, 99.9, 77.3, 60.4, 55.8, 50.5, 45.4, 38.5, 34.1, 29.5, 25.5, 24.6, 23.0, 20.8 ppm; HRMS (ESI) calcd for $C_{30}H_{29}NO_9H^+$ [M+H$^+$] 548.1915, found 548.1894.

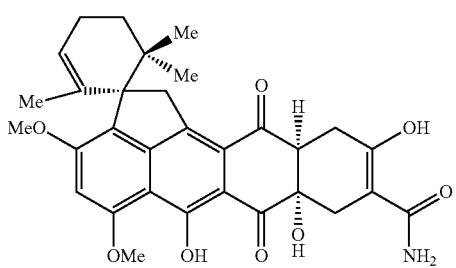

Viridicatumtoxin analog V4: To a stirred solution of (±)-15-epi-14 (40 mg, 0.058 mmol, 1.0 equiv) in 1,4-dioxane:MeOH (5 mL, 1:1) was added Pd black (43 mg, 0.40 mmol, 7 equiv) under argon. The flask headspace was exchanged for $H_2$, and the reaction mixture was stirred for 10 minutes at room temperature. The flask headspace was re-exchanged for argon, and the mixture was filtered through Celite® and concentrated (crude product: 44 mg). A portion of this material was purified by reverse-phase prep-HPLC [Waters Atlantis prep T3 OBD, 16×150 mm, 5 μm particle size, 20 mL/min, 50% MeCN in $H_2O$ (0→15 min), then ramp to 70% MeCN (15→25 min), 0.07% TFA buffer, λ=288 nm]: $t_R$=14.25 min, to provide pure (±)-V4 (8.8 mg, 16 μmol). (±)-V4: $R_f$=0.1 (silica gel, MeOH: CH$_2$Cl$_2$ 1:19); FT-IR (neat) $v_{max}$=3400, 2939, 1683, 1585, 1466, 1400, 1342, 1285, 1216, 1187, 1163, 1132, 1068, 914, 824, 731 cm$^{-1}$; $^1$H NMR (CDCl$_3$, 600 MHz) δ=18.19 (s, 1 H), 14.20 (s, 1 H), 9.06 (s, 1 H), 6.72 (s, 1 H), 5.72 (s, 1 H), 5.49 (s, 1 H), 4.93 (s, 1 H), 4.09 (s, 3 H), 3.94 (s, 3 H), 3.86 (d, J=19.9 Hz, 1 H), 3.44 (t, J=4.5 Hz, 1 H), 3.36 (dd, J=18.1, 4.0 Hz, 1 H), 3.13 (dd, J=18.1, 5.1 Hz, 1 H), 3.08 (d, J=19.9 Hz, 1 H), 2.20 (m, 1 H), 2.05 (m, 1 H), 1.85 (td, J=12.5, 6.1 Hz, 1 H), 1.42 (s, 3 H), 1.34 (dd, J=12.5, 6.2 Hz, 1 H), 0.91 (s, 3 H), 0.37 (s, 3 H) ppm; $^{13}$C NMR (CDCl$_3$, 151 MHz) δ=196.2, 196.1, 193.1, 190.0, 173.6, 165.0, 160.4, 159.6, 148.1, 142.1, 136.2, 126.9, 121.6, 121.5, 110.0, 107.9, 99.9, 98.1, 77.2, 59.7, 56.8, 55.6, 50.5, 45.2, 38.5, 34.0, 29.4, 25.5, 24.5, 23.0, 20.8 ppm; HRMS (ESI) calcd for $C_{31}H_{31}NO_9H^+$ [M+H$^+$] 562.2072, found 562.2082.

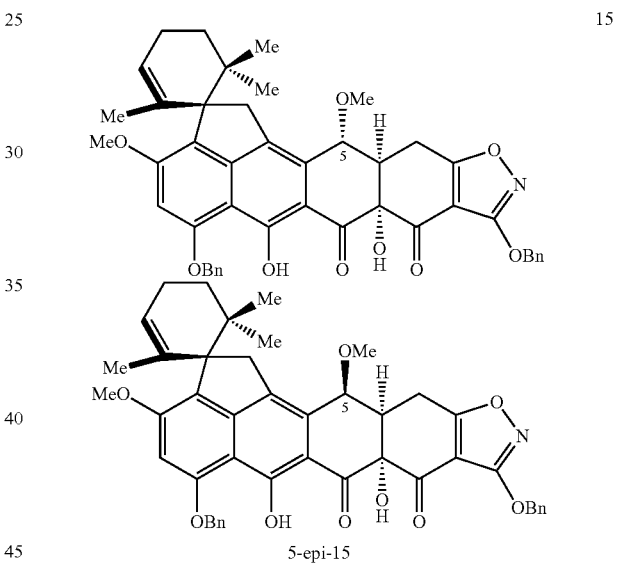

(±)-15 and (±)-5-epi-15: This reaction was run twice in parallel. To two separate batches of substrate (±)-11 (25 mg each, 0.032 mmol each, 1.0 equiv each) was added solid NaCNBH$_3$ (8 mg each, 0.13 mmol each, 4.0 equiv each). Then, AcOH (2.5 mL each) was rapidly injected into the reaction vessel, and the mixture was vigorously stirred at room temperature for 25 minutes. The two reaction mixtures were combined for work up by pouring them into water (25 mL). Brine (5 mL) was added, and the mixture was extracted with EtOAc (35 mL). The organic phase was washed with additional brine (2×25 mL), and the organic layer was dried over Na$_2$SO$_4$, filtered and concentrated. The crude residue was purified by preparative TLC (silica gel, 10% acetone: toluene) to provide (±)-15 (26 mg, not pure) and isomer (±)-5-epi-15 (13 mg, 0.017 mmol, 27%, yellow foam). Product (±)-15 was further purified by preparative TLC (silica gel, 5% EtOAc:CH$_2$Cl$_2$) to give pure compound (±)-15 (15 mg, 0.020 mmol, 31%) as a yellow foam.

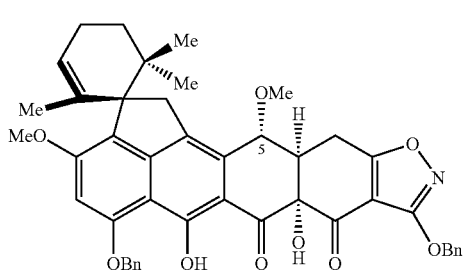

15

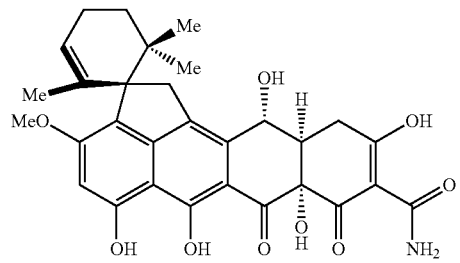

(±)-15: $R_f$=0.6 (silica gel, acetone:toluene 3:17); FT-IR (neat) $v_{max}$=3397, 2916, 1702, 1591, 1512, 1481, 1448, 1405, 1371, 1339, 1319, 1254, 1195, 1143, 1109, 1081, 1032, 986, 914, 812, 734, 695 cm$^{-1}$; $^1$H NMR (C$_6$D$_6$, 500 MHz) δ=15.00 (s, 1 H), 7.58-7.55 (m, 2 H), 7.28-7.25 (m, 2 H), 7.24-7.20 (m, 2 H), 7.12 (m, 1 H), 7.05-6.98 (m, 3 H), 6.26 (s, 1 H), 5.56 (s, 1 H), 5.14 (d, J=12.2 Hz, 1 H, AB system), 5.10 (d, J=12.2 Hz, 1 H, AB system), 4.89 (ap s, 3 H), 4.34 (d, J=8.6 Hz, 1 H), 3.56 (d, J=17.6 Hz, 1 H), 3.26 (s, 3 H), 2.85 (s, 3 H), 2.83 (m, 1 H), 2.77-2.64 (m, 3 H), 2.31 (m, 1 H), 2.04 (m, 1 H), 1.91 (ddd, J=12.3, 12.3, 6.1 Hz, 1 H), 1.65 (s, 3 H), 1.37 (dd, J=13.2, 6.0 Hz, 1 H), 1.15 (s, 3 H), 0.69 (s, 3 H) ppm; $^{13}$C NMR (C$_6$D$_6$, 126 MHz) δ=197.0, 185.4, 180.3, 168.6, 166.3, 159.7, 158.8, 149.2, 137.9, 137.2, 135.7, 132.5, 128.9, 128.7, 128.6, 128.51, 128.48, 127.2, 127.0, 122.5, 121.1, 109.2, 109.0, 106.2, 97.5, 78.6, 75.3, 72.3, 71.2, 59.3, 54.9, 54.7, 42.8, 42.6, 38.7, 34.4, 26.1, 24.6, 23.4, 22.7, 21.5 ppm; HRMS (ESI) calcd for C$_{45}$H$_{43}$NO$_9$Na$^+$ [M+Na$^+$] 764.2830, found 764.2853.

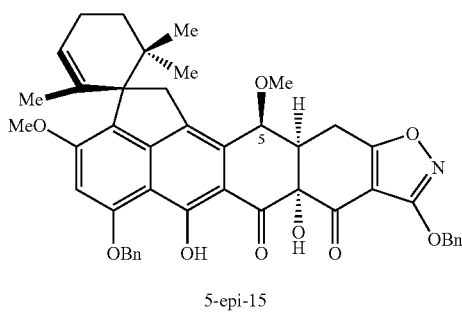

5-epi-15

(±)-5-epi-15: $R_f$=0.7 (silica gel, acetone:toluene 3:17); FT-IR (neat) $v_{max}$=3447, 2917, 1708, 1593, 1514, 1485, 1449, 1407, 1373, 1345, 1317, 1259, 1192, 1138, 1115, 1086, 994, 913, 813, 735, 696 cm$^{-1}$; $^1$H NMR (C$_6$D$_6$, 500 MHz)* δ=15.33 (s, 1 H), 7.57-7.54 (m, 2 H), 7.35-7.32 (m, 2 H), 7.22-7.18 (m, 2 H), 7.12-7.06 (m, 3 H), 7.04 (m, 1 H), 6.25 (s, 1 H), 5.59 (s, 1 H), 5.25 (d, J=12.1 Hz, 1 H, AB system), 5.13 (d, J=12.1 Hz, 1 H, AB system), 4.91 (s, 2 H), 4.75 (bs, 1 H), 3.44 (bs, 1 H), 3.36 (m, 1 H), 3.24 (s, 3 H), 2.91 (bs, 3 H), 2.64-2.56 (m, 2 H), 2.38-2.25 (m, 2 H), 2.10-1.97 (m, 2 H), 1.78 (s, 3 H), 1.38 (dd, J=12.5, 6.0 Hz, 1 H), 1.12 (s, 3 H), 0.59 (s, 3 H) ppm; $^{13}$C NMR (C$_6$D$_6$, 126 MHz)* δ=167.5, 159.7, 158.9, 138.0, 137.3, 135.8, 132.5, 128.9, 128.7, 128.63, 128.56, 127.1, 126.4, 122.5, 121.2, 108.6, 106.7, 97.5, 72.4, 71.2, 59.1, 56.3, 54.8, 38.5, 34.4, 26.0, 24.3, 23.5, 21.5 ppm; HRMS (ESI) calcd for C$_{45}$H$_{43}$NO$_9$Na$^+$ [M+Na$^+$] 764.2830, found 764.2832.
*Due to signal broadening, 1 proton signal and 12 carbon signals could not be identified.

Viridicatumtoxin analog V5: Following conditions similar to those of Stork, et al. (1996), Pd black (12 mg, 0.11 mmol, 4.1 equiv) was added to a stirred solution of (±)-15 (20 mg, 0.027 mmol, 1.0 equiv) in THF:MeOH (1.2 mL, 1:1) under argon. The flask headspace was exchanged for H$_2$, and the reaction mixture was stirred for 10 minutes at room temperature. The flask headspace was re-exchanged for argon, and the mixture was filtered through cotton and concentrated to give (±)-V5 (15 mg, 0.026 mmol, 96%) as a yellow powder. (±)-V5: $R_f$=0.1 (silica gel, MeOH:CH$_2$Cl$_2$ 1:19); FT-IR (neat) $v_{max}$=3399, 2917, 1625, 1595, 1490, 1471, 1451, 1401, 1309, 1273, 1200, 1084, 909, 732 cm$^{-1}$; $^1$H NMR (CDCl$_3$, 600 MHz) δ=18.00 (s, 1 H), 15.12 (s, 1 H), 9.25 (bs, 1 H), 8.80 (s, 1 H), 6.63 (s, 1 H), 5.91 (bs, 1 H), 5.49 (bs, 1 H), 5.16 (bs, 1 H), 4.39 (d, J=4.5 Hz, 1 H), 3.85 (s, 3 H), 3.57 (s, 3 H), 3.36 (d, J=17.5 Hz, 1 H), 3.13 (m, 1 H), 2.88 (d, J=17.5 Hz, 1 H), 2.85 (dd, J=18.9, 5.4 Hz, 1 H), 2.58 (dd, J=18.9, 10.0 Hz, 1 H), 2.22 (m, 1 H), 2.04 (m, 1 H), 1.77 (ddd, J=12.7, 12.7, 6.1 Hz, 1 H), 1.48 (s, 3 H), 1.38 (dd, J=12.7, 6.2 Hz, 1 H), 0.93 (s, 3 H), 0.50 (s, 3 H) ppm; $^{13}$C NMR (CDCl$_3$, 151 MHz) δ=195.0, 194.0, 191.5, 173.2, 166.1, 160.5, 158.2, 147.6, 137.1, 135.7, 123.5, 122.5, 121.2, 106.4, 105.7, 100.6, 99.7, 76.7, 76.5, 60.0, 57.1, 55.6, 41.9, 38.4, 38.0, 34.2, 32.8, 25.8, 24.3, 23.0, 21.1 ppm; HRMS (ESI) calcd for C$_{31}$H$_{33}$NO$_9$Na$^+$ [M+Na$^+$] 586.2048, found 586.2045.

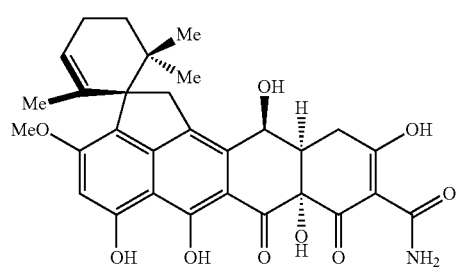

Viridicatumtoxin analog V6: Following conditions similar to those of Stork, et al., (1996), Pd black (8.6 mg, 0.081 mmol, 4.5 equiv) was added to a stirred solution of (±)-5-epi-15 (13 mg, 0.018 mmol, 1.0 equiv) in THF:MeOH (1.0 mL, 1:1) under argon. The flask headspace was exchanged for H$_2$, and the reaction mixture was stirred for 10 minutes at room temperature. The flask headspace was re-exchanged for argon, and the mixture was filtered through cotton and concentrated to give (±)-V6 (10 mg, 0.018 mmol, quant.) as a yellow powder. (±)-V6: $R_f$=0.1 silica gel, MeOH:CH$_2$Cl$_2$ 1:19); FT-IR (neat) $v_{max}$=3419, 2921, 1626, 1594, 1490, 1471, 1450, 1404, 1301, 1201, 1139, 1088, 907, 733 cm$^{-1}$; $^1$H NMR (CDCl$_3$, 600 MHz) δ=17.94 (s, 1 H), 15.34 (s, 1 H), 9.11 (s, 1 H), 8.84 (s, 1 H), 6.60 (s, 1 H), 5.85 (s, 1 H), 5.49 (s, 1 H), 5.00 (s, 1 H), 4.86 (s, 1 H), 3.85 (s, 3 H), 3.52

(bs, 3 H), 3.22 (d, J=17.9 Hz, 1 H), 3.13 (d, J=17.9 Hz, 1 H), 3.10 (m, 1 H), 2.92 (m, 1 H), 2.60 (dd, J=19.6, 10.9 Hz, 1 H), 2.22 (m, 1 H), 2.03 (m, 1 H), 1.82 (td, J=12.6, 6.1 Hz, 1 H), 1.54 (s, 3 H), 1.32 (dd, J=12.6, 6.1 Hz, 1 H), 0.89 (s, 3 H), 0.42 (s, 3 H) ppm; $^{13}$C NMR (CDCl$_3$, 151 MHz) δ=195.2, 194.8 (b), 192.1, 173.0, 166.6, 160.6, 158.1, 148.2, 137.6, 134.2, 124.2, 122.1, 120.8, 106.9, 105.3, 100.7, 99.2, 76.6, 75.6, 59.4, 57.0, 55.6, 43.9, 39.2 (b), 38.3, 34.1, 30.8 (b), 25.7, 24.1, 23.0, 21.2 ppm; HRMS (ESI) calcd for $C_{31}H_{33}NO_9Na^+$ [M+Na$^+$] 586.2048, found 586.2036.

Example 4: Biological Activity

A. Bacterial Strains and Growth Media:

Four clinical strains were used for these studies, *Enterococcus faecalis* S613, *Enterococcus faecium* isolate 105, Methicillin-Resistant *Staphylococcus aureus* 371 (MRSA 371) and *Acinetobacter baumannii* AB210. *Enterococcus* strains were cultured in 80% Lysogeny Broth (LB) & 20% Brain Heart Infusion (BHI). MRSA 371 and AB210 were cultured in 100% LB.

B. Minimal Inhibitory Concentration (MIC) Assays:

Micro-broth MIC assays were performed in triplicate using 96-well plates. Wells were filled with 150 μL of broth media and inoculated with 2 μL of stationary phase culture. The concentration of the test antibiotics increased in 2-fold increments and ranged from 0.25-128 μg/mL. Plates were incubated overnight at 37° C. and the MICs were defined as the lowest drug concentration that had no growth after 16-24 hours.

Biological Evaluation of Analogs

The minimum inhibitory concentrations against both selected Gram-positive and Gram-negative strains were determined for analogs V2-V6 and the results are shown in table 1.

TABLE 1

Minimum Inhibitory Concentration (MIC) data of compounds against Gram-positive and Gram-negative bacteria and comparison with selected literature data[a]

| | Gram-(+) | | | Gram-(−) |
|---|---|---|---|---|
| | *E. faecalis* S613 | *E. faecium* 501 | MRSA 371 | *A. baumannii* AB210 |
| (±)-1 | 1 | 0.5 | 4 | 64 |
| (+)-2 | 1 | 1 | 4 | 64 |
| (±)-V2 | 0.5 | 0.5 | 2 | 64 |
| (±)-V3 | 4 | 2 | 8 | 64 |
| (±)-V4 | 4 | 4 | 4 | 64 |
| (±)-V5 | 1 | 1 | 8 | 64 |
| (±)-V6 | 0.5 | 0.5 | 2 | 64 |

[a]MIC assays were run in triplicate; data are given in units of μg/mL.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

V. References

The following references, to the extent that they provide exemplary procedural or other details supplementary to those set forth herein, are specifically incorporated herein by reference:

JP 06-40995
WO 2009/008906
Anderson, N. G., *Practical Process Research & Development—A Guide For Organic Chemists*, 2$^{nd}$ ed., Academic Press, New York, 2012.
Breinholt, et al., *Acta Chem. Scand.,* 51:855-860, 1997.
Brubaker and Myers, *Org. Lett.,* 9:3523-3525, 2007.
Charest, et al., *J. Am. Chem. Soc.,* 127:8292-8293, 2005.
Charest, et al., *Science* 2005, 308, 395-398.
Chooi, et al., *Chem. Biol.,* 17:483-494, 2010.
Chooi, et al., *J. Am. Chem. Soc.,* 134:9428-9437, 2012.
Chooi, et al., *J. Am. Chem. Soc.,* 135:16805-16808, 2013.
Chopra and Roberts, *Microbiol. Mol. Biol. R.,* 65:232-260, 2001.
De Jesus, et al., *J. Chem. Soc., Chem. Comm.,* 902-904, 1982.
Duggar, *Ann. N. Y. Acad. Sci.,* 51:177-181, 1948.
Fulmer, et al., *Organometallics,* 29:2176-2179, 2010.
Horak, et al., *J. Chem. Soc., Chem. Comm.,* 1562-1564, 1988.
Hutchison, et al., *Toxicol. Appl. Pharmacol.,* 24:507-509, 1973.
Inokoshi, et al., *J. Antibiot.,* 66:37-41, 2013.
Kabuto, et al., *J. Chem. Soc., Chem. Comm.* 728-729, 1976.
Kodukula, et al., *J. Antibiot.,* 48:1055-1059, 1995.
Koyama, et al., *Molecules,* 18:204-224, 2013.
Kummer, et al., *Chem. Sci.,* 2:1710-1718, 2011.
*March's Advanced Organic Chemistry: Reactions, Mechanisms, and Structure,* 2007.
Nicolaou, et al., *Angew. Chem. Int. Ed.,* 52:8736-8741, 2013.
Nicolaou, et al., *J. Am. Chem. Soc.,* 136(34):12137-12160, 2014.
Pangborn, et al., *Organometallics,* 15:1518-1520, 1996.
Greene's Protective Groups in Organic Chemistry, Wuts and Greene, Ed., 1973
Remington's Pharmaceutical Sciences, 15$^{th}$ Ed., 1035-1038 and 1570-1580, 1990.
Remington's Pharmaceutical Sciences, 15$^{th}$ Ed., 3:624-652, 1990.
Shu, et al., *J. Antibiot.,* 48:1060-1065, 1995.
Silverton, et al., *Acta Crystallogr. B,* 38:3032-3037, 1982.
Still, et al., *J. Org. Chem.,* 43:2923-2925, 1978.
Stork, et al., *J. Am. Chem. Soc.,* 118:5304-5305, 1996.
Sun, et al., *J. Am. Chem. Soc.,* 130:17913-17927, 2008.
Sutcliffe, et al., *Antimicrob. Agents Chemother.,* 57:5548-5558, 2013.
Tally, et al., *J. Antimicrob. Chemother.,* 35:449-452, 1995.
NCI 60 cell line assay for Viridicatumtoxin A (NSC 159628).
Wong, et al., *J. Antibiot.* 46:214-221, 1993.
Wright and Myers, *Tetrahedron,* 67:9853-9869, 2011.
Wzorek, et al., *Org. Lett.,* 14:5840-5843, 2012.
Zheng, et al., *J. Antibiot.* 61:633-637, 2008.

What is claimed is:

1. A compound of the formula:

(I)

wherein:
- $X_1$ is absent such that atoms 16 and 17 are only connected by the shown single bond, a covalent bond such that a double bond is formed between atoms 16 and 17, —O—, alkanediyl$_{(C\leq 8)}$, or substituted alkanediyl$_{(C\leq 8)}$;
- $Y_1$, $Y_2$, and $Y_3$ are each independently alkyl$_{(C\leq 12)}$ or substituted alkyl$_{(C\leq 12)}$;
- $R_1$ is hydrogen, hydroxy, alkoxy$_{(C\leq 8)}$, substituted alkoxy$_{(C\leq 8)}$, or oxo, provided that when $R_1$ is oxo, the bond between $R_1$ and atom number 5 is a double bond;
- $R_2$ is hydrogen, amino, carboxy, cyano, halo, hydroxy, nitro, or sulfo;
- alkyl$_{(C\leq 12)}$, alkoxy$_{(C\leq 12)}$, alkylamino$_{(C\leq 12)}$, dialkylamino$_{(C\leq 18)}$, or a substituted version of any of these groups;
- $R_3$, $R_6$, $R_7$, and $R_{10}$ are each independently selected from: hydrogen,
- alkyl$_{(C\leq 8)}$, alkenyl$_{(C\leq 8)}$, aryl$_{(C\leq 12)}$, aralkyl$_{(C\leq 12)}$, acyl$_{(C\leq 8)}$, or a substituted version of any of these groups;
- $R_4$ and $R_5$ are each independently selected from: hydrogen,
- alkyl$_{(C\leq 8)}$, alkanediyl$_{(C\leq 8)}$-heterocycloalkyl$_{(C\leq 8)}$, alkanediyl$_{(C\leq 8)}$-heteroaryl$_{(C\leq 8)}$, alkanediyl$_{(C\leq 8)}$-alkylamino$_{(C\leq 8)}$, alkanediyl$_{(C\leq 8)}$-dialkylamino$_{(C\leq 8)}$, or a substituted version of any of these groups;
- $R_8$ is hydrogen,
- alkyl$_{(C\leq 8)}$, alkenyl$_{(C\leq 8)}$, aryl$_{(C\leq 12)}$, aralkyl$_{(C\leq 12)}$, acyl$_{(C\leq 8)}$, or a substituted version of any of these groups; or —$X_2$—$R_{11}$, wherein:
  - $X_2$ is alkanediyl$_{(C\leq 12)}$ or substituted alkanediyl$_{(C\leq 12)}$; and
  - $R_{11}$ is hydroxy, amino, azido, carboxy, or cyano,
  - alkenyl$_{(C\leq 6)}$, alkynyl$_{(C\leq 6)}$, heterocycloalkyl$_{(C\leq 12)}$, alkylamino$_{(C\leq 8)}$, dialkylamino$_{(C\leq 8)}$, alkoxy$_{(C\leq 8)}$, or a substituted version of any of these groups; or
  - a -linker-biomolecule wherein the biomolecule is a protein, a polypeptide, an amino acid, a cofactor, an imaging agent, an antibody, a fatty acid, a nucleic acid, or a small molecule therapeutic agent; and
- $R_9$ is hydrogen, amino, carboxy, cyano, halo, hydroxy, nitro, or sulfo;
- alkyl$_{(C\leq 12)}$, alkoxy$_{(C\leq 12)}$, alkylamino$_{(C\leq 12)}$, dialkylamino$_{(C\leq 18)}$, amido$_{(C\leq 12)}$, or a substituted version of any of these groups; or —NR$_{12}$C(O)R$_{13}$—NR$_{14}$R$_{15}$; wherein:
  - $R_{12}$ is hydrogen, alkyl$_{(C\leq 8)}$, or substituted alkyl$_{(C\leq 8)}$;
  - $R_{13}$ is alkanediyl$_{(C\leq 8)}$ or substituted alkanediyl$_{(C\leq 8)}$; and
  - $R_{14}$ and $R_{15}$ are each independently selected from: hydrogen,
    - alkyl$_{(C\leq 12)}$, aryl$_{(C\leq 12)}$, aralkyl$_{(C\leq 12)}$, acyl$_{(C\leq 12)}$, or a substituted version of any of these groups; or
    - $R_{14}$ and $R_{15}$ are taken together and are alkanediyl$_{(C\leq 8)}$, alkoxydiyl$_{(C\leq 8)}$, alkylaminodiyl$_{(C\leq 8)}$, or a substituted version of any of these groups;

or a pharmaceutically acceptable salt or tautomer thereof.

2. The compound of claim 1 further defined as:

(II)

wherein:
- $X_1$ is absent such that atoms 16 and 17 are only connected by the shown single bond, a covalent bond such that a double bond is formed between atoms 16 and 17, —O—, alkanediyl$_{(C\leq 8)}$, or substituted alkanediyl$_{(C\leq 8)}$;
- $Y_1$, $Y_2$, and $Y_3$ are each independently alkyl$_{(C\leq 12)}$ or substituted alkyl$_{(C\leq 12)}$;
- $R_1$ is hydrogen, hydroxy, alkoxy$_{(C\leq 8)}$, substituted alkoxy$_{(C\leq 8)}$, or oxo, provided that when $R_1$ is oxo, the bond between $R_1$ and atom number 5 is a double bond;
- $R_2$ is hydrogen, amino, carboxy, cyano, halo, hydroxy, nitro, or sulfo;
- alkyl$_{(C\leq 12)}$, alkoxy$_{(C\leq 12)}$, alkylamino$_{(C\leq 12)}$, dialkylamino$_{(C\leq 8)}$, or a substituted version of any of these groups;
- $R_4$ and $R_5$ are each independently selected from: hydrogen,
- alkyl$_{(C\leq 8)}$, alkanediyl$_{(C\leq 8)}$-heterocycloalkyl$_{(C\leq 8)}$, alkanediyl$_{(C\leq 8)}$-heteroaryl$_{(C\leq 8)}$, alkanediyl$_{(C\leq 8)}$-alkylamino$_{(C\leq 8)}$, alkanediyl$_{(C\leq 8)}$-dialkylamino$_{(C\leq 8)}$, or a substituted version of any of these groups;
- $R_8$ is hydrogen,
- alkyl$_{(C\leq 8)}$, alkenyl$_{(C\leq 12)}$, aryl$_{(C\leq 12)}$, aralkyl$_{(C\leq 12)}$, acyl$_{(C\leq 8)}$, or a substituted version of any of these groups; or —$X_2$—$R_{11}$, wherein:
  - $X_2$ is alkanediyl$_{(C\leq 12)}$ or substituted alkanediyl$_{(C\leq 12)}$; and
  - $R_{11}$ is hydroxy, amino, azido, carboxy, or cyano,
  - alkenyl$_{(C\leq 6)}$, alkynyl$_{(C\leq 6)}$, heterocycloalkyl$_{(C\leq 12)}$, alkylamino$_{(C\leq 8)}$, dialkylamino$_{(C\leq 8)}$, alkoxy$_{(C\leq 8)}$, or a substituted version of any of these groups; or
  - a -linker-biomolecule wherein the biomolecule is a protein, a polypeptide, an amino acid, a cofactor, an imaging agent, an antibody, a fatty acid, a nucleic acid, or a small molecule therapeutic agent; and $R_9$ is hydrogen, amino, carboxy, cyano, halo, hydroxy, nitro, or sulfo;

alkyl$_{(C \leq 12)}$, alkoxy$_{(C \leq 12)}$, alkylamino$_{(C \leq 12)}$, dialkylamino$_{(C \leq 18)}$, amido$_{(C \leq 12)}$, or a substituted version of any of these groups; or —NR$_{12}$C(O)R$_{13}$—NR$_{14}$R$_{15}$; wherein:

$R_{12}$ is hydrogen, alkyl$_{(C \leq 8)}$, or substituted alkyl$_{(C \leq 8)}$;

$R_{13}$ is alkanediyl$_{(C \leq 8)}$ or substituted alkanediyl$_{(C \leq 8)}$; and $R_{14}$ and $R_{15}$ are each independently selected from: hydrogen, alkyl$_{(C \leq 12)}$, aryl$_{(C \leq 12)}$, aralkyl$_{(C \leq 12)}$, acyl$_{(C \leq 12)}$, or a substituted version of any of these groups; or $R_{14}$ and $R_{15}$ are taken together and are alkanediyl$_{(C \leq 8)}$, alkoxydiyl$_{(C \leq 8)}$, alkylaminodiyl$_{(C \leq 8)}$, or a substituted version of any of these groups;

or a pharmaceutically acceptable salt or tautomer thereof.

3. The compound of claim 1 further defined as:

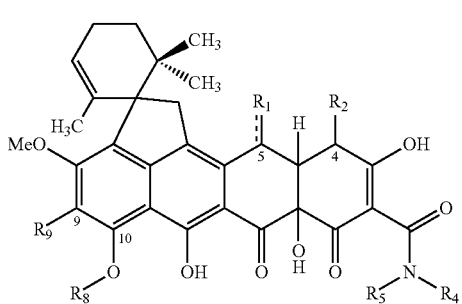

(IV)

wherein:

$R_1$ is hydrogen, hydroxy, alkoxy$_{(C \leq 8)}$, substituted alkoxy$_{(C \leq 8)}$, or oxo, provided that when $R_1$ is oxo, the bond between $R_1$ and atom number 5 is a double bond and when the bond between $R_1$ and atom number 5 is a double bond then $R_1$ is oxo;

$R_2$ is hydrogen, amino, carboxy, cyano, halo, hydroxy, nitro, or sulfo;

alkyl$_{(C \leq 12)}$, alkoxy$_{(C \leq 12)}$, alkylamino$_{(C \leq 12)}$, dialkylamino$_{(C \leq 18)}$, or a substituted version of any of these groups;

$R_4$ and $R_5$ are each independently selected from: hydrogen, alkyl$_{(C \leq 8)}$, alkanediyl$_{(C \leq 8)}$-heterocycloalkyl$_{(C \leq 8)}$, alkanediyl$_{(C \leq 8)}$-heteroaryl$_{(C \leq 8)}$, alkanediyl$_{(C \leq 8)}$-alkylamino$_{(C \leq 8)}$, alkanediyl$_{(C \leq 8)}$-dialkylamino$_{(C \leq 8)}$, or a substituted version of any of these groups;

$R_8$ is hydrogen, alkyl$_{(C \leq 8)}$, alkenyl$_{(C \leq 8)}$, aryl$_{(C \leq 12)}$, aralkyl$_{(C \leq 12)}$, acyl$_{(C \leq 8)}$, or a substituted version of any of these groups; or —X$_2$—R$_{11}$, wherein:

$X_2$ is alkanediyl$_{(C \leq 12)}$ or substituted alkanediyl$_{(C \leq 12)}$; and $R_{11}$ is hydroxy, amino, azido, carboxy, or cyano, alkenyl$_{(C \leq 6)}$, alkynyl$_{(C \leq 6)}$, heterocycloalkyl$_{(C \leq 12)}$, alkylamino$_{(C \leq 8)}$, dialkylamino$_{(C \leq 8)}$, alkoxy$_{(C \leq 8)}$, or a substituted version of any of these groups; or a -linker-biomolecule wherein the biomolecule is a protein, a polypeptide, an amino acid, a cofactor, an imaging agent, an antibody, a fatty acid, a nucleic acid, or a small molecule therapeutic agent; and $R_9$ is hydrogen, amino, carboxy, cyano, halo, hydroxy, nitro, or sulfo;

alkyl$_{(C \leq 12)}$, alkoxy$_{(C \leq 12)}$, alkylamino$_{(C \leq 12)}$, dialkylamino$_{(C \leq 18)}$, amido$_{(C \leq 12)}$, or a substituted version of any of these groups; or —NR$_{12}$C(O)R$_{13}$—NR$_{14}$R$_{15}$; wherein:

$R_{12}$ is hydrogen, alkyl$_{(C \leq 8)}$, or substituted alkyl$_{(C \leq 8)}$;

$R_{13}$ is alkanediyl$_{(C \leq 8)}$ or substituted alkanediyl$_{(C \leq 8)}$; and $R_{14}$ and $R_{15}$ are each independently selected from: hydrogen, alkyl$_{(C \leq 12)}$, aryl$_{(C \leq 12)}$, aralkyl$_{(C \leq 12)}$, acyl$_{(C \leq 12)}$, or a substituted version of any of these groups; or $R_{14}$ and $R_{15}$ are taken together and are alkanediyl$_{(C \leq 8)}$, alkoxydiyl$_{(C \leq 8)}$, alkylaminodiyl$_{(C \leq 8)}$, or a substituted version of any of these groups;

or a pharmaceutically acceptable salt or tautomer thereof.

4. The compound of claim 1 further defined as:

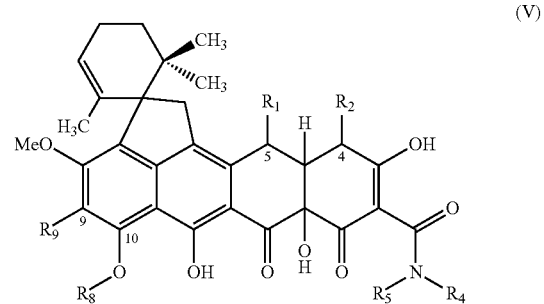

(V)

wherein:

$R_1$ is hydroxy, alkoxy$_{(C \leq 8)}$, or substituted alkoxy$_{(C \leq 8)}$;

$R_2$ is hydrogen, amino, carboxy, cyano, halo, hydroxy, nitro, or sulfo;

alkyl$_{(C \leq 12)}$, alkoxy$_{(C \leq 12)}$, alkylamino$_{(C \leq 12)}$, dialkylamino$_{(C \leq 18)}$, or a substituted version of any of these groups;

$R_4$ is hydrogen, alkyl$_{(C \leq 8)}$, alkanediyl$_{(C \leq 8)}$-heterocycloalkyl$_{(C \leq 8)}$, alkanediyl$_{(C \leq 8)}$-heteroaryl$_{(C \leq 8)}$, alkanediyl$_{(C \leq 8)}$-alkylamino$_{(C \leq 8)}$, alkanediyl$_{(C \leq 8)}$-dialkylamino$_{(C \leq 8)}$, or a substituted version of any of these groups;

$R_8$ is hydrogen, alkyl$_{(C \leq 8)}$, alkenyl$_{(C \leq 8)}$, aryl$_{(C \leq 12)}$, aralkyl$_{(C \leq 12)}$, acyl$_{(C \leq 8)}$, or a substituted version of any of these groups; or —X$_2$—R$_{11}$, wherein:

$X_2$ is alkanediyl$_{(C \leq 12)}$ or substituted alkanediyl$_{(C \leq 12)}$; and $R_{11}$ is hydroxy, amino, azido, carboxy, or cyano, alkenyl$_{(C \leq 6)}$, alkynyl$_{(C \leq 6)}$, heterocycloalkyl$_{(C \leq 12)}$, alkylamino$_{(C \leq 8)}$, dialkylamino$_{(C \leq 8)}$, alkoxy$_{(C \leq 8)}$, or a substituted version of any of these groups; or a -linker-biomolecule wherein the biomolecule is a protein, a polypeptide, an amino acid, a cofactor, an imaging agent, an antibody, a fatty acid, a nucleic acid, or a small molecule therapeutic agent; and $R_9$ is hydrogen, amino, carboxy, cyano, halo, hydroxy, nitro, or sulfo;
alkyl$_{(C≤12)}$, alkoxy$_{(C≤12)}$, alkylamino$_{(C≤12)}$, dialkylamino$_{(C≤18)}$, amido$_{(C≤12)}$, or a substituted version of any of these groups; or —NR$_{12}$C(O)R$_{13}$—NR$_{14}$R$_{15}$;
wherein:
- $R_{12}$ is hydrogen, alkyl$_{(C≤8)}$, or substituted alkyl$_{(C≤8)}$;
- $R_{13}$ is alkanediyl$_{(C≤8)}$ or substituted alkanediyl$_{(C≤8)}$; and
- $R_{14}$ and $R_{15}$ are each independently selected from: hydrogen, alkyl$_{(C≤12)}$, aryl$_{(C≤12)}$, aralkyl$_{(C≤12)}$, acyl$_{(C≤12)}$, or a substituted version of any of these groups; or
- $R_{14}$ and $R_{15}$ are taken together and are alkanediyl$_{(C≤8)}$, alkoxydiyl$_{(C≤8)}$, alkylaminodiyl$_{(C≤8)}$, or a substituted version of any of these groups;

or a pharmaceutically acceptable salt or tautomer thereof.

5. The compound of claim 1 further defined as:

(V)

wherein:
- $R_1$ is hydroxy, alkoxy$_{(C≤8)}$, or substituted alkoxy$_{(C≤8)}$;
- $R_2$ is hydrogen, amino, carboxy, cyano, halo, hydroxy, nitro, or sulfo;
  alkyl$_{(C≤12)}$, alkoxy$_{(C≤12)}$, alkylamino$_{(C≤12)}$, dialkylamino$_{(C≤18)}$, or a substituted version of any of these groups;
- $R_4$ is hydrogen, alkyl$_{(C≤8)}$, or a substituted alkyl$_{(C≤8)}$,
- $R_5$ is hydrogen,
  alkyl$_{(C≤8)}$, alkanediyl$_{(C≤8)}$-heterocycloalkyl$_{(C≤8)}$, alkanediyl$_{(C≤8)}$-heteroaryl$_{(C≤8)}$, alkanediyl$_{(C≤8)}$-alkylamino$_{(C≤8)}$, alkanediyl$_{(C≤8)}$-dialkylamino$_{(C≤8)}$, or a substituted version of any of these groups;
- $R_8$ is hydrogen,
  alkyl$_{(C≤8)}$, alkenyl$_{(C≤8)}$, aryl$_{(C≤12)}$, aralkyl$_{(C≤12)}$, acyl$_{(C≤8)}$, or a substituted version of any of these groups; or —X$_2$—R$_{11}$, wherein:
  - X$_2$ is alkanediyl$_{(C≤12)}$ or substituted alkanediyl$_{(C≤12)}$; and
  - R$_{11}$ is hydroxy, amino, azido, carboxy, or cyano, alkenyl$_{(C≤6)}$, alkynyl$_{(C≤6)}$, heterocycloalkyl$_{(C≤12)}$, alkylamino$_{(C≤8)}$, dialkylamino$_{(C≤8)}$, alkoxy$_{(C≤8)}$, or a substituted version of any of these groups; or
  - a -linker-biomolecule
  wherein:
    - the linker is alkanediyl$_{(C≤12)}$, alkenediyl$_{(C≤12)}$, arenediyl$_{(C≤12)}$, heteroarenediyl$_{(C≤12)}$, heterocycloalkanediyl$_{(C≤12)}$ or a substituted version of any of these groups; and
    - the biomolecule is a protein, a polypeptide, an antibody, an imaging agent, or a small molecule therapeutic agent;
- $R_9$ is hydrogen, amino, carboxy, cyano, halo, hydroxy, nitro, or sulfo;
  alkyl$_{(C≤12)}$, alkoxy$_{(C≤12)}$, alkylamino$_{(C≤12)}$, dialkylamino$_{(C≤18)}$, amido$_{(C≤12)}$, or a substituted version of any of these groups; or —NR$_{12}$C(O)R$_{13}$—NR$_{14}$R$_{15}$;
  wherein:
  - $R_{12}$ is hydrogen, alkyl$_{(C≤8)}$, or substituted alkyl$_{(C≤8)}$;
  - $R_{13}$ is alkanediyl$_{(C≤8)}$ or substituted alkanediyl$_{(C≤8)}$; and
  - $R_{14}$ and $R_{15}$ are each independently selected from: hydrogen, alkyl$_{(C≤12)}$, aryl$_{(C≤12)}$, aralkyl$_{(C≤12)}$, acyl$_{(C≤12)}$, or a substituted version of any of these groups; or
  - $R_{14}$ and $R_{15}$ are taken together and are alkanediyl$_{(C≤8)}$, alkoxydiyl$_{(C≤8)}$, alkylaminodiyl$_{(C≤8)}$, or a substituted version of any of these groups;

or a pharmaceutically acceptable salt or tautomer thereof.

6. The compound of claim 1 further defined as:

(V)

wherein:
- $R_1$ is hydroxy, alkoxy$_{(C≤8)}$, or substituted alkoxy$_{(C≤8)}$;
- $R_2$ is hydrogen, amino, carboxy, cyano, halo, hydroxy, nitro, or sulfo;
  alkyl$_{(C≤12)}$, alkoxy$_{(C≤12)}$, alkylamino$_{(C≤12)}$, dialkylamino$_{(C≤18)}$, or a substituted version of any of these groups;
- $R_4$ is hydrogen, alkyl$_{(C≤8)}$, or a substituted alkyl$_{(C≤8)}$,
- $R_5$ is hydrogen,
  alkyl$_{(C≤8)}$, alkanediyl$_{(C≤8)}$-heterocycloalkyl$_{(C≤8)}$, alkanediyl$_{(C≤8)}$-heteroaryl$_{(C≤8)}$, alkanediyl$_{(C≤8)}$-alkylamino$_{(C≤8)}$, alkanediyl$_{(C≤8)}$-dialkylamino$_{(C≤8)}$, or a substituted version of any of these groups;
- $R_8$ is hydrogen or -linker-biomolecule;
  wherein:
    - the linker is alkanediyl$_{(C≤12)}$, alkenediyl$_{(C≤12)}$, arenediyl$_{(C≤12)}$, heteroarenediyl$_{(C≤12)}$, heterocycloalkanediyl$_{(C≤12)}$; and
    - the biomolecule is an antibody; and
- $R_9$ is hydrogen, amino, carboxy, cyano, halo, hydroxy, nitro, or sulfo;
  alkyl$_{(C≤12)}$, alkoxy$_{(C≤12)}$, alkylamino$_{(C≤12)}$, dialkylamino$_{(C≤18)}$, amido$_{(C≤12)}$, or a substituted version of any of these groups; or —NR$_{12}$C(O)R$_{13}$—NR$_{14}$R$_{15}$;
  wherein:
  - $R_{12}$ is hydrogen, alkyl$_{(C≤8)}$, or substituted alkyl$_{(C≤8)}$;

$R_{13}$ is alkanediyl$_{(C\leq 8)}$ or substituted alkanediyl$_{(C\leq 8)}$; and $R_{14}$ and $R_{15}$ are each independently selected from: hydrogen, alkyl$_{(C\leq 12)}$, aryl$_{(C\leq 12)}$, aralkyl$_{(C\leq 12)}$, acyl$_{(C\leq 12)}$, or a substituted version of any of these groups; or $R_{14}$ and $R_{15}$ are taken together and are alkanediyl$_{(C\leq 8)}$, alkoxydiyl$_{(C\leq 8)}$, alkylaminodiyl$_{(C\leq 8)}$, or a substituted version of any of these groups;

or a pharmaceutically acceptable salt or tautomer thereof.

7. The compound of claim 1 further defined as:

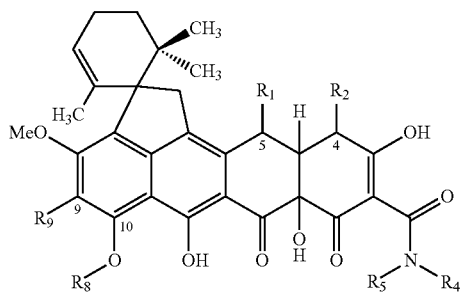

(V)

wherein:

$R_1$ is hydroxy, alkoxy$_{(C\leq 8)}$, or substituted alkoxy$_{(C\leq 8)}$;

$R_2$ is hydrogen, amino, halo, or hydroxy;

alkylamino$_{(C\leq 12)}$, dialkylamino$_{(C\leq 18)}$, or a substituted version of any of these groups;

$R_4$ is hydrogen, alkyl$_{(C\leq 8)}$, or a substituted alkyl$_{(C\leq 8)}$, $R_5$ is hydrogen, alkyl$_{(C\leq 8)}$, alkanediyl$_{(C\leq 8)}$-heterocycloalkyl$_{(C\leq 8)}$, alkanediyl$_{(C\leq 8)}$-heteroaryl$_{(C\leq 8)}$, alkanediyl$_{(C\leq 8)}$-alkylamino$_{(C\leq 8)}$, alkanediyl$_{(C\leq 8)}$-dialkylamino$_{(C\leq 8)}$, or a substituted version of any of these groups;

$R_8$ is hydrogen, alkyl$_{(C\leq 8)}$, alkenyl$_{(C\leq 8)}$, aryl$_{(C\leq 12)}$, aralkyl$_{(C\leq 12)}$, acyl$_{(C\leq 8)}$, or a substituted version of any of these groups; or —X$_2$—R$_{11}$, wherein:

X$_2$ is alkanediyl$_{(C\leq 12)}$ or substituted alkanediyl$_{(C\leq 12)}$; and $R_{11}$ is hydroxy, amino, azido, carboxy, or cyano, alkenyl$_{(C\leq 6)}$, alkynyl$_{(C\leq 6)}$, heterocycloalkyl$_{(C\leq 12)}$, alkylamino$_{(C\leq 8)}$, dialkylamino$_{(C\leq 8)}$, alkoxy$_{(C\leq 8)}$, or a substituted version of any of these groups; or a -linker-biomolecule; and $R_9$ is hydrogen, amino, carboxy, cyano, halo, hydroxy; alkoxy$_{(C\leq 12)}$, amido$_{(C\leq 12)}$, or a substituted version of any of these groups; or —NR$_{12}$C(O)R$_{13}$—NR$_{14}$R$_{15}$; wherein:

$R_{12}$ is hydrogen, alkyl$_{(C\leq 8)}$, or substituted alkyl$_{(C\leq 8)}$;

$R_{13}$ is alkanediyl$_{(C\leq 8)}$ or substituted alkanediyl$_{(C\leq 8)}$; and $R_{14}$ and $R_{15}$ are each independently selected from: hydrogen, alkyl$_{(C\leq 12)}$, aryl$_{(C\leq 12)}$, aralkyl$_{(C\leq 12)}$, acyl$_{(C\leq 12)}$, or a substituted version of any of these groups; or $R_{14}$ and $R_{15}$ are taken together and are alkanediyl$_{(C\leq 8)}$, alkoxydiyl$_{(C\leq 8)}$, alkylaminodiyl$_{(C\leq 8)}$, or a substituted version of any of these groups;

or a pharmaceutically acceptable salt or tautomer thereof.

8. The compound of claim 1 further defined as:

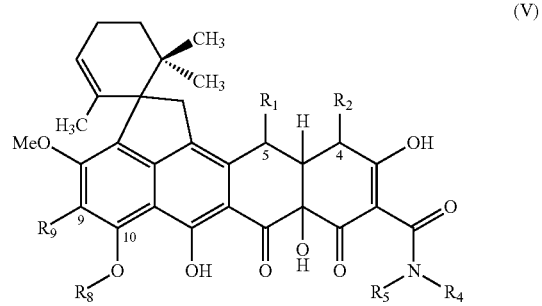

(V)

wherein:

$R_1$ is hydroxy, alkoxy$_{(C\leq 8)}$, or substituted alkoxy$_{(C\leq 8)}$;

$R_2$ is hydrogen, amino, halo, or hydroxy;

alkylamino$_{(C\leq 12)}$, dialkylamino$_{(C\leq 18)}$, or a substituted version of any of these groups;

$R_4$ is hydrogen, alkyl$_{(C\leq 8)}$, or a substituted alkyl$_{(C\leq 8)}$, $R_5$ is hydrogen, alkyl$_{(C\leq 8)}$, alkanediyl$_{(C\leq 8)}$-heterocycloalkyl$_{(C\leq 8)}$, alkanediyl$_{(C\leq 8)}$-heteroaryl$_{(C\leq 8)}$, alkanediyl$_{(C\leq 8)}$-alkylamino$_{(C\leq 8)}$, alkanediyl$_{(C\leq 8)}$-dialkylamino$_{(C\leq 8)}$, or a substituted version of any of these groups;

$R_8$ is hydrogen, alkyl$_{(C\leq 8)}$, alkenyl$_{(C\leq 8)}$, aryl$_{(C\leq 12)}$, aralkyl$_{(C\leq 12)}$, acyl$_{(C\leq 8)}$, or a substituted version of any of these groups; or —X$_2$—R$_{11}$, wherein:

X$_2$ is alkanediyl$_{(C\leq 12)}$ or substituted alkanediyl$_{(C\leq 12)}$; and $R_{11}$ is hydroxy, amino, azido, carboxy, or cyano, alkenyl$_{(C\leq 6)}$, alkynyl$_{(C\leq 6)}$, heterocycloalkyl$_{(C\leq 12)}$, alkylamino$_{(C\leq 8)}$, dialkylamino$_{(C\leq 8)}$, alkoxy$_{(C\leq 8)}$, or a substituted version of any of these groups; or a -linker-biomolecule; and $R_9$ is —NR$_{12}$C(O)R$_{13}$—NR$_{14}$R$_{15}$;

wherein:

$R_{12}$ is hydrogen, alkyl$_{(C\leq 8)}$, or substituted alkyl$_{(C\leq 8)}$;

$R_{13}$ is alkanediyl$_{(C\leq 8)}$ or substituted alkanediyl$_{(C\leq 8)}$; and $R_{14}$ and $R_{15}$ are each independently selected from: hydrogen, alkyl$_{(C\leq 12)}$, aryl$_{(C\leq 12)}$, aralkyl$_{(C\leq 12)}$, acyl$_{(C\leq 12)}$, or a substituted version of any of these groups;

or a pharmaceutically acceptable salt or tautomer thereof.

9. The compound of claim 1, wherein $R_1$ is alkoxy$_{(C\leq 8)}$ or substituted alkoxy$_{(C\leq 8)}$.

10. The compound of claim 9, wherein $R_1$ is methoxy.

11. The compound of claim 1, wherein $R_1$ is oxo.

12. The compound of claim 1, wherein $R_2$ is hydrogen.

13. The compound of claim 1, wherein $R_2$ is amino.

14. The compound of claim 1, wherein $R_8$ is hydrogen.

15. The compound of claim 1, wherein the compound is further defined as:

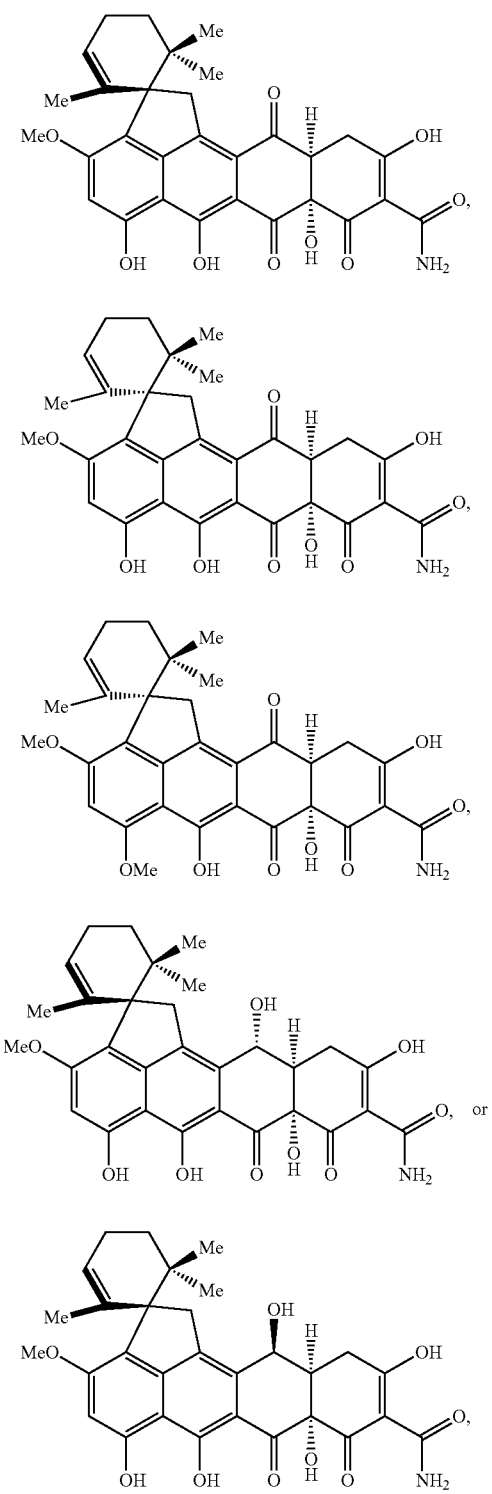

or a pharmaceutically acceptable salt, or tautomer thereof.

16. A pharmaceutical composition comprising a compound of claim 1 and an excipient.

17. A method of treating a bacterial infection comprising administering a pharmaceutically effective amount of a compound or composition of claim 1.

18. A method of preparing a compound of the formula:

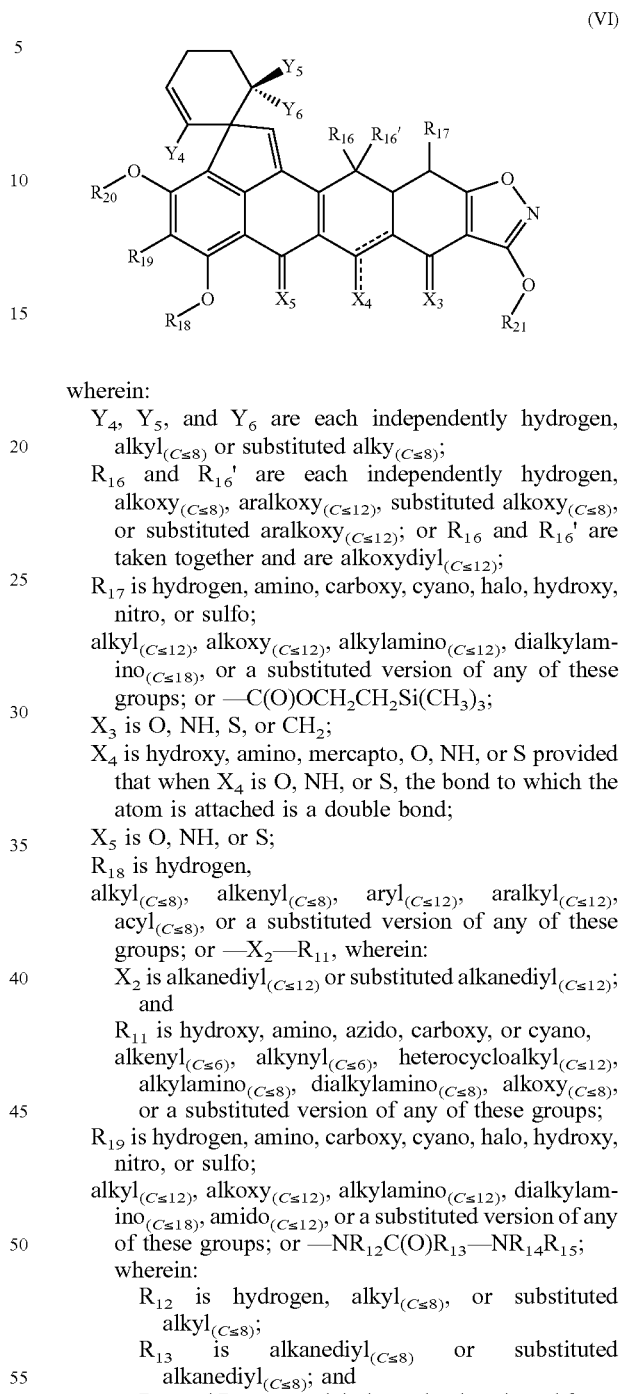

(VI)

wherein:
$Y_4$, $Y_5$, and $Y_6$ are each independently hydrogen, $alkyl_{(C\le8)}$ or substituted $alky_{(C\le8)}$;
$R_{16}$ and $R_{16}'$ are each independently hydrogen, $alkoxy_{(C\le8)}$, $aralkoxy_{(C\le12)}$, substituted $alkoxy_{(C\le8)}$, or substituted $aralkoxy_{(C\le12)}$; or $R_{16}$ and $R_{16}'$ are taken together and are $alkoxydiyl_{(C\le12)}$;
$R_{17}$ is hydrogen, amino, carboxy, cyano, halo, hydroxy, nitro, or sulfo;
$alkyl_{(C\le12)}$, $alkoxy_{(C\le12)}$, $alkylamino_{(C\le12)}$, $dialkylamino_{(C\le18)}$, or a substituted version of any of these groups; or —C(O)OCH$_2$CH$_2$Si(CH$_3$)$_3$;
$X_3$ is O, NH, S, or CH$_2$;
$X_4$ is hydroxy, amino, mercapto, O, NH, or S provided that when $X_4$ is O, NH, or S, the bond to which the atom is attached is a double bond;
$X_5$ is O, NH, or S;
$R_{18}$ is hydrogen,
$alkyl_{(C\le8)}$, $alkenyl_{(C\le8)}$, $aryl_{(C\le12)}$, $aralkyl_{(C\le12)}$, $acyl_{(C\le8)}$, or a substituted version of any of these groups; or —X$_2$—R$_{11}$, wherein:
$X_2$ is $alkanediyl_{(C\le12)}$ or substituted $alkanediyl_{(C\le12)}$; and
$R_{11}$ is hydroxy, amino, azido, carboxy, or cyano, $alkenyl_{(C\le6)}$, $alkynyl_{(C\le6)}$, $heterocycloalkyl_{(C\le12)}$, $alkylamino_{(C\le8)}$, $dialkylamino_{(C\le8)}$, $alkoxy_{(C\le8)}$, or a substituted version of any of these groups;
$R_{19}$ is hydrogen, amino, carboxy, cyano, halo, hydroxy, nitro, or sulfo;
$alkyl_{(C\le12)}$, $alkoxy_{(C\le12)}$, $alkylamino_{(C\le12)}$, $dialkylamino_{(C\le18)}$, $amido_{(C\le12)}$, or a substituted version of any of these groups; or —NR$_{12}$C(O)R$_{13}$—NR$_{14}$R$_{15}$;
wherein:
$R_{12}$ is hydrogen, $alkyl_{(C\le8)}$, or substituted $alkyl_{(C\le8)}$;
$R_{13}$ is $alkanediyl_{(C\le8)}$ or substituted $alkanediyl_{(C\le8)}$; and
$R_{14}$ and $R_{15}$ are each independently selected from: hydrogen,
$alkyl_{(C\le12)}$, $aryl_{(C\le12)}$, $aralkyl_{(C\le12)}$, $acyl_{(C\le12)}$, or a substituted version of any of these groups; or
$R_{14}$ and $R_{15}$ taken together and are $alkanediyl_{(C\le8)}$, $alkoxydiyl_{(C\le8)}$, $alkylaminodiyl_{(C\le8)}$, or a substituted version of any of these groups; and
$R_{20}$ and $R_{21}$ are each independently hydrogen, $alkyl_{(C\le8)}$, $alkenyl_{(C\le8)}$, $aryl_{(C\le12)}$, $aralkyl_{(C\le12)}$, $acyl_{(C\le8)}$, or a substituted version of any of these groups;

or a salt, tautomer, or optical isomer thereof; comprising reacting a compound of the formula:

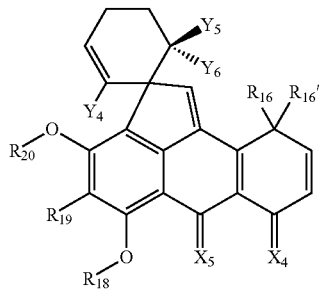
(VII)

wherein:
Y$_4$, Y$_5$, Y$_6$, R$_{16}$, R$_{16}'$, X$_5$, R$_{18}$, R$_{19}$, and R$_{20}$ are as defined above; and
X$_4$ is O, NH, or S;
with a compound of the formula:

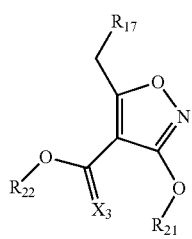
(VIII)

wherein:
X$_3$ and R$_{17}$ are as defined above;
R$_{21}$ is hydrogen,
alkyl$_{(C≤8)}$, alkenyl$_{(C≤8)}$, aryl$_{(C≤12)}$, aralkyl$_{(C≤12)}$, acyl$_{(C≤8)}$, or a substituted version of any of these groups; and
R$_{22}$ is aryl$_{(C≤12)}$, aralkyl$_{(C≤12)}$, or a substituted version of either of these groups;
in the presence of a base.

19. The method of claim 18, wherein the method further comprises forming a compound of the formula:

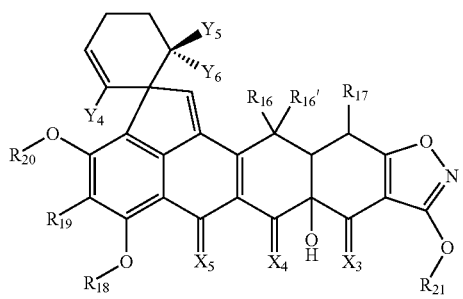
(IX)

wherein:
Y$_4$, Y$_5$, and Y$_6$ are each independently hydrogen, alkyl$_{(C≤8)}$ or substituted alky$_{(C≤8)}$;
R$_{16}$ and R$_{16}'$ are each independently hydrogen, alkoxy$_{(C≤8)}$, aralkoxy$_{(C≤12)}$, substituted alkoxy$_{(C≤8)}$, or substituted aralkoxy$_{(C≤12)}$; or R$_{16}$ and R$_{16}'$ are taken together and are alkoxydiyl$_{(C≤12)}$;
R$_{17}$ is hydrogen, amino, carboxy, cyano, halo, hydroxy, nitro, or sulfo;
alkyl$_{(C≤12)}$, alkoxy$_{(C≤12)}$, alkylamino$_{(C≤12)}$, dialkylamino$_{(C≤18)}$, or a substituted version of any of these groups; or —C(O)OCH$_2$CH$_2$Si(CH$_3$)$_3$;
X$_3$ is O, NH, S, or CH$_2$;
X$_4$ is O, NH, or S;
X$_5$ is O, NH, or S;
R$_{18}$ is hydrogen,
alkyl$_{(C≤8)}$, alkenyl$_{(C≤8)}$, aryl$_{(C≤12)}$, aralkyl$_{(C≤12)}$, acyl$_{(C≤8)}$, or a substituted version of any of these groups; or —X$_2$—R$_{11}$, wherein:
X$_2$ is alkanediyl$_{(C≤12)}$ or substituted alkanediyl$_{(C≤12)}$; and
R$_{11}$ is hydroxy, amino, azido, carboxy, or cyano,
alkenyl$_{(C≤6)}$, alkynyl$_{(C≤6)}$, heterocycloalkyl$_{(C≤12)}$, alkylamino$_{(C≤8)}$, dialkylamino$_{(C≤8)}$, alkoxy$_{(C≤8)}$, or a substituted version of any of these groups;
R$_{19}$ is hydrogen, amino, carboxy, cyano, halo, hydroxy, nitro, or sulfo;
alkyl$_{(C≤12)}$, alkoxy$_{(C≤12)}$, alkylamino$_{(C≤12)}$, dialkylamino$_{(C≤18)}$, amido$_{(C≤12)}$, or a substituted version of any of these groups; or —NR$_{12}$C(O)R$_{13}$—NR$_{14}$R$_{15}$;
wherein:
R$_{12}$ is hydrogen, alkyl$_{(C≤8)}$, or substituted alkyl$_{(C≤8)}$;
R$_{13}$ is alkanediyl$_{(C≤8)}$ or substituted alkanediyl$_{(C≤8)}$; and
R$_{14}$ and R$_{15}$ are each independently selected from:
hydrogen,
alkyl$_{(C≤12)}$, aryl$_{(C≤12)}$, aralkyl$_{(C≤12)}$, acyl$_{(C≤12)}$, or a substituted version of any of these groups; or
R$_{14}$ and R$_{15}$ taken together and are alkanediyl$_{(C≤8)}$, alkoxydiyl$_{(C≤8)}$, alkylaminodiyl$_{(C≤8)}$, or a substituted version of any of these groups; and
R$_{20}$ and R$_{21}$ are each independently hydrogen,
alkyl$_{(C≤8)}$, alkenyl$_{(C≤8)}$, aryl$_{(C≤12)}$, aralkyl$_{(C≤12)}$, acyl$_{(C≤8)}$, or a substituted version of any of these groups;
or a salt, tautomer, or optical isomer thereof; comprising reacting a compound of the formula:

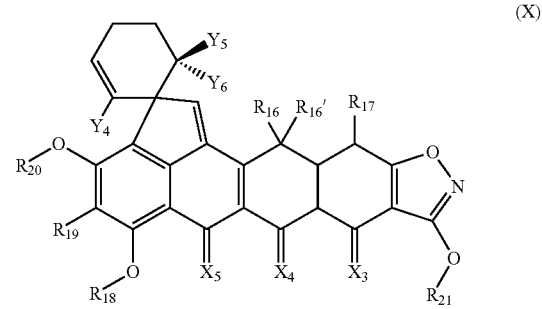
(X)

wherein the variables are as defined above; with a metal catalyst and an oxidizing agent.

20. The method of claim 19, wherein the reaction further comprises reacting a compound of formula IX with a reducing agent to form a compound of the formula:

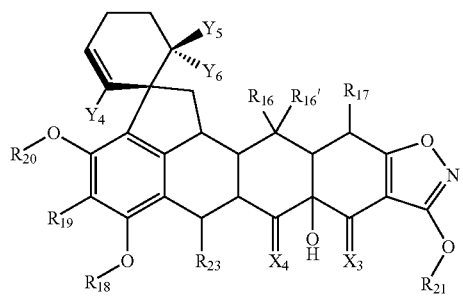

(XI)

wherein:
- $Y_4$, $Y_5$, and $Y_6$ are each independently hydrogen, alkyl$_{(C\leq 8)}$ or substituted alky$_{(C\leq 8)}$;
- $R_{16}$ and $R_{16}'$ are each independently hydrogen, alkoxy$_{(C\leq 8)}$, aralkoxy$_{(C\leq 12)}$, substituted alkoxy$_{(C\leq 8)}$, or substituted aralkoxy$_{(C\leq 12)}$; or $R_{16}$ and $R_{16}'$ are taken together and are alkoxydiyl$_{(C\leq 12)}$;
- $R_{17}$ is hydrogen, amino, carboxy, cyano, halo, hydroxy, nitro, or sulfo;
  alkyl$_{(C\leq 12)}$, alkoxy$_{(C\leq 12)}$, alkylamino$_{(C\leq 12)}$, dialkylamino$_{(C\leq 18)}$, or a substituted version of any of these groups; or —C(O)OCH$_2$CH$_2$Si(CH$_3$)$_3$;
- $X_3$ is O, NH, S, or CH$_2$;
- $X_4$ is O, NH, or S;
- $R_{18}$ is hydrogen,
  alkyl$_{(C\leq 8)}$, alkenyl$_{(C\leq 8)}$, aryl$_{(C\leq 12)}$, aralkyl$_{(C\leq 12)}$, acyl$_{(C\leq 8)}$, or a substituted version of any of these groups; or —X$_2$—R$_{11}$, wherein:
  - $X_2$ is alkanediyl$_{(C\leq 12)}$ or substituted alkanediyl$_{(C\leq 12)}$; and
  - $R_{11}$ is hydroxy, amino, azido, carboxy, or cyano, alkenyl$_{(C\leq 6)}$, alkynyl$_{(C\leq 6)}$, heterocycloalkyl$_{(C\leq 12)}$, alkylamino$_{(C\leq 8)}$, dialkylamino$_{(C\leq 8)}$, alkoxy$_{(C\leq 8)}$, or a substituted version of any of these groups;
- $R_{19}$ is hydrogen, amino, carboxy, cyano, halo, hydroxy, nitro, or sulfo;
  alkyl$_{(C\leq 12)}$, alkoxy$_{(C\leq 12)}$, alkylamino$_{(C\leq 12)}$, dialkylamino$_{(C\leq 18)}$, amido$_{(C\leq 12)}$, or a substituted version of any of these groups; or —NR$_{12}$C(O)R$_{13}$—NR$_{14}$R$_{15}$; wherein:
  - $R_{12}$ is hydrogen, alkyl$_{(C\leq 8)}$, or substituted alkyl$_{(C\leq 8)}$;
  - $R_{13}$ is alkanediyl$_{(C\leq 8)}$ or substituted alkanediyl$_{(C\leq 8)}$; and
  - $R_{14}$ and $R_{15}$ are each independently selected from: hydrogen,
    alkyl$_{(C\leq 12)}$, aryl$_{(C\leq 12)}$, aralkyl$_{(C\leq 12)}$, acyl$_{(C\leq 12)}$, or a substituted version of any of these groups; or
    $R_{14}$ and $R_{15}$ are taken together and are alkanediyl$_{(C\leq 8)}$, alkoxydiyl$_{(C\leq 8)}$, alkylaminodiyl$_{(C\leq 8)}$, or a substituted version of any of these groups;
- $R_{20}$ and $R_{21}$ are each independently hydrogen, alkyl$_{(C\leq 8)}$, alkenyl$_{(C\leq 8)}$, aryl$_{(C\leq 12)}$, aralkyl$_{(C\leq 12)}$, acyl$_{(C\leq 8)}$, or a substituted version of any of these groups; and
- $R_{23}$ is hydroxy, alkoxy$_{(C\leq 12)}$, or substituted alkoxy$_{(C\leq 12)}$;

or a salt, tautomer, or optical isomer thereof.

\* \* \* \* \*

UNITED STATES PATENT AND TRADEMARK OFFICE
CERTIFICATE OF CORRECTION

PATENT NO. : 10,065,924 B2
APPLICATION NO. : 15/327912
DATED : September 4, 2018
INVENTOR(S) : Kyriacos C Nicolaou et al.

Page 1 of 1

It is certified that error appears in the above-identified patent and that said Letters Patent is hereby corrected as shown below:

In the Claims

In Claim 2, Column 64, Line 48, delete "$_{(C\leq 8)}$" and insert --$_{(C\leq 18)}$-- therefor.

In Claim 4, Column 66, Lines 48-52, delete the entire contents and insert
--$R_4$ is hydrogen, alkyl$_{(C\leq 8)}$, or substituted alkyl$_{(C\leq 8)}$,
$R_5$ is hydrogen,
alkyl$_{(C\leq 8)}$, alkanediyl$_{(C\leq 8)}$–heterocycloalkyl$_{(C\leq 8)}$, alkanediyl$_{(C\leq 8)}$–heteroaryl$_{(C\leq 8)}$,
    alkanediyl$_{(C\leq 8)}$–alkylamino$_{(C\leq 8)}$, alkanediyl$_{(C\leq 8)}$–dialkylamino$_{(C\leq 8)}$, or a
    substituted version of any of these groups;-- therefor.

In Claim 7, Column 69, Line 52, delete "carboxy,".

In Claim 19, Column 74, Line 37, delete "$R_{15}$ taken" and insert --$R_{15}$ are taken-- therefor.

Signed and Sealed this
Thirteenth Day of November, 2018

Andrei Iancu
*Director of the United States Patent and Trademark Office*